(12) United States Patent
Inghardt

(10) Patent No.: US 7,645,751 B2
(45) Date of Patent: *Jan. 12, 2010

(54) MANDELIC ACID DERIVATIVES AND THEIR USE AS THROMBIN INHIBITORS

(75) Inventor: Tord Inghardt, Mölndal (SE)

(73) Assignee: AstraZeneca, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/797,656

(22) Filed: May 4, 2007

(65) Prior Publication Data

US 2008/0090800 A1 Apr. 17, 2008

Related U.S. Application Data

(60) Continuation of application No. 11/520,063, filed on Sep. 13, 2006, which is a division of application No. 10/432,411, filed as application No. PCT/SE01/02657 on Nov. 30, 2001, now Pat. No. 7,129,233.

(30) Foreign Application Priority Data

| Dec. 1, 2000 | (SE) | .................................... 0004458 |
| Mar. 19, 2001 | (SE) | .................................... 0100965 |
| Apr. 6, 2001 | (SE) | .................................... 0101239 |
| Aug. 30, 2001 | (SE) | .................................... 0102921 |

(51) Int. Cl.
  *A61K 31/397* (2006.01)
  *C07D 205/04* (2006.01)

(52) U.S. Cl. .......................... 514/210.02; 514/210.17; 548/952; 548/953

(58) Field of Classification Search ............ 514/210.02, 514/210.17; 548/952, 953
See application file for complete search history.

(56) References Cited

U.S. PATENT DOCUMENTS

| 4,346,078 | A | 8/1982 | Bajusz et al. |
| 4,792,452 | A | 12/1988 | Howard et al. |
| 5,053,416 | A | 10/1991 | Toja et al. |
| 5,498,724 | A | 3/1996 | Nystrom et al. |
| 5,559,232 | A | 9/1996 | Ackermann et al. |
| 5,602,253 | A | 2/1997 | Antonsson et al. |
| 5,659,071 | A | 8/1997 | Nystrom et al. |
| 5,705,487 | A | 1/1998 | Schacht et al. |
| 5,707,966 | A | 1/1998 | Schacht et al. |
| 5,710,130 | A | 1/1998 | Schacht et al. |
| 5,723,444 | A | 3/1998 | Antonsson et al. |
| 5,744,487 | A | 4/1998 | Ohshima et al. |
| 5,780,631 | A | 7/1998 | Antonsson et al. |
| 5,783,563 | A | 7/1998 | Antonsson et al. |
| 5,856,307 | A | 1/1999 | Antonsson et al. |
| 5,939,392 | A | 8/1999 | Antonsson et al. |
| 5,965,692 | A | 10/1999 | Gustafsson et al. |
| 6,030,972 | A | 2/2000 | Bohm et al. |
| 6,034,104 | A | 3/2000 | Klimkowski et al. |
| 6,051,568 | A | 4/2000 | Gustafsson et al. |
| 6,083,532 | A | 7/2000 | Zhang et al. |
| 6,221,898 | B1 | 4/2001 | Antonsson |
| 6,225,287 | B1 | 5/2001 | Edvardsson et al. |
| 6,255,301 | B1 | 7/2001 | Gustafsson et al. |
| 6,262,028 | B1 | 7/2001 | Antonsson et al. |
| 6,265,397 | B1 | 7/2001 | Karlsson et al. |
| 6,287,599 | B1 | 9/2001 | Burnside et al. |
| 6,337,343 | B1 | 1/2002 | Gustafsson et al. |
| 6,337,394 | B2 | 1/2002 | Karlsson et al. |
| 6,433,186 | B1 | 8/2002 | Inghardt et al. |
| 6,440,937 | B1 | 8/2002 | Baucke et al. |
| 6,440,939 | B2 | 8/2002 | Edvardsson et al. |
| 6,444,817 | B1 | 9/2002 | Bohm et al. |
| 6,455,671 | B1 | 9/2002 | Bohm et al. |
| 6,479,078 | B1 | 11/2002 | Hedstrom et al. |
| 6,521,253 | B1 | 2/2003 | Forsman et al. |
| 6,576,245 | B1 | 6/2003 | Lundgren et al. |
| 6,576,657 | B2 | 6/2003 | Karlsson et al. |
| 6,599,894 | B1 | 7/2003 | Inghardt et al. |
| 6,617,320 | B2 | 9/2003 | Gustafsson et al. |
| 6,660,279 | B2 | 12/2003 | Lundgren et al. |

(Continued)

FOREIGN PATENT DOCUMENTS

| EP | 0185390 | 10/1991 |
| EP | 0526877 | 2/1993 |
| EP | 0293881 | 3/1993 |
| EP | 0530167 | 3/1993 |
| EP | 0539059 | 4/1993 |
| EP | 0195212 | 11/1993 |
| EP | 0468231 | 9/1994 |
| EP | 0641779 | 3/1995 |
| EP | 0648780 | 4/1995 |
| EP | 0362002 | 7/1995 |
| EP | 0686642 | 12/1995 |
| EP | 0364344 | 5/1998 |
| EP | 0542525 | 7/1998 |
| EP | 0559046 | 7/2001 |
| EP | 0669317 | 9/2002 |

(Continued)

OTHER PUBLICATIONS

Baveja et al. "Zero-order release hydrophilic matrix tablets of beta-adrenergic blockers" International Journal of Pharmaceutics 39:39-45 (1987).

Bonferoni et al. "On the employment of lambda-carrageenan in a matrix system. II. Lambda-Carrageenan and hydroxypropylmethylcellulose mixtures" J. Controlled Release 30:175-182 (1994).

(Continued)

*Primary Examiner*—Golam M. M. Shameem
*Assistant Examiner*—Susannah Chung
(74) *Attorney, Agent, or Firm*—Morgan, Lewis & Bockius LLP

(57) ABSTRACT

There is provided a compound of formula (I) wherein $R^a$, $R^1$, $R^2$, Y and $R^3$ have meanings given in the description and pharmaceutically-acceptable derivatives (including prodrugs) thereof, which compounds and derivatives are useful as, or are useful as prodrugs of, competitive inhibitors of trypsin-like proteases, such as thrombin, and thus, in particular, in the treatment of conditions where inhibition of thrombin is required (e.g., thrombosis) or as anticoagulants.

17 Claims, No Drawings

U.S. PATENT DOCUMENTS

| | | | |
|---|---|---|---|
| 6,716,834 B2 | 4/2004 | Andersson et al. | |
| 6,750,243 B1 | 6/2004 | Inghardt et al. | |
| 6,811,794 B2 | 11/2004 | Burnside et al. | |
| 6,838,478 B2 | 1/2005 | Gustafsson et al. | |
| 6,875,446 B2 | 4/2005 | Forsman et al. | |
| 6,888,007 B2 | 5/2005 | Edvardsson et al. | |
| 6,921,758 B2 | 7/2005 | Gustafsson et al. | |
| 6,984,627 B1 | 1/2006 | Antonsson et al. | |
| 6,998,136 B2 | 2/2006 | Lundgren et al. | |
| 7,056,907 B2 * | 6/2006 | Inghardt et al. | 514/210.02 |
| 7,129,233 B2 | 10/2006 | Inghardt et al. | |
| 7,202,236 B2 | 4/2007 | Magnusson et al. | |
| 7,273,858 B2 | 9/2007 | Ahlqvist et al. | |
| 2004/0019033 A1 | 1/2004 | Inghardt et al. | |
| 2004/0242492 A1 | 12/2004 | Inghardt et al. | |
| 2004/0242536 A1 | 12/2004 | Khoo et al. | |
| 2005/0171083 A1 | 8/2005 | Magnusson et al. | |
| 2006/0014734 A1 | 1/2006 | Alami et al. | |
| 2007/0202174 A1 | 8/2007 | Inghardt et al. | |
| 2007/0218136 A1 | 9/2007 | Inghardt et al. | |
| 2008/0050437 A1 | 2/2008 | Magnusson et al. | |
| 2008/0269176 A1 | 10/2008 | Ahlqvist et al. | |
| 2008/0287413 A1 | 11/2008 | Aslund et al. | |
| 2008/0293965 A1 | 11/2008 | Bosson | |
| 2008/0312457 A1 | 12/2008 | Blixt et al. | |
| 2008/0319206 A1 | 12/2008 | Al-Saffar et al. | |

FOREIGN PATENT DOCUMENTS

| | | |
|---|---|---|
| EP | 0773955 | 4/2003 |
| EP | 0672658 | 9/2003 |
| JP | 57149217 | 9/1982 |
| WO | WO 93/11152 | 6/1993 |
| WO | WO 93/18060 | 9/1993 |
| WO | WO 94/29269 | 12/1994 |
| WO | WO 94/29336 | 12/1994 |
| WO | WO 95/23609 | 9/1995 |
| WO | WO 95/35309 | 12/1995 |
| WO | WO 96/03374 | 2/1996 |
| WO | WO 96/25426 | 8/1996 |
| WO | WO 96/26717 | 9/1996 |
| WO | WO 96/31504 | 10/1996 |
| WO | WO 96/32110 | 10/1996 |
| WO | WO 97/02284 | 1/1997 |
| WO | WO 97/23499 | 7/1997 |
| WO | WO 97/39770 | 10/1997 |
| WO | WO 97/46577 | 12/1997 |
| WO | WO 97/49404 | 12/1997 |
| WO | WO 98/01422 | 1/1998 |
| WO | WO 98/06740 | 2/1998 |
| WO | WO 98/16252 | 4/1998 |
| WO | WO 98/57932 | 12/1998 |
| WO | WO 99/21586 | 5/1999 |
| WO | WO 99/27913 | 6/1999 |
| WO | WO 99/29305 | 6/1999 |
| WO | WO 99/29664 | 6/1999 |
| WO | WO 99/39698 | 8/1999 |
| WO | WO 00/12043 | 3/2000 |
| WO | WO 00/13671 | 3/2000 |
| WO | WO 00/13710 | 3/2000 |
| WO | WO 00/14110 | 3/2000 |
| WO | WO 00/18352 | 4/2000 |
| WO | WO 00/35869 | 6/2000 |
| WO | WO 00/42059 | 7/2000 |
| WO | WO 01/02426 | 1/2001 |
| WO | WO 01/87879 | 11/2001 |
| WO | WO 02/14270 | 2/2002 |
| WO | WO 02/19990 | 3/2002 |
| WO | WO 02/44145 | 6/2002 |
| WO | WO 03/000293 | 1/2003 |
| WO | WO 03/018551 | 3/2003 |
| WO | WO 03/090723 | 11/2003 |
| WO | WO 03/101423 | 12/2003 |
| WO | WO 03/101424 | 12/2003 |
| WO | WO 03/101957 | 12/2003 |
| WO | WO 2005/054168 | 6/2005 |
| WO | WO 2006/090153 | 8/2006 |
| WO | WO 2006/125964 | 11/2006 |
| WO | WO 2008/068475 | 6/2008 |

OTHER PUBLICATIONS

Berge et al. "Pharmaceutical Salts" J. of Pharmaceutical Sciences 66(1): 1-19 (1977).
Ham-Yong Park et al. "Effect of pH on Drug Release From Polysaccharide Tablets" Drug Delivery 5:13-18 (1998).
Picker "The use of carrageenan in mixture with microcrystalline cellulose and its functionality for making tablets" European J Pharmaceutics and Biopharmaceutics 48(1):27-36 (1999).
Talukdar et al. "In vivo evaluation of xanthan gum as a potential excipient for oral controlled-release matrix tablet formulation" International Journal of Pharmaceutics 169(1):105-113 (1998).
CAS RN 159776-70-2 Dec. 1994.
CAS RN 192939-72-3 Aug. 1997.
CAS RN 30318-53-4 Nov. 2000.
Gupta et al. "Controlled-release tablets from carrageenans: effect of formulation, storage and dissolution factors" Eur. J. Pharm. Biopharm., 51(3):241-248 (2001).
Talukdar et al. "Comparative study on xanthan gum and hydroxypropylmethyl cellulose as matrices for controlled-release drug delivery I. Compaction and in vitro drug release behaviour" International Journal of Pharmaceutics, 129(2):233-241 (1996).
Deinum et al. "Biochemical and pharmacological effects of the direct thrombin inhibitor AR-H067637" Thromb Haemost. 101(6):1051-1059 (2009).
Eriksson et al. "Comparative pharmacodynamics and pharmacokinetics of oral direct thrombin and factor Xa inhibitors in development" Clinical Pharmacokinetics 48(1):1-22 (2009).
Lip et al. "The oral direct thrombin inhibitor AZD0837 for the prevention of stroke and systemic embolism in patients with atrial fibrillation: A phase II randomized dose-guiding, safety and tolerability study" Journal of the American College of Cardiology 53(10, Suppl. 1):A430 (2009).
Gyzander et al. "Enzyme kinetic characterisation of the active form of the novel oral direct thrombin inhibitor AZD0837" Journal of Thrombosis and Haemostasis, 5 Supplement 2: P-S-066 (2007).
Hockings et al. "The oral direct thrombin inhibitor AZD0837 reduces thrombus formation in a rat model" Journal of Thrombosis and Haemostasis, 5 Supplement 2: P-S-697 (2007).
Mattsson et al. "Characterisation of the active form of the novel oral direct thrombin inhibitor AZD0837 in coagulation assays" Journal of Thrombosis and Haemostasis, 5 Supplement 2: P-T-636 (2007).
Olsson et al. "Safety and tolerability of the oral direct thrombin inhibitor AZD0837 in prevention of stroke and other thromboembolic complications associated with atrial fibrillation (AF)" Journal of Thrombosis and Haemostasis, 5 Supplement 2: O-W-053 (2007).
Patani et al. "Bioisosterism: A rational approach in drug design" Chem. Rev. 96(8):3147-3176 (1996).
Pehrsson et al. "The antithrombotic effect of AR-H067637, the active form of the novel oral direct thrombin inhibitor AZD0837, in rat models of arterial and venous thrombosis" Journal of Thrombosis and Haemostasis, 5 Supplement 2 : P-W-637 (2007).
Schutzer et al. "Effect of the oral direct thrombin inhibitor AZD0837 on glomerular filtration rate in elderly healthy subjects" Journal of Thrombosis and Haemostasis, 5 Supplement 2: P-W-668 (2007).
Wagenvoord et al. "The effect of direct thrombin inhibitors (DTIS) in clotting plasma" Journal of Thrombosis and Haemostasis, 5 Supplement 2: P-W-654 (2007).
Walfridsson et al. "Assessment of the electrophysiological effects of the oral direct thrombin inhibitor AZD0837, in subjects undergoing an invasive electrophysiological procedure" Journal of Thrombosis and Haemostasis, 5 Supplement 2 : P-W-674 (2007).

* cited by examiner

MANDELIC ACID DERIVATIVES AND THEIR USE AS THROMBIN INHIBITORS

RELATED APPLICATIONS

This is a continuation application of U.S. application Ser. No. 11/520,063 (filed Sep. 13, 2006), which is a divisional application of U.S. application Ser. No. 10/432,411 (filed May 21, 2003, now U.S. Pat. No. 7,129,233, issued Oct. 31, 2006), which is a U.S. National Phase Application of International Application No. PCT/SE01/02657 (filed Nov. 30, 2001), which claims the benefit of Swedish Application No. 0004458-6 (filed Dec. 1, 2000), Swedish Patent Application No. 0 100965-3 (filed Mar. 19, 2001), Swedish Patent Application No. 0101239-2 (filed Apr. 6, 2001), and Swedish Patent Application No. 0102921-4 (filed Aug. 30, 2001), all of which are herein incorporated by reference in their entirety.

FIELD OF THE INVENTION

This invention relates to novel pharmaceutically useful compounds, in particular compounds that are, and/or compounds that are metabolised to compounds which are, competitive inhibitors of trypsin-like serine proteases, especially thrombin, their use as medicaments, pharmaceutical compositions containing them and synthetic routes to their production.

BACKGROUND

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would be expected to exhibit antithrombotic activity. In addition, antithrombotic activity would be expected to be enhanced by effective inhibition of the positive feedback mechanism.

PRIOR ART

The early development of low molecular weight inhibitors of thrombin has been described by Claesson in Blood Coagul. Fibrinol. (1994) 5, 411.

Blombäck et al (in J. Clin. Lab. Invest. 24, suppl. 107, 59, (1969)) reported thrombin inhibitors based on the amino acid sequence situated around the cleavage site for the fibrinogen Aα chain. Of the amino acid sequences discussed, these authors suggested the tripeptide sequence Phe-Val-Arg (P9-P2-P1, hereinafter referred to as the P3-P2-P1 sequence) would be the most effective inhibitor.

Thrombin inhibitors based on dipeptidyl derivatives with an α,ω-aminoalkyl guanidine in the P1-position are known from U.S. Pat. No. 4,346,078 and International Patent Application WO 93/11152. Similar, structurally related, dipeptidyl derivatives have also been reported. For example International Patent Application WO 94/29336 discloses compounds with, for example, aminomethyl benzamidines, cyclic aminoalkyl amidines and cyclic aminoalkyl guanidines in the P1-position (International Patent Application WO 97/23499 discloses prodrugs of certain of these compounds); European Patent Application 0 648 780, discloses compounds with, for example, cyclic aminoalkyl guanidines in the P1-position.

Thrombin inhibitors based on peptidyl derivatives, also having cyclic aminoalkyl guanidines (e.g. either 3- or 4-aminomethyl-1-amidino-piperidine) in the P1-position are known from European Patent Applications 0 468 231, 0 559 046 and 0 641 779.

Thrombin inhibitors based on tripeptidyl derivatives with arginine aldehyde in the P1-position were first disclosed in European Patent Application 0 185 390.

More recently, arginine aldehyde-based peptidyl derivatives, modified in the P3-position, have been reported. For example, International Patent Application WO 93/18060 discloses hydroxy acids, European Patent Application 0 526 877 des-amino acids, and European Patent Application 0 542 525 0-methyl mandelic acids in the P3-position.

Inhibitors of serine proteases (e.g. thrombin) based on electrophilic ketones in the P1-position are also known. For example, European Patent Application 0 195 212 discloses peptidyl α-keto esters and amides, European Patent Application 0.362 002 fluoroalkylamide ketones, European Patent Application 0 364 344 α,β,δ-triketocompounds, and European Patent Application 0 530 167 α-alkoxy ketone derivatives of arginine in the P1-position.

Other, structurally different, inhibitors of trypsin-like serine proteases based on C-terminal boronic acid derivatives of arginine and isothiouronium analogues thereof are known from European Patent Application 0 293 881.

More recently, thrombin inhibitors based on peptidyl derivatives have been disclosed in European Patent Application 0 669 317 and International Patent Applications WO 95/35309, WO 95/23609, WO 96/25426, WO 97/02284, WO 97/46577, WO 96/32110, WO 96/31504, WO 96/03374, WO 98/06740, WO 97/49404, WO 98/57932, WO 99/29664, WO 00/35869 and WO 00/42059.

In particular, WO 97/02284 and WO 00/42059 disclose thrombin inhibitors with substituted mandelic acids in the P3 position.

However, there remains a need for effective inhibitors of trypsin-like serine proteases, such as thrombin. There is also a need for compounds which have a favourable pharmacokinetic profile and are selective in inhibiting thrombin over other serine proteases, in particular those involved in haemostasis. Compounds which exhibit competitive inhibitory activity towards thrombin would be expected to be especially useful as anticoagulants and therefore in the therapeutic treatment of thrombosis and related disorders.

DISCLOSURE OF THE INVENTION

According to the invention there is provided a compound of formula I

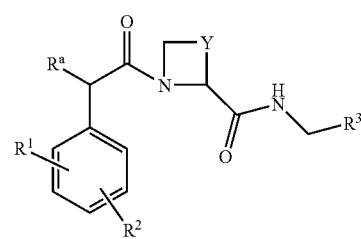

I wherein $R^a$ represents —OH or —CH$_2$OH;

$R^1$ represents at least one optional halo substituent;

$R^2$ represents one or two $C_{1-3}$ alkoxy substituents, the alkyl parts of which substituents are themselves substituted with one or more fluoro substituents (i.e. $R^2$ represents one or two fluoroalkoxy($C_{1-3}$) groups);

Y represents —CH$_2$— or —(CH$_2$)$_2$—; and $R^3$ represents a structural fragment of formula I(i) or I(ii):

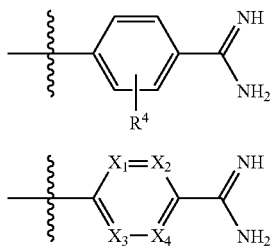

wherein $R^4$ represents H or one or more fluoro substituents; and one or two of $X_1$, $X_2$, $X_3$ and $X_4$ represent —N— and the others represent —CH—, or a pharmaceutically-acceptable derivative thereof.

The term "pharmaceutically-acceptable derivatives" includes pharmaceutically-acceptable salts (e.g. acid addition salts).

Abbreviations are listed at the end of this specification. The wavy lines on the bonds in the fragments of formulae I(i) and I(ii) signify the bond positions of the fragments.

Halo groups which $R^1$ may represent include, fluoro, chloro, bromo and iodo. For the avoidance of doubt, in representing at least one optional halo group, $R^1$ may either not be present (and thus be replaced by H, so that the rules, of valency are adhered to) or it may represent one or more halo atoms.

When $R^3$ represents a structural fragment of formula I(i) in which $R^4$ represents one or more fluoro substituents, preferred compounds of formula I include those in which $R^4$ represents a single fluoro substituent in the 2- or the 3-position, or two fluoro substituents in either the 2- and 5-positions or, more preferably, the 2- and 6-positions (wherein the substituent positions are determined in relation to the point of attachment of the structural fragment of formula I(i) to the rest of the molecule (i.e. to the —NHCH$_2$— group)).

When $R^3$ represents a structural fragment of formula I(ii), preferred compounds of formula I include those in which either:

(a) one of $X_1$, $X_2$, $X_3$ and $X_4$ represents —N— and the others represent —CH—; or (b) either $X_1$ and $X_3$, or $X_2$ and $X_4$, both represent —N— and the other two (as appropriate) represent —CH—.

Preferred compounds of formula I include those in which:

$R^1$ represents a single fluoro, chloro or bromo substituent;

$R^2$ represents $C_{1-2}$ alkoxy substituted by one or more fluoro substituents, such as —OCHF$_2$, —OCF$_3$, —OCH$_2$CF$_3$, —OCH$_2$CHF$_2$, —OCH$_2$CH$_2$F or —OCH(CH$_2$F)$_2$;

$R^3$ represents a structural fragment of formula I(i);

$R^4$ represents H.

More preferred compounds of formula I include those in which:

$R^a$ represents OH;

$R^1$ represents a single chloro substituent;

$R^2$ represents —OCF$_3$, preferably —OCH$_2$CHF$_2$, or more preferably —OCHF$_2$, or —OCH$_2$CH$_2$F.

Preferred points of substitution of $R^1$ and $R^2$ on the relevant phenyl group of compounds of formula I include the two meta-positions relative to the point of attachment of that phenyl group to the rest of the molecule (i.e. at the 3- and/or the 5-position (preferably 3,5-substitution) relative to the carbon atom bearing the α- or β-hydroxy acid group).

Compounds of formula I that may be mentioned include those in which:

$R^2$ represents one or two $C_{1-2}$ alkoxy substituents, the alkyl parts of which substituents are themselves substituted by one or more fluoro substituents; or $R^2$ represents one or two $C_3$ alkoxy substituents, the alkyl parts of which substituents are themselves substituted by one or more fluoro substituents.

Compounds of formula I may be made in accordance with techniques well known to those skilled in the art, for example as described hereinafter.

According to a further aspect of the invention there is provided a process for the preparation of a compound of formula I, which comprises:

(i) the coupling of a compound of formula II,

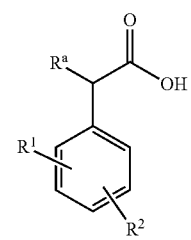

wherein $R^a$, $R^1$ and $R^2$ are as hereinbefore defined with a compound of formula III,

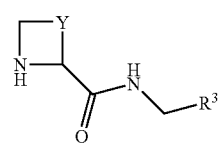

wherein Y and $R^3$ are as hereinbefore defined, for example in the presence of a coupling agent (e.g. oxalyl chloride in DMF, EDC, DCC, HBTU, HATU, PyBOP or TBTU), an appropriate base (e.g. pyridine, DMAP, TEA, 2,4,6-collidine or DIPEA) and a suitable organic solvent (e.g. dichloromethane, acetonitrile, EtOAc or DMF);

(ii) the coupling of a compound of formula IV,

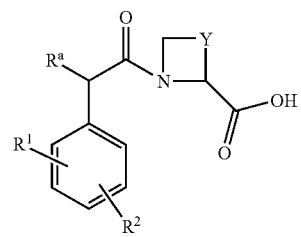

wherein $R^a$, $R^1$, $R^2$ and Y are as hereinbefore defined with a compound of formula V,

wherein $R^3$ is as hereinbefore defined, for example under conditions as described in process (i) above;

(iii) for compounds of formula I in which $R^1$ is not present, reduction of a corresponding compound of formula Ia, as defined hereinafter, in which $R^5$ represents $OR^6$, wherein $R^5$ and $R^6$ are as defined hereinafter, for example by hydrogenation in the presence of a suitable catalyst (e.g. a supported metal catalyst such as Pd/C (e.g. 10% (w/w) Pd/C)) and an appropriate solvent (e.g. a lower (e.g. $C_{1-6}$) alkyl alcohol such as ethanol), and optionally in the presence of a suitable acid (e.g. acetic acid) and/or as described in *Synth. Comm.* (1998) 4351; or (iv) reaction of a corresponding compound of formula XVIA or XVIB, as defined hereinafter, with a suitable source of ammonia (e.g. ammonium acetate or ammonia gas) under conditions known to those skilled in the art, such as by reaction of an ethylimidoate intermediate (formed by reaction of a compound of formula XVIA or XVIB with HCl(g) in ethanol) with ammonia gas in ethanol, or under those conditions described in *Tetrahedron Lett.* 40, 7067 (1999), the disclosures of which document are hereby incorporated by reference (for example, for preparation of compounds of formula I in which $R^3$ represents a structural fragment of formula I(ii) in which $X_2$ or $X_4$ represents N, reaction of a corresponding compound of formula XVIB with ammonium acetate (e.g. 1 to 30 equivalents of ammonium acetate) in the presence of N-acetyl cysteine (e.g. 1 to 30 equivalents of N-acetyl cysteine) and an appropriate solvent (e.g. a lower alkyl (e.g. $C_{1-6}$) alcohol such as methanol)).

Compounds of formula II are available using known and/or standard techniques.

For example, compounds of formula II in which $R^a$ represents OH may be prepared by reaction of an aldehyde of formula VI,

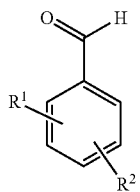

wherein $R^1$ and $R^2$ are as hereinbefore defined with:
(a) a compound of formula VII,

wherein R" represents H or $(CH_3)_3Si$, for example at room, or elevated, temperature (e.g. below 100° C.) in the presence of a suitable organic solvent (e.g. chloroform or methylene chloride) and, if necessary, in the presence of a suitable base (e.g. TEA) and/or a suitable catalyst system (e.g. benzylammonium chloride or zinc iodide, or using a chiral catalyst, for example as described in *Chem. Rev.*, (1999) 99, 3649), followed by hydrolysis under conditions that are well known to those skilled in the art (e.g. as described hereinafter);

(b) NaCN or KCN, for example in the presence of NaHSO₃ and water, followed by hydrolysis;

(c) chloroform, for example at elevated temperature (e.g. above room temperature but below 100° C.) in the presence of a suitable organic solvent (e.g. chloroform) and, if necessary, in the presence of a suitable catalyst system (e.g. benzylammonium chloride), followed by hydrolysis;

(d) a compound of formula VIII,

wherein M represents Mg or Li, followed by oxidative cleavage (e.g. ozonolysis or osmium or ruthenium catalysed) under conditions which are well known to those skilled in the art; or (e) tris(methylthio)methane under conditions which are well known to those skilled in the art, followed by hydrolysis in the presence of e.g. HgO and HBF₄.

Compounds of formula II in which $R^a$ represents —CH₂OH may be prepared by reduction of a compound of formula IX,

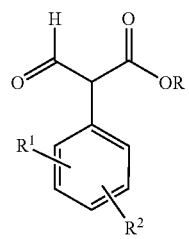

wherein R represents $C_{1-6}$ alkyl or $C_{1-3}$ alkylphenyl and $R^1$ and $R^2$ are as hereinbefore defined, for example at room temperature or below in the presence of a suitable reducing agent (e.g. sodium borohydride) and an appropriate organic solvent (e.g. methanol, ethanol, THF or mixtures thereof), followed by hydrolysis of the resultant tropic acid ester intermediate of formula IXA,

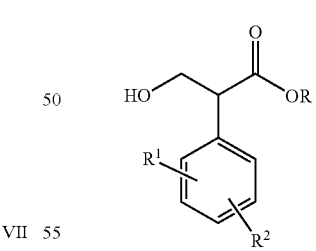

wherein R, $R^1$ and $R^2$ are as hereinbefore defined, under conditions that are well known to those skilled in the art, for example as described hereinafter. The skilled person will appreciate that the reduction and hydrolysis steps may be carried out as a one-pot procedure, for example as described hereinafter.

Compounds of formula II in which $R^a$ represents —OH may alternatively be prepared by oxidation of a compound of formula IXB,

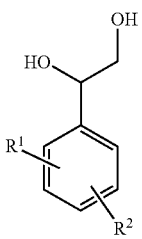

IXB or a derivative thereof that is optionally protected at the secondary hydroxyl group, wherein $R^1$ and $R^2$ are as hereinbefore defined, in the presence of a suitable oxidising agent (e.g. a combination of a suitable free radical oxidant (such as TEMPO) and an appropriate hypochlorite salt (such as sodium hypochlorite)) under conditions known to those skilled in the art, for example at between −10° C. and room temperature, in the presence of a suitable solvent (e.g. water, acetone or a mixture thereof), an appropriate salt (e.g. an alkali metal halide such as potassium bromide) and a suitable base (e.g. an alkali metal carbonate or hydrogen carbonate such as sodium hydrogen carbonate).

The enantiomeric forms of the compound of formula II in which $R^a$ represents —OH (i.e. those compounds having different configurations of substituents about the C-atom α-to the $CO_2H$ group) may be separated by an enantiospecific derivatisation step. This may be achieved, for example by an enzymatic process. Such enzymatic processes include, for example, transesterification of the α-OH group at between room and reflux temperature (e.g. at between 45 and 65° C.) in the presence of a suitable enzyme (e.g. Lipase PS Amano), an appropriate ester (e.g. vinyl acetate) and a suitable solvent (e.g. methyl tert-butyl ether). The derivatised isomer may then be separated from the unreacted isomer by conventional separation techniques (e.g. chromatography).

Groups added to compounds of formula II in such a derivatisation step may be removed either before any further reactions or at any later stage in the synthesis of compounds of formula I. The additional groups may be removed using conventional techniques (e.g. foresters of the α-OH group, hydrolysis under conditions known to those skilled in the art (e.g. at between room and reflux temperature in the presence of a suitable base (e.g. NaOH) and an appropriate solvent (e.g. MeOH, water or mixtures thereof))).

The enantiomeric forms of the compound of formula II in which $R^a$ represents —$CH_2OH$ may be separated by chiral chromatographic techniques (e.g. chiral HPLC).

Compounds of formula III may be prepared by coupling a compound of formula X,

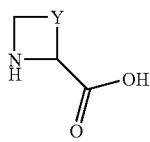

X wherein Y is as hereinbefore defined to a compound of formula V, as hereinbefore defined, for example under similar conditions to those described herein for preparation of compounds of formula I.

Compounds of formula IV may be prepared by coupling a compound of formula II as hereinbefore defined to a compound of formula X as hereinbefore defined, for example under similar conditions to those described herein for preparation of compounds of formula I.

Compounds of formula VI are available using known and/or standard techniques. For example, they may be prepared by:

(i) metallation (wherein the metal may be, for example, an alkali metal such as Li or, preferably, a divalent metal such as Mg) of a compound of formula XI,

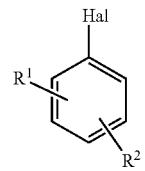

XI wherein Hal represents a halogen atom selected from Cl, Br and I and $R^1$ and $R^2$ are as hereinbefore defined, followed by reaction with a suitable source of the formyl group (such as N,N-dimethylformamide), for example under conditions described hereinafter;

(ii) reduction of a compound of formula XII,

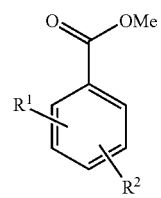

XII wherein $R^1$ and $R^2$ are as hereinbefore defined in the presence of a suitable reducing agent (e.g. DIBAL-H); or (iii) oxidation of a compound of formula XIII,

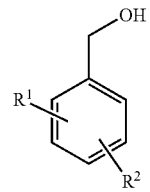

XIII wherein $R^1$ and $R^2$ are as hereinbefore defined in the presence of a suitable oxidising agent (e.g. $MnO_2$, pyridinium chlorochromate, a combination of DMSO and oxalyl chloride, or $SO_3$ pyridine complex in DMSO).

Compounds of formula IX may be prepared from the corresponding phenylacetate (which may, for example, be obtained from the corresponding acetophenone, as described in *J. Am. Chem. Soc.* 98, 6750 (1976) or from the corresponding benzyl cyanide by standard hydrolytic procedures) by conventional techniques, for example analogously to those techniques described in *J. Org. Chem.* 54, 3831 (1989) and/or as described hereinafter.

Compounds of formula IXB may be prepared by dihydroxylation of a corresponding compound of formula XIIIA

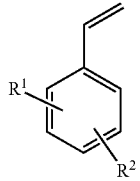

XIIIA wherein $R^1$ and $R^2$ are as hereinbefore defined, in the presence of a suitable dihydroxylating agent (e.g. a reagent or reagent mixture that provides $OsO_4$, such as AD-mix-α or, particularly, AD-mix-β), for example under conditions known to those skilled in the art, such as at between −10° C. and room temperature in the presence of an appropriate solvent (e.g. water, tert-butanol or a mixture thereof). When asymmetric oxidants such as AD-mix-α or AD-mix-β are employed, this method may be used to prepare compounds of formula IXB that have specific configurations of groups (i.e. R or S) about both of the C-atoms to which the primary and secondary hydroxyl groups are attached.

Compounds of formula XIIIA may be prepared by reaction of a corresponding compound of formula XI, as hereinbefore defined, with a suitable source of the vinyl anion (e.g. tributyl(vinyl)tin) under conditions known to those skilled in the art, for example at between room and reflux temperature (e.g. 50° C.) in the presence of an appropriate solvent (e.g. toluene), a suitable coupling agent (e.g. a palladium(0) co-ordination complex such as tetrakis(triphenylphosphine)palladium(0)) and optionally in the presence of an appropriate catalyst (e.g. 2,6-di-tert-butyl-4-methylphenol).

Compounds of formulae V, VII, VIII, X, XI, XII and XIII are either commercially available, are known in the literature, or may be obtained either by analogy with the processes described herein, or by conventional synthetic procedures, in accordance with standard techniques, from readily available starting materials using appropriate reagents and reaction conditions. Compounds of formulae Ia, XVIA and XVIB may be obtained by processes described hereinafter.

Substituents on the phenyl ring in compounds of formulae I, II, III, IV, V, VI, IX, IXA, IXB, XI, XII, XIII and XIIIA may be introduced and/or interconverted using techniques well known to those skilled in the art by way of standard functional groups interconversions, in accordance with standard techniques, from readily available starting materials using appropriate reagents and reaction conditions.

For example, compounds of formulae I, II, IV, VI, IXA, XI, XII and XIII may be prepared from corresponding compounds of formulae XIVA, XIVB, XIVC, XIVD, XIVE, XIVF, XIVG and XIVH, respectively,

XIVA

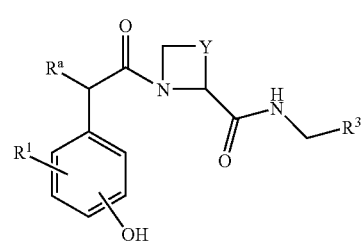

XIVB

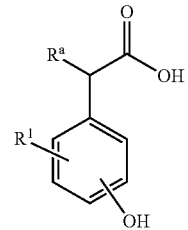

XIVC

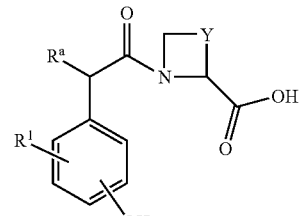

XIVD

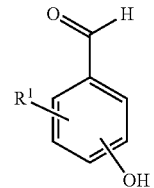

XIVE

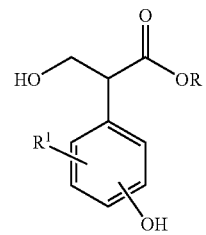

XIVF

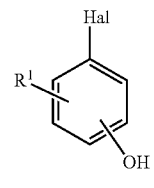

XIVG

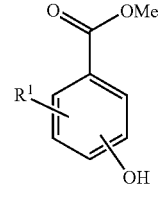

XIVH

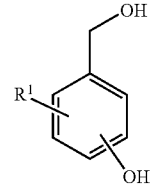

wherein $R^a$, R, $R^1$, $R^3$, Y and Hal (as appropriate) are as hereinbefore defined, for example:

(a) by reaction with a corresponding fluorinated haloalkane (e.g. a fluorinated chloroalkane), e.g. at room temperature or above (e.g. at reflux) in the presence of a suitable base (e.g. potassium tert-butoxide, KOH or NaOH, for example in aqueous solution) and an appropriate organic solvent (e.g. THF, chloroform or i-propanol); or (b) by reaction with a compound of formula XIVJ, $$R^xS(O)_2OR^y \qquad \text{XIVJ}$$

wherein $R^x$ represents $C_{1-4}$ alkyl, $C_{1-4}$ perfluoroalkyl or phenyl (optionally substituted by methyl, nitro or halo) and $R^y$ is $CH_2CF_3$, $CH_2CHF_2$, $CH_2CH_2F$ or $CH(CH_2F)_2$, for example in the presence of a suitable base (e.g. $K_2CO_3$) and an appropriate solvent (e.g. DMF), for example, in both cases, as described hereinafter.

The skilled person will appreciate that these functional group transformations may also be carried out at an earlier stage in the overall synthesis of compounds of formulae II, IV, VI, IXA, XI, XII and XIII (i.e. on appropriate precursors of compounds of formulae XIVB, XIVC, XIVD, XIVE, XIVF, XIVG and XIVH, respectively).

Compounds of formulae XIVA, XIVB, XIVC, XIVD, XIVE, XIVF, XIVG, XIVH and XIVJ are either commercially available, are known in the literature, or may be obtained either by analogy with the processes described herein, or by conventional synthetic procedures, in accordance with standard techniques, from readily available starting materials using appropriate reagents and reaction conditions. For example, compounds of formulae XIVA, XIVB, XIVC, XIVD, XIVE, XIVF, XIVG and XIVH may be obtained by deprotection of the corresponding protected phenols (where the protecting group may be, for example, methyl, allyl, benzyl or tert-butyl) under standard conditions. Further, compounds of formula XIVD in which $R^1$ is a single chloro substituent may be obtained from a di- or trihalo substituted benzene (e.g. 1-Br, 3-Cl, 5-F-benzene, by substitution of the fluorine atom with a methoxy group (e.g. by reaction with NaOMe in 1-methyl-2-pyrrolidinone/methanol at elevated temperature), replacement of the bromo group with a formyl group (e.g. as described hereinbefore for preparation of compounds of formula VI), and then demethylation (e.g. by using PhSH in 1-methyl-2-pyrollidinone in the presence of $K_2CO_3$)).

Also, compounds of formula I in which $R^1$ is absent may be prepared from corresponding compounds of formula I (or via appropriate precursors thereof) in which $R^1$ represents halo (such as chloro), for example by hydrogenation under conditions known to those skilled in the art.

Compounds of formula I may be isolated from their reaction mixtures using conventional techniques.

In accordance with the present invention, pharmaceutically acceptable derivatives of compounds of formula I also include "protected" derivatives, and/or compounds that act as prodrugs, of compounds of formula I.

Compounds that may act as prodrugs of compounds of formula I that may be mentioned include compounds of formula Ia,

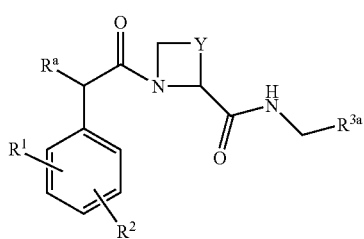

Ia wherein $R^{3a}$ represents a structural fragment of formula I(iii) or I(iv):

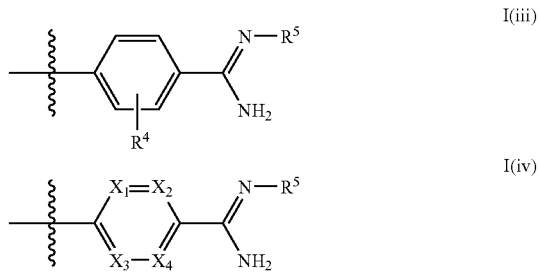

wherein $R^5$ represents $OR^6$ or $C(O)OR^7$;

$R^6$ represents H, $C_{1-10}$ alkyl, $C_{1-3}$ alkylaryl or $C_{1-3}$ alkyloxyaryl (the alkyl parts of which latter two groups are optionally interrupted by one or more oxygen atoms, and the aryl parts of which latter two groups are optionally substituted by one or more substituents selected from halo, phenyl, methyl or methoxy, which latter three groups are also optionally substituted by one or more halo substituents);

$R^7$ represents $C_{1-10}$ alkyl (which latter group is optionally interrupted by one or more oxygen atoms), or $C_{1-3}$ alkylaryl or $C_{1-3}$ alkyloxyaryl (the alkyl parts of which latter two groups are optionally interrupted by one or more oxygen atoms, and the aryl parts of which latter two groups are optionally substituted by one or more substituents selected from halo, phenyl, methyl or methoxy, which latter three groups are also optionally substituted by one or more halo substituents); and $R^a$, $R^1$, $R^2$, Y, $R^4$, $X_1$, $X_2$, $X_3$ and $X_4$ are as hereinbefore defined, and pharmaceutically-acceptable derivatives thereof.

The term "pharmaceutically-acceptable derivatives" of compounds of formula Ia includes pharmaceutically-acceptable salts (e.g. acid addition salts).

The wavy lines on the bonds in the fragments of formulae I(iii) and I(iv) signify the bond positions of the fragments.

Alkyloxyaryl groups that $R^6$ and $R^7$ may represent comprise an alkyl and an aryl group linked by way of an oxygen atom. Alkylaryl and alkyloxyaryl groups are linked to the rest of the molecule via the alkyl part of those groups, which alkyl parts may (if there is a sufficient number (i.e. three) of carbon atoms) be branched-chain. The aryl parts of alkylaryl and alkyloxyaryl groups which $R^6$ and $R^7$ may represent, or be substituted by, include carbocyclic and heterocyclic aromatic groups, such as phenyl, naphthyl, pyridinyl, oxazolyl, isoxazolyl, thiadiazolyl, indolyl and benzofuranyl and the like.

Alkyl groups which $R^6$ and $R^7$ may represent may be straight-chain or, when there is a sufficient number (i.e. a minimum of three) of carbon atoms, be branched-chain and/or cyclic. Further, when there is a sufficient number (i.e. a minimum of four) of carbon atoms, such alkyl groups may also be part cyclic/acyclic. Such alkyl groups may also be saturated or, when there is a sufficient number (i.e. a minimum of two) of carbon atoms, be unsaturated.

Halo groups with which $R^6$ and $R^7$ may be substituted include fluoro, chloro, bromo and iodo.

When $R^5$ represents $C(O)OR^7$, preferred $R^7$ groups include:

(a) linear, branched or cyclic $C_{3-6}$ alkyl, for example $C_{4-6}$ cycloalkyl;

(b) $C_{1-2}$ alkylaryl groups, such as benzyl, optionally substituted as indicated hereinbefore.

Preferred compounds of formula Ia include those in which $R^5$ represents $OR^6$.

When $R^5$ represents $OR^6$, preferred $R^6$ groups include:
(a) H;
(b) unsubstituted, linear, branched or cyclic $C_{1-8}$ (e.g. $C_{1-6}$) alkyl, such as linear $C_{1-3}$ alkyl (e.g. ethyl or, particularly, methyl), branched $C_{3-8}$ alkyl (e.g. i-propyl, i-butyl or 4-heptyl) or cyclic $C_{4-7}$ alkyl (i.e. $C_{4-7}$ cycloalkyl, e.g. cyclobutyl or cyclohexyl);
(c) $C_{1-3}$ alkyloxyphenyl (e.g. $C_2$ alkyloxyphenyl), which phenyl group is optionally substituted by one or more substituents as indicated hereinbefore (e.g. trifluoromethyl);
(d) $C_{1-2}$ alkylaryl (e.g. methylaryl), wherein the aryl group is phenyl, pyridinyl, oxazolyl or isoxazolyl, which latter three groups are optionally substituted by one or more substituents as indicated hereinbefore (e.g. methoxy, methyl, bromo and/or chloro).

Preferred compounds of formula Ia include those in which $R^5$ represents $OR^6$ and $R^6$ represents linear, branched (as appropriate), or cyclic (as appropriate), $C_{1-6}$ (e.g. $C_{1-4}$) alkyl, such as methyl, ethyl, n-propyl, i-propyl or cyclobutyl.

Compounds of formula Ia may be prepared by one or more of the following methods:
(a) reaction of a corresponding compound of formula II as hereinbefore defined with a compound of formula XV,

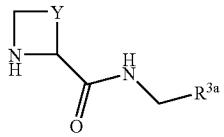

XV wherein Y and $R^{3a}$ are as hereinbefore defined, for example under similar conditions to those described hereinbefore for synthesis of compounds of formula I;
(b) reaction of a corresponding compound of formula IV as hereinbefore defined with a compound of formula XVI,

  XVI wherein $R^{3a}$ is as hereinbefore defined, for example under similar conditions to those described hereinbefore for synthesis of compounds of formula I;
(c) for compounds of formula Ia in which $R^5$ represents OH, reaction of a corresponding compound of formula XVIA or XVIB,

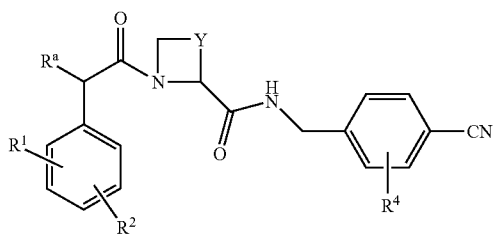

XVIA

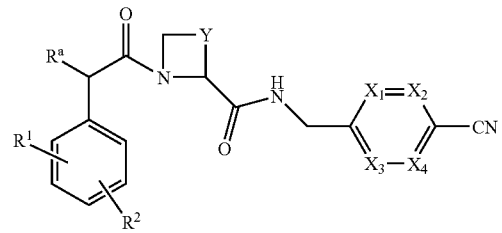

XVIB wherein $R^a$, $R^1$, $R^2$, $R^4$, Y, $X_1$, $X_2$, $X_3$ and $X_4$ are as hereinbefore defined, with hydroxylamine, for example under conditions known to those skilled in the art;
(d) for compounds of formula Ia in which $R^5$ represents $OR^6$, reaction of a protected derivative of a corresponding compound of formula I which is, for example, a compound of formula XVII,

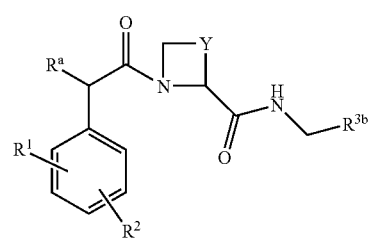

XVII wherein $R^{3b}$ represents a structural fragment of formula I(v) or I(vi):

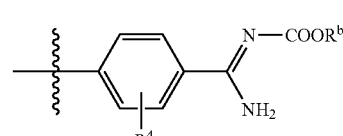

I(v)

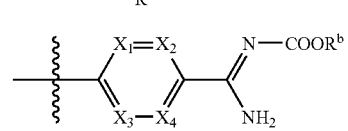

I(vi)

wherein $R^b$ represents, for example, $-CH_2CH_2-Si(CH_3)_3$ or benzyl, or a tautomer thereof, and $R^a$, $R^1$, $R^2$, Y, $R^4$, $X_1$, $X_2$, $X_3$ and $X_4$ are as hereinbefore defined with a compound of formula XVIII,

  XVIII wherein $R^6$ is as hereinbefore defined, or an acid addition salt thereof, for example at between room and reflux temperature in the presence of an appropriate organic solvent (e.g. THF, $CH_3CN$, DMF or DMSO), followed by removal of the $-C(O)OR^b$ group under conditions known to those skilled in the art (e.g. by reacting with QF or TFA (e.g. as described hereinafter));
(e) for compounds of formula Ia in which $R^5$ represents OH, reaction of a compound of formula XVII, as hereinbefore defined, in which $R^b$ represents benzyl with hydroxylamine, or an acid addition salt thereof, for example under conditions that will be well known to those skilled in the art;

(f) for compounds of formula Ia in which $R^5$ represents $COOR^7$, reaction of a corresponding compound of formula I as hereinbefore defined with a compound of formula XIX, $$L^1COOR^7 \qquad XIX$$

wherein $L^1$ represents a suitable leaving group, such as halo or nitrophenyl (e.g. 4-nitrophenyl), and $R^7$ is as hereinbefore defined, for example at or around room temperature in the presence of suitable base (e.g. NaOH, for example in aqueous solution) and an appropriate organic solvent (e.g. methylene chloride); or (g) for compounds of formula Ia in which $R^5$ represents $OCH_3$ or $OCH_2CH_3$, reaction of a corresponding compound of formula Ia in which $R^5$ represents OH with dimethylsulfate or diethylsulfate, respectively, for example in the presence of a suitable base (e.g. an alkali metal hydroxide such as KOH (for example in aqueous solution at e.g. 50 wt. %)) and an appropriate catalyst (e.g. a quaternary ammonium halide such as benzyltrimethylammonium chloride (for example in $CH_2Cl_2$ or THF solution at e.g. 10 wt. %)).

The wavy lines on the bonds in the fragments of formulae I(v) and I(vi) signify the bond positions of the fragments.

Compounds of formulae XVIA and XVIB may be prepared by reaction of a corresponding compound of formula II, as hereinbefore defined, with a compound of formula XIXA or XIXB,

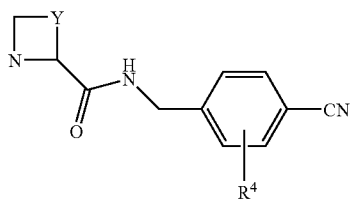

XIXA

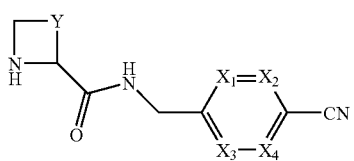

XIXB wherein $R^4$, Y, $X_1$, $X_2$, $X_3$ and $X_4$ are as hereinbefore defined, for example under similar conditions to those described hereinbefore for synthesis of compounds of formula I.

Compounds of formulae XVIA and XVIB may alternatively be prepared by reaction of a corresponding compound of formula IV, as hereinbefore defined, with a compound of formula XIXC or XIXD,

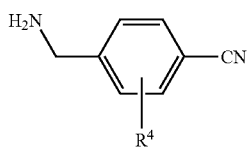

XIXC

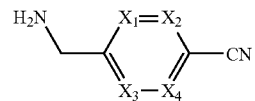

XIXD wherein $R^4$, $X_1$, $X_2$, $X_3$ and $X_4$ are as hereinbefore defined, for example under similar conditions to those described hereinbefore for synthesis of compounds of formula I.

Compounds of formula XVII may be prepared by reaction of a corresponding compound of formula II, as hereinbefore defined, with a compound of formula XX,

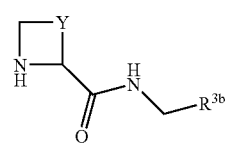

XX wherein Y and $R^{3b}$ are as hereinbefore defined, for example under similar conditions to those described hereinbefore for synthesis of compounds of formula I.

Alternatively, compounds of formula XVII may be prepared by reaction of a corresponding compound of formula I with a compound corresponding to a compound of formula XIX in which, in place of $R^7$, the group $R^b$ is present, in which $R^b$ is as hereinbefore defined, for example under conditions described above in respect of the preparation of compounds of formula Ia.

Compounds of formulae XV and XX may be prepared by reaction of a corresponding compound of formula X as hereinbefore defined with, respectively, a compound of formula XVI as hereinbefore defined, or a compound of formula XXI, $$R^{3b}CH_2NH_2 \qquad XXI$$

wherein $R^{3b}$ is as hereinbefore defined, for example under similar conditions to those described hereinbefore for synthesis of compounds of formula I.

Compounds of formula XVI, XVIII, XIX, XIXA, XIXB, XIXC, XIXD and XXI are either commercially available, are known in the literature, or may be obtained either by analogy with the processes described herein, or by conventional synthetic procedures, in accordance with standard techniques, from readily available starting materials using appropriate reagents and reaction conditions. For example, compounds of formulae XIXA and XIXB may be prepared by reaction of a corresponding compound of formula XIXC or XIXD (as appropriate) with a compound of formula X, for example under similar conditions to those described hereinbefore.

Compounds of formulae I and Ia, as defined above, and derivatives of either, are referred to hereinafter as "the compounds of the invention".

Preferred compounds of the invention thus include the compounds of the examples described hereinafter. In this respect, compounds of the invention that may be mentioned include:

Ph(3-Cl)(5-OCHF$_2$)—(R)CH(OH)C(O)-Aze-Pab;
Ph(3-Cl)(5-OCHF$_2$)—(R)CH(OH)C(O)-Aze-Pab(OMe);
Ph(3-Cl)(5-OCHF$_2$)—(R)CH(OH)C(O)-Aze-Pab(OEt);
Ph(3-Cl)(5-OCHF$_2$)—(R)CH(OH)C(O)-Aze-Pab(OnPr);
Ph(3-Cl)(5-OCHF$_2$)—(R)CH(OH)C(O)-Aze-Pab(OiPr);

Ph(3-Cl)(5-OCHF$_2$)—(R)CH(OH)C(O)-Aze-Pab(OcBu);
Ph(3-Cl)(5-OCHF$_2$)—(R)CH(OH)C(O)-Aze-Pab(OH);
Ph(3-Cl)(5-OCHF$_2$)—(R)CH(OH)C(O)-Aze-Pab(COOc-Pentyl);
Ph(3-Cl)(5-OCHF$_2$)—(R)CH(OH)C(O)-Aze-Pab(Z);
Ph(3-Cl)(5-OCF$_3$)—(R)CH(OH)C(O)-Aze-Pab;
Ph(3-Cl)(5-OCF$_3$)—(R)CH(OH)C(O)-Aze-Pab(OMe);
Ph(3-Cl)(5-OCF$_3$)—(R)CH(OH)C(O)-Aze-Pab(OCH$_2$-3-(5-Me-isoxazole));
Ph(3-Cl)(5-OCF$_3$)—(R)CH(OH)C(O)-Aze-Pab(OCH$_2$-3-pyridine);
Ph(3-Cl)(5-OCF$_3$)—(R)CH(OH)C(O)-Aze-Pab(OiBu);
Ph(3-Cl)(5-OCF$_3$)—(R)CH(OH)C(O)-Aze-Pab(OEt);
Ph(3-Cl)(5-OCF$_3$)—(R)CH(OH)C(O)-Aze-Pab(OBn);
Ph(3-Cl)(5-OCF$_3$)—(R)CH(OH)C(O)-Aze-Pab(OcHexyl);
Ph(3-Cl)(5-OCF$_3$)—(R)CH(OH)C(O)-Aze-Pab(OcBu);
Ph(3-Cl)(5-OCF$_3$)—(R)CH(OH)C(O)-Aze-Pab(OCH$_2$CH$_2$OPh(3-CF$_3$));
Ph(3-Cl)(5-OCF$_3$)—(R)CH(OH)C(O)-Aze-Pab(OBn(4-Cl));
Ph(3-Cl)(5-OCF$_3$)—(R)CH(OH)C(O)-Aze-Pab(OBn(3-MeO));
Ph(3-Cl)(5-OCF$_3$)—(R)CH(OH)C(O)-Aze-Pab(OBn(2-Br));
Ph(3-Cl)(5-OCF$_3$)—(R)CH(OH)C(O)-Aze-Pab(OBn(4-Me));
Ph(3-Cl)(5-OCF$_3$)—(R)CH(OH)C(O)-Aze-Pab(O-4-heptyl);
Ph(3-Cl)(5-OCHF$_2$)—(S)CH(CH$_2$OH)C(O)-Aze-Pab;
Ph(3-Cl)(5-OCF$_3$)—(S)CH(CH$_2$OH)C(O)-Aze-Pab;
Ph(3-Cl)(5-OCF$_3$)—(S)CH(CH$_2$OH)C(O)-Aze-Pab(OMe);
Ph(3-OCHF$_2$)—(R)CH(OH)C(O)-Aze-Pab;
Ph(3-OCF$_3$)—(R)CH(OH)C(O)-Aze-Pab;
Ph(3-Cl)(5-OCH$_2$CF$_3$)—(R)CH(OH)C(O)-Aze-Pab;
Ph(3-Cl)(5-OCH$_2$CF$_3$)—(R)CH(OH)C(O)-Aze-Pab(OMe);
Ph(3-Cl)(5-OCH$_2$CHF$_2$)—(R)CH(OH)C(O)-Aze-Pab;
Ph(3-Cl)(5-OCH$_2$CHF$_2$)—(R)CH(OH)C(O)-Aze-Pab(OMe);
Ph(3-Cl)(5-OCH$_2$F)—(R)CH(OH)C(O)-Aze-Pab;
Ph(3-Cl)(5-OCH$_2$F)—(R)CH(OH)C(O)-Aze-Pab(OMe);
Ph(3-Cl)(5-OCH$_2$CH$_2$F)—(R)CH(OH)C(O)-Aze-Pab;
Ph(3-Cl)(5-OCH$_2$CH$_2$F)—(R)CH(OH)C(O)-Aze-Pab(OMe);
Ph(3-Cl)(5-OCH(CH$_2$F)$_2$)—(R)CH(OH)C(O)-Aze-Pab;
Ph(3-Cl)(5-OCH(CH$_2$F)$_2$)—(R)CH(OH)C(O)-Aze-Pab(OMe);
Ph(3-F)(5-OCHF$_2$)—(R)CH(OH)C(O)-Aze-Pab;
Ph(3-F)(5-OCHF$_2$)—(R)CH(OH)C(O)-Aze-Pab(OMe);
Ph(3-Br)(5-OCH$_2$F)—(R)CH(OH)C(O)-Aze-Pab;
Ph(3-Br)(5-OCHF$_2$)—(R)CH(OH)C(O)-Aze-Pab;
Ph(3-Br)(5-OCHF$_2$)—(R)CH(OH)C(O)-Aze-Pab(OMe);
Ph(3-Cl, 5-OCH$_2$CHF$_2$)—(R)CH(OH)C(O)-Aze-Pab(OH);
Ph(3-Cl, 5-OCH$_2$CH$_2$F)—(R)CH(OH)C(O)-Aze-Pab(OH);
Ph(3-Cl, 5-OCHF$_2$)—(R)CH(OH)C(O)-Pro-Pab;
Ph(3-Cl, 5-OCHF$_2$)—(R)CH(OH)C(O)-Pro-Pab(OMe);
Ph(3-Cl, 5-OCHF$_2$)—(R)CH(OH)C(O)-Aze-NH—CH$_2$-((2-amidino)-5-pyridinyl);
Ph(3-Cl, 5-OCHF$_2$)—(R)CH(OH)C(O)-Aze-NH—CH$_2$-((2-methoxyamidino)-5-pyridinyl);
Ph(3-Cl, 5-OCHF$_2$)—(R)CH(OH)C(O)-Aze-NH—CH$_2$-((5-amidino)-2-pyrimidinyl);
Ph(3-Cl, 5-OCHF$_2$)—(R)CH(OH)C(O)-Aze-NH—CH$_2$-((5-methoxyamidino)-2-pyrimidinyl);
Ph(3-Cl, 5-OCHF$_2$)—(R)CH(OH)C(O)-Aze-Pab(3-F);
Ph(3-Cl, 5-OCHF$_2$)—(R)CH(OH)C(O)-Aze-Pab(2,6-diF);
Ph(3-Cl, 5-OCHF$_2$)—(R)CH(OH)C(O)-Aze-Pab(2,6-diF)(OMe);
Ph(3-Cl, 5-OCHF$_2$)—(R)CH(OH)C(O)-Aze-Pab(2,5-diF); and
Ph(3-Cl, 5-OCHF$_2$)—(R)CH(OH)C(O)-Aze-Pab(2,5-diF)(OMe).

The compounds of the invention may exhibit tautomerism. All tautomeric forms and mixtures thereof are included within the scope of the invention. Particular tautomeric forms that may be mentioned include those connected with the position of the double bond in the amidine functionality in a compound of formula Ia, and the position of the substituent $R^5$.

Compounds of the invention also contain two or more asymmetric carbon atoms and may therefore exhibit optical and/or diastereoisomerism. Diastereoisomers may be separated using conventional techniques, e.g. chromatography. The various stereoisomers may be isolated by separation of a racemic or other mixture of the compounds using conventional, e.g. HPLC techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

Compounds of the invention in which the

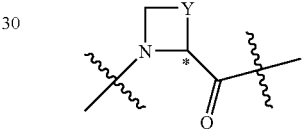

fragment is in the S-configuration are preferred.

Preferred compounds of the invention include those in which the structural fragment

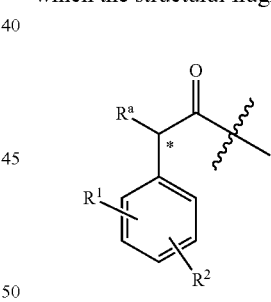

is in the R-configuration when $R^a$ represents —OH or is in the S-configuration when $R^a$ represents —CH$_2$OH.

The wavy lines on the bonds in the above two fragments signify the bond positions of the fragments.

Compounds of the invention that may be mentioned include Ph(3-Cl)(5-OCHF$_2$)—CH(OH)C(O)-Aze-Pab (wherein, on this occasion, Aze symbolises azetidine-2-carboxylate (i.e. in (R)— and/or (S)-conformations), as well as equivalent compounds in which, in place of a hydrogen atom in the amidino unit in Pab, the group —OR$^6$ (as hereinbefore defined) is present in which $R^6$ represents C$_{1-3}$ alkyl (i.e. Ph(3-Cl)(5-OCHF$_2$)—CH(OH)C(O)-Aze-Pab(OMe), Ph(3-Cl)(5-OCHF$_2$)—CH(OH)C(O)-Aze-Pab(OEt), Ph(3-Cl)(5-OCHF$_2$)—CH(OH)C(O)-Aze-Pab(OnPr) or Ph(3-Cl)(5-OCHF$_2$)—CH(OH)C(O)-Aze-Pab(OiPr)). Compounds of the invention that may further be mentioned include those that are not the specific compounds identified in the previous sentence.

It will be appreciated by those skilled in the art that in the processes described above and hereinafter the functional groups of intermediate compounds may need to be protected by protecting groups.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include $C_{1-6}$ alkyl or benzyl esters. Suitable protecting groups for amino and amidino include t-butyloxycarbonyl, benzyloxycarbonyl or 2-trimethylsilylethoxycarbonyl (Teoc). Amidino nitrogens may also be protected by hydroxy or alkoxy groups, and may be either mono- or diprotected.

The protection and deprotection of functional groups may take place before or after coupling, or before or after any other reaction in the above-mentioned schemes.

Protecting groups may be removed in accordance with techniques that are well known to those skilled in the art and as described hereinafter.

Persons skilled in the art will appreciate that, in order to obtain compounds of the invention in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", $3^{rd}$ edition, T. W. Greene & P. G. M. Wutz, Wiley-Interscience (1999).

Protected derivatives of compounds of the invention may be converted chemically to compounds of the invention using standard deprotection techniques (e.g. hydrogenation). The skilled person will also appreciate that certain compounds of formula Ia may also be referred to as being "protected derivatives" of compounds of formula I.

Medical and Pharmaceutical Use

Compounds of the invention may possess pharmacological activity as such. Compounds of the invention that may possess such activity include, but are not limited to, compounds of formula I.

However, other compounds of the invention (including compounds of formula Ia) may not possess such activity, but may be administered parenterally or orally, and may thereafter be metabolised in the body to form compounds that are pharmacologically active (including, but not limited to, corresponding compounds of formula I). Such compounds (which also includes compounds that may possess some pharmacological activity, but that activity is appreciably lower than that of the "active" compounds to which they are metabolised), may therefore be described as "prodrugs" of the active compounds.

Thus, the compounds of the invention are useful because they possess pharmacological activity, and/or are metabolised in the body following oral or parenteral administration to form compounds which possess pharmacological activity. The compounds of the invention are therefore indicated as pharmaceuticals.

According to a further aspect of the invention there is thus provided the compounds of the invention for use as pharmaceuticals.

In particular, compounds of the invention are potent inhibitors of thrombin either as such and/or (e.g. in the case of prodrugs), are metabolised following administration to form potent inhibitors of thrombin, for example as may be demonstrated in the tests described below.

By "prodrug of a thrombin inhibitor", we include compounds that form a thrombin inhibitor, in an experimentally-detectable amount, and within a predetermined time (e.g. about 1 hour), following oral or parenteral administration (see, for example, Test E below) or, alternatively, following incubation in the presence of liver microsomes (see, for example, Test G below).

The compounds of the invention are thus expected to be useful in those conditions where inhibition of thrombin is required, and/or conditions where anticoagulant therapy is indicated, including the following:

The treatment and/or prophylaxis of thrombosis and hypercoagulability in blood and/or tissues of animals including man. It is known that hypercoagulability may lead to thrombo-embolic diseases. Conditions associated with hypercoagulability and thrombo-embolic diseases which may be mentioned include inherited or acquired activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis, as well as coagulation syndromes (e.g. disseminated intravascular coagulation (DIC)) and vascular injury in general (e.g. due to surgery).

The treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis (e.g. DVT) and pulmonary embolism, arterial thrombosis (e.g. in myocardial infarction, unstable angina, thrombosis-based stroke and peripheral arterial thrombosis), and systemic embolism usually from the atrium during atrial fibrillation (e.g. non-valvular atrial fibrillation) or from the left ventricle after transmural myocardial infarction, or caused by congestive heart failure; prophylaxis of re-occlusion (i.e. thrombosis) after thrombolysis, percutaneous transluminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis; the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease and the formation of atherosclerotic plaques, cerebral arterial disease, cerebral infarction, cerebral thrombosis, cerebral embolism, peripheral arterial disease, ischaemia, angina (including unstable angina), reperfusion damage, restenosis after percutaneous trans-luminal angioplasty (PTA) and coronary artery bypass surgery.

Compounds of the invention that inhibit trypsin and/or thrombin may also be useful in the treatment of pancreatitis.

The compounds of the invention are thus indicated both in the therapeutic and/or prophylactic treatment of these conditions.

According to a further aspect of the present invention, there is provided a method of treatment of a condition where inhibition of thrombin is required which method comprises administration of a therapeutically effective amount of a compound of the invention to a person suffering from, or susceptible to, such a condition.

The compounds of the invention will normally be administered orally, intravenously, subcutaneously, buccally, rectally, dermally, nasally, tracheally, bronchially, by any other parenteral route or via inhalation, in the form of pharmaceutical preparations comprising compound of the invention either as a free base, or a pharmaceutically acceptable non-toxic organic or inorganic acid addition salt, in a pharmaceutically acceptable dosage form.

Preferred routes of administration of compounds of the invention are oral. Preferred pharmaceutical preparations include modified release pharmaceutical compositions comprising compounds of the invention. The term "modified release" pharmaceutical composition will be well understood by the skilled person to include any composition in which the onset and/or rate of release of drug (i.e. compound of the invention) is altered by galenic manipulations, and thus includes the definition provided in the *United States Pharmacopeia* (USP XXII) at pages xliii and xliv of the preface/preamble part, the relevant disclosure in which document is hereby incorporated by reference.

Suitable modified release formulations may thus be prepared by the skilled person in accordance with standard techniques in pharmacy (see, for example, *Pharmaceutisch Weekblad Scientific Edition*, 6, 57 (1984); *Medical Applications of Controlled Release*, Vol II, eds. Langer and Wise (1984) Bocaraton, Fla., at pages 1 to 34; *Industrial Aspects of Pharmaceuticals*, ed. Sandel, Swedish Pharmaceutical Press (1993) at pages 93 to 104; and pages 191 to 211 of "*Pharmaceutics: The Science of Dosage Form Design*", ed. M. E. Aulton (1988) (Churchill Livingstone)).

Preferred modified release formulations thus include those in which an appropriate compound of the invention is embedded in a polymer matrix. In this respect, we prefer that formulations including compounds of the invention are provided for oral administration in the form of a so-called "swelling" modified-release system, or a "gelling matrix" modified-release system, in which compound of the invention is provided together with a polymer that swells in an aqueous medium (i.e. a "hydrophilic gelling component").

In particular we prefer that the compounds of the invention are formulated together in a gelling matrix composition comprising iota-carrageenan and one or more neutral gelling polymers.

Iota-carrageenan is preferably present in such a preferred preparation at a level of more that 15% by weight. Preferred grades of iota-carrageenan include pharmaceutical grade iota-carrageenan (available from FMC Biopolymer), which has a viscosity of not less than 5 centipoise (cps), preferably in the range 5-10 cps (for a 1.5% solution warmed to 82° C., after which the viscosity is measured at 75° C. with a Brookfield LV viscometer fitted with a #1 spindle running at a speed of 30 rpm), and technical grade iota-carrageenan (available from Fluka Biochemica), which preferably has a viscosity of not less than 14 mPa·.s, for a 0.3% aqueous solution warmed to 20° C., after which the viscosity is measured using a fallingball viscometer, of type Haake, used together with a Lauda thermostat C3 and Hakke Mess-System III, and using gold-coated stainless steel balls of density 7.8 g/cm$^3$.

The neutral gelling polymer may be a single, or a mixture of more than one, neutral erodable polymer(s) having gelling properties and having substantially pH-independent solubility. The neutral gelling polymer is, preferably, present in the formulation at a level of more that 10% but preferably more than 20% by weight.

Suitable neutral gelling polymers include polyethylene oxide (PEO), derivatives and members of the PEO family (for example, polyethylene glycol (PEG), preferably existing naturally in the solid state, of suitable molecular weight or viscosity). If used as a single neutral gelling polymer, a PEO preferably has a MW of $\geq$4 million (4M), corresponding to an aqueous solution viscosity range of 1650-5500 mPa·.s (or 1650-5500 cps; measured for a 1% aqueous solution at 25° C., using a Brookfield RVF viscometer, with No. 2 spindle, at 2 rpm). Other examples of suitable PEOs include a PEO of MW around 5 million (5M), corresponding to an aqueous solution viscosity range of 5500-7500 mPa·s, or a PEO MW around 8 million (8M), corresponding to an aqueous solution viscosity range of 10000-15000 mPa·s. This range covers the value for typical solution viscosity (in cps) measured at 25° C., quoted for this polymer, in the USP 24/NF 19, 2000 edition, pp. 2285-2286. If PEG is used as a single neutral is gelling polymer it preferably has a high molecular weight, for example, a MW of around 20000, corresponding to a viscosity range of 2700-3500 mPa·s (or 2700-3500 cps), measured using a 50% aqueous solution (w/w) at 20° C., using a capillary viscometer (Ubbelohde or equivalent). [Ref: European Pharmacopoeia 3$^{rd}$ Ed., 2000, Supplement, pp. 908-909.]

Other suitable gelling polymers include cellulose derivatives such as hydroxypropylmethyl cellulose (HPMC) or hydroxyethylcellulose (HEC) with suitably high viscosities (for example "HPMC 10000 cps", "HPMC 15000 cps", "HEC type HH" or "HEC type H"). When used as a single neutral polymer, hydroxypropylmethyl cellulose polymers like "HPMC 10000 cps" and "HPMC 15000 cps" have, respectively, apparent viscosities of 7500-14000 mPa·s (or 7500-14000 cps), and 11250-21000 mPa·s (or 11250-21000 cps), when measured at 20° C. with a 2% (w/w) aqueous solution, calculated with reference to the dried substance, using a capillary viscometer (Ubbelohde or equivalent). One type of hydroxyethylcellulose polymer, for example, "Natrosol 250 Pharma, type HH", from Hercules Incorporated (Aqualon), shows typically a Brookfield viscosity of about 20,000 mPa·s using a Brookfield Synchro-Lectric Model LVF instrument, at the conditions 1% solution concentration, spindle no. 4, spindle speed 30 rpm, factor 200, 25° C. (See Natrosol Physical and Chemical Properties booklet, 33.007-E6 (1993), p. 21).

Particular formulations that may be mentioned include those in which compound of the invention is formulated together with iota-carageenan and HPMC (10,000 cps) in a 50:50 (wt %) ratio, or together with iota-carageenan and PEO 4M in a 50:50 (wt %) ratio.

Preferred additional excipients in such formulations include lubricants, such as sodium stearyl fumarate.

Depending upon the disorder and patient to be treated and the route of administration, the compositions may be administered at varying doses.

The compounds of the invention may also be combined and/or co-administered with any antithrombotic agent(s) with a different mechanism of action, such as one or more of the following: the antiplatelet agents acetylsalicylic acid, ticlopidine and clopidogrel; thromboxane receptor and/or synthetase inhibitors; fibrinogen receptor antagonists; prostacyclin mimetics; phosphodiesterase inhibitors; ADP-receptor ($P_2T$) antagonists; and inhibitors of carboxypeptidase U (CPU).

The compounds of the invention may further be combined and/or co-administered with thrombolytics such as one or more of tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

According to a further aspect of the invention there is thus provided a pharmaceutical formulation including a compound of the invention, in admixture with a pharmaceutically acceptable adjuvant, diluent or carrier.

Suitable daily doses of the compounds of the invention in therapeutic treatment of humans are about 0.001-100 mg/kg body weight at peroral administration and 0.001-50 mg/kg body weight at parenteral administration.

For the avoidance of doubt, as used herein, the term "treatment" includes therapeutic and/or prophylactic treatment.

Compounds of the invention have the advantage that they may be more efficacious, be less toxic, be longer acting, have a broader range of activity, be more potent, produce fewer side effects, be more easily absorbed, and/or have a better pharmacokinetic profile (e.g. higher oral bioavailability and/or lower clearance), than, and/or have other useful pharmacological, physical, or chemical, properties over, compounds known in the prior art. Compounds of the invention may have the further advantage that they may be administered less frequently than compounds known in the prior art.

Biological Tests

The following test procedures may be employed.

Test A

Determination of Thrombin Clotting Time (TT)

The inhibitor solution (25 μL) is incubated with plasma (25 μL) for three minutes. Human thrombin (T 6769; Sigma Chem. Co or Hematologic Technologies) in buffer solution, pH 7.4 (25 μL, 4.0 NIH units/mL), is then added and the clotting time measured in an automatic device (KC 10; Amelung).

The thrombin clotting time (TT) is expressed as absolute values (seconds) as well as the ratio of TT without inhibitor ($TT_0$) to TT with inhibitor ($TT_i$). The latter ratios (range 1-0) are plotted against the concentration of inhibitor (log transformed) and fitted to sigmoidal dose-response curves according to the equation $$y=a/[1+(x/IC_{50})^s]$$

where: a=maximum range, i.e. 1; s=slope of the dose-response curve; and $IC_{50}$=the concentration of inhibitor that doubles the clotting time. The calculations are processed on a PC using the software program GraFit Version 3, setting equation equal to: Start at 0, define end=1 (Erithacus Software, Robin Leatherbarrow, Imperial College of Science, London, UK).

Test B

Determination of Thrombin Inhibition with a Chromogenic, Robotic Assay

The thrombin inhibitor potency is measured with a chromogenic substrate method, in a Plato 3300 robotic microplate processor (Rosys AG, CH-8634 Hombrechtikon, Switzerland), using 96-well, half volume microtitre plates (Costar, Cambridge, Mass., USA; Cat No 3690). Stock solutions of test substance in DMSO (72 μL), 0.1-1 mmol/L, are diluted serially 1:3 (24+48 μL) with DMSO to obtain ten different concentrations, which are analysed as samples in the assay. 2 μL of test sample is diluted with 124 μL assay buffer, 12 μL of chromogenic substrate solution (S-2366, Chromogenix, Mölndal, Sweden) in assay buffer and finally 12 μL of α-thrombin solution (Human α-thrombin, Sigma Chemical Co. or Hematologic Technologies) in assay buffer, are added, and the samples mixed. The final assay concentrations are: test substance 0.00068-13.3 μmol/L, S-2366 0.30 mmol/L, α-thrombin 0.020 NIHU/mL. The linear absorbance increment during 40 minutes incubation at 37° C. is used for calculation of percentage inhibition for the test samples, as compared to blanks without inhibitor. The $IC_{50}$-robotic value, corresponding to the inhibitor concentration which causes 50% inhibition of to the thrombin activity, is calculated from a log concentration vs. % inhibition curve.

Test C

Determination of the Inhibition Constant $K_i$ for Human Thrombin $K_i$-determinations are made using a chromogenic substrate method, performed at 37° C. on a Cobas Bio centrifugal analyser (Roche, Basel, Switzerland). Residual enzyme activity after incubation of human α-thrombin with various concentrations of test compound is determined at three different substrate concentrations, and is measured as the change in optical absorbance at 405 nm.

Test compound solutions (100 μL; normally in buffer or saline containing BSA 10 g/L) are mixed with 200 μL of human α-thrombin (Sigma Chemical Co) in assay buffer (0.05 mol/L Tris-HCl pH 7.4, ionic strength 0.15 adjusted with NaCl) containing BSA (10 g/L), and analysed as samples in the Cobas Bio. A 60 μL sample, together with 20 μL of water, is added to 320 μL of the substrate S-2238 (Chromogenix AB, Mölndal, Sweden) in assay buffer, and the absorbance change (ΔA/min) is monitored. The final concentrations of S-2238 are 16, 24 and 50 μmol/L and of thrombin 0.125 NIH U/mL.

The steady state reaction rate is used to construct Dixon plots, i.e. diagrams of inhibitor concentration vs. 1/(ΔA/min). For reversible, competitive inhibitors, the data points for the different substrate concentrations typically form straight lines which intercept at $x=-K_i$.

Test D

Determination of Activated Partial Thromboplastin Time (APTT)

APTT is determined in pooled normal human citrated plasma with the reagent PTT Automated 5 manufactured by Stago. The inhibitors are added to the plasma (10 μL inhibitor solution to 90 μL plasma) and incubated with the APTT reagent for 3 minutes followed by the addition of 100 μL of calcium chloride solution (0.025 M) and APTT is determined by use of the coagulation analyser. KC10 (Amelung) according to the instructions of the reagent producer.

The clotting time is expressed as absolute values (seconds) as well as the ratio of APTT without inhibitor ($APTT_0$) to APTT with inhibitor ($APTT_i$). The latter ratios (range 1-0) are plotted against the concentration of inhibitor (log transformed) and fitted to sigmoidal dose-response curves according to the equation $$y=a/[1+(x/IC_{50})^s]$$

where: a=maximum range, i.e. 1; s=slope of the dose-response curve; and $IC_{50}$=the concentration of inhibitor that doubles the clotting time. The calculations are processed on a PC using the software program GraFit Version 3, setting equation equal to: Start at 0, define end=1 (Erithacus Software, Robin Leatherbarrow, Imperial College of Science, London, UK). $IC_{50}$APTT is defined as the concentration of inhibitor in human plasma that doubled the Activated Partial Thromboplastin Time.

Test E

Determination of Thrombin Time Ex Vivo

The inhibition of thrombin after oral or parenteral administration of the compounds of the invention, dissolved in ethanol:SolutolK:water (5:5:90), is examined in conscious rats which, one or two days prior to the experiment, are equipped with a catheter for blood sampling from the carotid artery. On the experimental day blood samples are withdrawn at fixed times after the administration of the compound into plastic tubes containing 1 part sodium citrate solution (0.13 mol per L) and 9 parts of blood. The tubes are centrifuged to obtain platelet poor plasma.

50 µL of plasma samples are precipitated with 100 µL of cold acetonitrile. The samples are centrifuged for 10 minutes at 4000 rpm. 75 µL of the supernatant is diluted with 75 µL of 0.2% formic acid. 10 µL volumes of the resulting solutions are analysed by LC-MS/MS and the concentrations of thrombin inhibitor are determined using standard curves.

Test F

Determination of Plasma Clearance in Rat

Plasma clearance is estimated in male Sprague Dawley rats. The compound is dissolved in water and administered as a subcutaneous bolus injection at a dose of 4 µmol/kg. Blood samples are collected at frequent intervals up to 5 hours after drug administration. Blood samples are centrifuged and plasma is separated from the blood cells and transferred to vials containing citrate (10% final concentration). 50 µL of plasma samples are precipitated with 100 µL of cold acetonitrile. The samples are centrifuged for 10 minutes at 4000 rpm. 75 µL of the supernatant is diluted with 75 µL of 0.2% formic acid. 10 µL volumes of the resulting solutions are analysed by LC-MS/MS and the concentrations of thrombin inhibitor are determined using standard curves. The area under the plasma concentration-time profile is estimated using the log/linear trapezoidal rule and extrapolated to infinite time. Plasma clearance (CL) of the compound is then determined as $$CL=Dose/AUC$$

The values are reported in mL/min/kg.

Test G

Determination of In Vitro Stability

Liver microsomes are prepared from Sprague-Dawley rats and human liver samples according to internal SOPs. The compounds are incubated at 37° C. at a total microsome protein concentration of 3 mg/mL in a 0.05 mol/L TRIS buffer at pH 7.4, in the presence of the cofactors NADH (2.5 mmol/L) and NADPH (0.8 mmol/L). The initial concentration of compound is 5 or 10 µmol/L. Samples are taken for analysis up to 60 minutes after the start of the incubation. The enzymatic activity in the collected sample is immediately stopped by adding 20% myristic acid at a volume corresponding to 3.3% of the total sample volume. The concentration of compound remaining (FINAL CONC) in the 60 min. sample is determined by means of LCMS using a sample collected at zero time as reference (START CONC). The % of degraded thrombin inhibitor is calculated as:

$$100\% \times \frac{[\text{START } CONC] - [\text{FINAL } CONC]}{[\text{START } CONC]}$$

Test H

Arterial Thrombosis Model

Vessel damage is induced by applying ferric chloride ($FeCl_3$) topically to the carotid artery. Rats are anaesthetised with an intraperitoneal injection of sodium pentobarbital (80 mg/kg; Apoteksbolaget; Umeå, Sweden), followed by continuous infusion (12 mg/kg/h) throughout the experiment. Rat body temperature is maintained at 38° C. throughout the experiment by external heating. The experiment starts with a 5 minutes control period. Five minutes later, human $^{125}$I-fibrinogen (80 kBq; IM53; Amersham International, Buckinghamshire, UK) is given intravenously and is used as a marker for the subsequent incorporation of fibrin(ogen) into the thrombus. The proximal end of the carotid artery segment is placed in a plastic tube (6 mm; Silastic®; Dow Corning, Mich., USA) opened lengthways, containing $FeCl_3$-soaked (2 µL; 55% w/w; Merck, Darmstadt, Germany) filter paper (diameter 3 mm; IF; Munktell, Grycksbo, Sweden). The left carotid artery is exposed to $FeCl_3$ for 10 minutes and is then removed from the plastic tube and soaked in saline. Fifty minutes later, the carotid artery is removed and rinsed in saline. Reference blood samples are also taken for determination of blood $^{125}$I-activity, 10 minutes after the injection of $^{121}$I-fibrinogen, and at the end of the experiment. The $^{125}$I-activity in the reference blood samples and the vessel segment are measured in a gamma counter (1282 Compugamma; LKB Wallac Oy, Turku, Finland) on the same day as the experiment is performed. The thrombus size is determined as the amount of $^{125}$I-activity incorporated in the vessel segment in relation to the $^{125}$I-activity in the blood (cpm/mg).

GENERAL EXPERIMENTAL DETAILS

TLC was performed on silica gel. Chiral HPLC analysis was performed using a 46 mm×250 mm Chiralcel OD column with a 5 cm guard column. The column temperature was maintained at 35° C. A flow rate of 1.0 mL/min was used. A Gilson 115 UV detector at 228 nm was used. The mobile phase consisted of hexanes, ethanol and trifluoroacetic acid and the appropriate ratios are listed for each compound. Typically, the product was dissolved in a minimal amount of ethanol and this was diluted with the mobile phase.

LC-MS/MS was performed using a HP-1100 instrument equipped with a CTC-PAL injector and a 5 µm, 4×100 mm ThermoQuest, Hypersil BDS-C18 column. An API-3000 (Sciex) MS detector was used. The flow rate was 1.2 mL/min and the mobile phase (gradient) consisted of 10-90% acetonitrile with 90-10% of 4 mM aq. ammonium acetate, both containing 0.2% formic acid.

¹H NMR spectra were recorded using tetramethylsilane as the internal standard. ¹³C NMR spectra were recorded using the listed deuterated solvents as the internal standard.

EXAMPLE 1

Ph(3-Cl)(5-OCHF$_2$)—(R)CH(OH)C(O)-Aze-Pab (OcBu)

(i) 3-Chloro-5-methoxybenzaldehyde 3,5-Dichloroanisole (74.0 g, 419 mmol) in THF (200 mL) was added dropwise to magnesium metal (14.2 g, 585 mmol, pre-washed with 0.5 N HCl) in THF (100 mL) at 25° C. After the addition, 1,2-dibromoethane (3.9 g, 20.8 mmol) was added dropwise. The resultant dark brown mixture was heated at reflux for 3 h. The mixture was cooled to 0° C., and N,N-dimethylformamide (60 mL) was added in one portion. The mixture was partitioned with diethyl ether (3× 400 mL) and 6N HCl (500 mL). The combined organic extracts were washed with brine (300 mL), dried (Na$_2$SO$_4$), filtered and concentrated in vacuo to give an oil. Flash chromatography (2×) on silica gel eluting with Hex:EtOAc (4:1) afforded the sub-title compound (38.9 g, 54%) as a yellow oil.

¹H NMR (300 MHz, CDCl$_3$) δ 9.90 (s, 1H), 7.53 (s, 1H), 7.38 (s, 1H), 7.15 (s, 1H), 3.87 (s, 3H).

(ii) 3-Chloro-5-hydroxybenzaldehyde

A solution of 3-chloro-5-methoxybenzaldehyde (22.8 g, 134 mmol; see step (i) above) in CH$_2$Cl$_2$ (250 mL) was cooled to 0° C. Boron tribromide (15.8 mL, 167 mmol) was added dropwise over 15 min. After stirring, the reaction mixture for 2 h, H$_2$O (50 mL) was added slowly. The solution was then extracted with Et$_2$O (2× 100 mL). The organic layers were combined, dried (Na$_2$SO$_4$), filtered and concentrated in vacuo. Flash chromatography on silica gel eluting with Hex: EtOAc (4:1) afforded the sub-title compound (5.2 g, 25%).

¹H NMR (300 MHz, CDCl$_3$) δ 9.85 (s, 1H), 7.35 (s, 1H), 7.20 (s, 1H), 7.10 (s, 1H), 3.68 (s, 1H)

(iii) 3-Chloro-5-difluoromethoxybenzaldehyde

A solution of 3-chloro-5-hydroxybenzaldehyde (7.5 g, 48 mmol; see step (ii) above) in 2-propanol (250 mL) and 30% KOH (100 mL) was heated to reflux. While stirring, CHClF$_2$ was bubbled into the reaction mixture for 2 h. The reaction mixture was cooled, acidified with 1N HCl and extracted with EtOAc (2× 100 mL). The organics were washed with brine (100 mL), dried (Na$_2$SO$_4$), filtered and concentrated in vacuo. Flash chromatography on silica gel eluting with Hex:EtOAc (4:1) afforded the sub-title compound (4.6 g, 46%).

¹H NMR (300 MHz, CDCl$_3$) δ 9.95 (s, 1H), 7.72 (s, 1H), 7.52 (s, 1H), 7.40 (s, 1H), 6.60 (t, J$_{H-F}$=71.1 Hz, 1H)

(iv) Ph(3-Cl)(5-OCHF$_2$)—(R,S)CH(OTMS)CN

A solution of 3-chloro-5-difluoromethoxybenzaldehyde (4.6 g, 22.3 mmol; see step (iii) above) in CH$_2$Cl$_2$ (200 mL) was cooled to 0° C. ZnI$_2$ (1.8 g, 5.6 mmol) and trimethylsilyl cyanide (2.8 g, 27.9 mmol) were added and the reaction mixture was allowed to warm to room temperature and stirred for 15 h. The mixture was partially concentrated in vacuo yielding the sub-title compound as a liquid, which was used directly in step (v) below without further purification or characterization.

(v) Ph(3-Cl)(5-OCHF$_2$)—(R,S)CH(OH)C(NH)OEt

Ph(3-Cl)(5-OCHF$_2$)—(R,S)CH(OTMS)CN (6.82 g, assume 22.3 mmol; see step (iv) above) was added dropwise to HCl/EtOH (500 mL). The reaction mixture was stirred 15 h, then partially concentrated in vacuo yielding the sub-title compound as a liquid, which was used in step (vi) without further purification or characterization.

(vi) Ph(3-Cl)(5-OCHF$_2$)—(R,S)CH(OH)C(O)OEt

Ph(3-Cl)(5-OCHF$_2$)—(R,S)CH(OH)C(NH)OEt (6.24 g, assume 22.3 mmol; see step (v) above) was dissolved in THF (250 mL), 0.5M H$_2$SO$_4$ (400 mL) was added and the reaction was stirred at 40° C. for 65 h, cooled and then partially concentrated in vacuo to remove most of the THF. The reaction mixture was then extracted with Et$_2$O (3× 100 mL), dried (Na$_2$SO$_4$), filtered and concentrated in vacuo to afford the sub-title compound as a solid, which was used in step (vii) without further purification or characterization.

(vii) Ph(3-Cl)(5-OCHF$_2$)—(R,S)CH(OH)C(O)OH

A solution of Ph(3-Cl)(5-OCHF$_2$)—(R,S)CH(OH)C(O) OEt (6.25 g, assume 22.3 mmol; see step (vi) above) in 2-propanol (175 mL) and 20% KOH (350 mL) was stirred at room temperature 15 h. The reaction was then partially concentrated in vacuo to remove most of the 2-propanol. The remaining mixture was acidified with 1M H$_2$SO$_4$, extracted with Et$_2$O (3× 100 mL), dried (Na$_2$SO$_4$) and concentrated in vacuo to give a solid. Flash chromatography on silica gel eluting with CHCl$_3$:MeOH:concentrated NH$_4$OH (6:3:1) afforded the ammonium salt of the sub-title compound. The ammonium salt was then dissolved in a mixture of EtOAc (75 mL) and H$_2$O (75 mL) and acidified with 2N HCl. The organic layer was separated and washed with brine (50 mL), dried (Na$_2$SO$_4$) and concentrated in vacuo to afford the sub-title compound (3.2 g, 57% from steps (iv) to (vii)).

¹H NMR (300 MHz, CD$_3$OD) δ 7.38 (s, 1H), 7.22 (s, 1H), 7.15 (s, 1H), 6.89 (t, J$_{H-F}$=71.1 Hz, 1H), 5.16 (s, 1H)

(viii) Ph(3-Cl)(5-OCHF$_2$)—(R)CH(OH)C(O)OH (a) and Ph(3-Cl)(5-OCHF$_2$) (S)CH(OAc)C(O)OH (b)

A mixture of Ph(3-Cl)(5-OCHF$_2$)—(R,S)CH(OH)C(O) OH (3.2 g, 12.7 mmol; see step (vii) above) and Lipase PS "Amano" (~2.0 g) in vinyl acetate (125 mL) and MTBE (125 mL) was heated at reflux for 48 h. The reaction mixture was cooled, filtered through Celite® and the filter cake washed with EtOAc. The filtrate was concentrated in vacuo and subjected to flash chromatography on silica gel eluting with CHCl$_3$:MeOH:concentrated NH$_4$OH (6:3:1) yielding the ammonium salts of the sub-title compounds (a) and (b). Compound (a) as a salt was dissolved in H$_2$O, acidified with 2N HCl and extracted with EtOAc. The organic layer was washed with brine, dried (Na$_2$SO$_4$), filtered and concentrated in vacuo to afford the sub-title compound (a) (1.2 g, 37%).

For sub-title compound (a)

¹H NMR (300 MHz, CD$_3$OD) δ 7.38 (s, 1H), 7.22 (s, 1H), 7.15 (s, 1H), 6.89 (t, J$_{H-F13\ 32\ 71.1}$ Hz, 1H), 5.17 (s, 1H)

(ix) Ph(3-Cl)(5-OCHF$_2$)—(R)CH(OH)C(O)-Aze-Pab(Teoc)

To a solution of Ph(3-Cl)(5-OCHF$_2$)—(R)CH(OH)C(O) OH (1.1 g, 4.4 mmol; see step (viii) above) and H-Aze-Pab (Teoc) (see international patent application WO 00/42059, 2.6 g, 5.7 mmol) in DMF (50 mL) at 0° C. was added PyBOP (2.8 g, 5.3 mmol) and collidine (1.3 g, 10.6 mmol). The reaction was stirred at 0° C. for 2 h and then at room temperature for an additional 15 h. The reaction mixture was concentrated in vacuo and flash chromatographed on silica gel (3×), eluting first with CHCl$_3$:EtOH (9:1), then with EtOAc:EtOH (20:1) and finally eluting with CH$_2$Cl$_2$:CH$_3$OH (95:5) to afford the sub-title compound (1.0 g, 37%) as a white solid.

$^1$H NMR (300 MHz, CD$_3$OD, mixture of rotamers) δ 7.79-7.85 (d, J=8.7 Hz, 2H), 7.15-7.48 (m, 5H), 6.89 and 6.91 (t, J$_{H-F}$=71.1 Hz, 1H), 5.12 and 5.20 (s, 1H), 4.75-4.85 (m, 1H), 3.97-4.55 (m, 6H), 2.10-2.75 (m, 2H), 1.05-1.15 (m, 2H), 0.09 (s, 9H)

MS (m/z) 611 (M+1)$^+$ (x) Ph(3-Cl)(5-OCHF$_2$)—(R)CH(OH)C(O)-Aze-Pab (OcBu, Teoc)

Ph(3-Cl)(5-OCHF$_2$)—(R)CH(OH)C(O)-Aze-Pab(Teoc) (0.051 g, 0.08 mmol; see step (ix) above), was dissolved in 3 mL of acetonitrile and 0.062 g (0.5 mmol) of O-cyclobutyl-hydroxylamine hydrochloride was added. The mixture was heated at 70° C. for 4.5 h. The solvent was evaporated and the residue was partitioned between water and ethyl acetate. The aqueous phase was extracted two more times with ethyl acetate and the combined organic phase was washed with water, brine, dried (Na$_2$SO$_4$), filtered and evaporated. Yield: 0.054 g (95%).

$^1$H-NMR (400 MHz; CD$_3$OD): δ 8.66-8.50 (m, 1H), 7.45 (d, 2H), 7.29 (m, 3H), 7.15 (m, 2H), 6.88 (t, 1H major rotamer), 6.85 (t, 1H minor rotamer), 5.18 (s, 1H major rotamer), 5.12 (s, 1H minor rotamer), 5.16 (m, 1H minor rotamer), 4.78 (m, 1H major rotamer), 4.70 (m, 1H), 4.50-4.30 (m, 3H), 4.19-3.93 (m, 3H), 2.71-2.44 (m, 1H), 2.34-2.11 (m, 5H), 1.78 (m, 1H), 1.62 (m, 1H), 0.96 (m, 2H), 0.01 (s, 9H)

(xi) Ph(3-Cl)(5-OCHF$_2$)—(R)CH(OH)C(O)-Aze-Pab(OcBu)

Ph(3-Cl)(5-OCHF$_2$)—(R)CH(OH)C(O)-Aze-Pab(OcBu, Teoc) (0.054 g, 0.08 mmol; see step (x) above), was dissolved in 0.5 mL of CH$_2$Cl$_2$ and 3 mL of TFA. The reaction was allowed to proceed for 60 minutes. TFA was evaporated and the residue was purified using preparative HPLC. The fractions of interest were pooled and freeze-dried (2×), yielding 23 mg (54%) of the title compound.

MS (m/z) 536 (M−1)$^-$; 538 (M+1)$^+$ $^1$H-NMR (400 MHz; CD$_3$OD): δ 7.56 (d, 2H), 7.33 (m, 3H), 7.15 (m, 2H), 6.89 (t, 1H major rotamer), 6.86 (t, 1H minor rotamer), 5.18 (s, 1H major rotamer; and m, 1H minor rotamer), 5.11 (s, 1H minor rotamer), 4.77 (m, 1H major rotamer), 4.58 (m, 1H), 4.42 (m, 2H), 4.34 (m, 1H major rotamer), 4.15 (m, 1H major rotamer), 4.06 (m, 1H minor rotamer), 3.97 (m, 1H minor rotamer), 2.66 (m, 1H minor rotamer), 2.52 (m, 1H major rotamer), 2.33-2.25 (m, 3H), 2.01-2.20 (m, 2H), 1.75 (m, 1H), 1.59 (m, 1H)

$^{13}$C-NMR (100 MHz; CD$_3$OD) (carbonyl and/or amidine carbons, rotamers) δ 172.4, 172.3, 171.9, 171.4, 152.3

EXAMPLE 2

Ph(3-Cl)(5-OCHF$_2$)—(R)CH(OH)C(O)-Aze-Pab (OH)

(i) Ph(3-Cl)(5-OCHF$_2$)—(R)CH(OH)C(O)-Aze-Pab (OH, Teoc)

Ph(3-Cl)(5-OCHF$_2$)—(R)CH(OH)C(O)-Aze-Pab(Teoc) (0.148 g, 0.24 mmol; see Example I(ix) above), was dissolved in 9 mL of acetonitrile and 0.101 g (1.45 mmol) of hydroxylamine hydrochloride was added. The mixture was heated at 70° C. for 2.5 h, filtered through Celite® and evaporated. The crude product (0.145 g; 75% pure) was used directly in the next step without further purification.

(ii) Ph(3-Cl)(5-OCHF$_2$)—(R)CH(OH)C(O)-Aze-Pab (OH)

Ph(3-Cl)(5-OCHF$_2$)—(R)CH(OH)C(O)-Aze-Pab(OH, Teoc) (0.145 g, 0.23 mmol; see step (i) above), was dissolved in 0.5 mL of CH$_2$Cl$_2$ and 9 mL of TFA. The reaction was allowed to proceed for 60 minutes. TFA was evaporated and the residue was purified using preparative HPLC. The fractions of interest were pooled and freeze-dried (2×), yielding 72 mg (yield over two steps 62%) of the title compound.

MS (m/z) 482 (M−1)$^-$; 484 (M+1)$^+$ $^1$H-NMR (400 MHz; CD$_3$OD): δ 7.58 (d, 2H), 7.33 (m, 3H), 7.15 (m, 2H), 6.89 (t, 1H major rotamer), 6.86 (t, 1H minor rotamer), 5.18 (s, 1H major rotamer; and m, 1H minor rotamer), 5.12 (s, 1H minor rotamer), 4.77 (m, 1H major rotamer), 4.42 (m, 2H), 4.34 (m, 1H major rotamer), 4.14 (m, 1H major rotamer), 4.06 (m, 1H minor rotamer), 3.95 (m, 1H minor rotamer), 2.66 (m, 1H minor rotamer), 2.50 (m, 1H major rotamer), 2.27 (m, 1H major rotamer), 2.14 (m, 1H minor rotamer)

$^{13}$C-NMR (100 MHz; CD$_3$OD): (carbonyl and/or amidine carbons, rotamers) δ 172.4, 172.3, 172.0, 171.4 152.3, 152.1

EXAMPLE 3

Ph(3-Cl)(5-OCHF$_2$)—(R)CH(OH)C(O)-Aze-Pab

Ph(3-Cl)(5-OCHF$_2$)—(R)CH(OH)C(O)-Aze-Pab(Teoc) (0.045 g, 0.074 mmol; see Example 1(ix) above), was dissolved in 3' mL of TFA and allowed to react for 1 h. TFA was evaporated and the residue was freeze dried from water/acetonitrile to yield 0.043 g (100%) of the sub-title compound as its TFA salt.

$^1$H-NMR (400 MHz; CD$_3$OD) rotamers: δ 7.8-7.75 (m, 2H), 7.55-7.5 (m, 2H), 7.35 (m, 1H, major rotamer), 7.31 (m, 1H, minor rotamer), 7.19 (m, 1H, major rotamer), 7.15 (m, 1H), 7.12 (m, 1H, minor rotamer), 6.89 (t, 1H, major rotamer), 6.87 (t, 1H, minor rotamer), 5.22 (m, 1H, minor rotamer), 5.20 (s, 1H, major rotamer), 5.13 (s, 1H, minor rotamer), 4.80 (m, 1H, major rotamer), 4.6-4.4 (m, 2H), 4.37 (m, 1H, major rotamer), 4.19 (m, 1H, major rotamer), 4.07 (m, 1H, minor rotamer), 3.98 (m, 1H, minor rotamer), 2.70 (m, 1H, minor rotamer), 2.55 (m, 1H, major rotamer), 2.29 (m, 1H, major rotamer), 2.15 (m, 1H, minor rotamer)

$^{13}$C-NMR (100 MHz; CD$_3$OD): (carbonyl and/or amidine carbons, rotamers) δ 172.6, 172.5, 172.0, 171.7, 167.0

MS (m/z) 465 (M−1)$^-$, 467 (M+1)$^+$

EXAMPLE 4

Ph(3-Cl)(5-OCHF$_2$)—(R)CH(OH)C(O)-Aze-Pab (COOcPentyl)

To a solution of Ph(3-Cl)(5-OCHF$_2$)—(R)CH(OH)C(O)-Aze-Pab×TFA (74 mg, 0.13 mmol; see Example 3 above) and cyclopentylchloroformate (44 mg, 0.30 mmol) in methylene chloride (5 mL) was added aq. NaOH (0.5 mL, 2M, 1 mmol). The mixture was stirred at room temperature and the reaction was monitored with HPLC. After 2.5 hours, water was added and the liquid phases were separated. The aqueous phase was extracted twice with methylene chloride. The combined organic phases were dried (MgSO$_4$) and purified on silica gel (first methylene chloride, then EtOAc). After removal of the solvents in vacuo, the solid residue was dissolved in water/acetonitrile and freeze-dried to afford the title compound as a white solid. Yield: 33 mg (44%)

MS (m/z) 579 (M+1)$^+$ $^1$H NMR (400 MHz; CD$_3$OD): δ 7.79 (d, 2H), 7.43-7.30 (m, 5H), 7.20-7.11 (m, 2H), 6.90 (t, 1H, major rotamer), 6.87 (t, 1H, minor rotamer), 5.19 (dd, 1H, minor rotamer), 5.18 (s, 1H, major rotamer), 5.13 (m, 1H), 5.11 (s, 1H, minor rotamer), 4.78 (dd, 1H, major rotamer), 4.45 (m, 2H), 4.35 (m, 1H, major rotamer), 4.16 (s, 1H, major rotamer), 4.06 (s, 1H, minor rotamer), 3.97 (s, 1H, minor rotamer), 2.68 (m, 1H, minor rotamer), 2.52 (s, 1H, major rotamer), 2.28 (s, 1H, major rotamer), 2.16 (s, 1H, minor rotamer), 1.90 (m, 2H), 1.77 (m, 4H), 1.61 (m, 2H)

$^{13}$C NMR (carbonyl and/or amidine protons; 100 MHz): δ 173.6, 173.1, 172.6, 170.3, 165.6

EXAMPLE 5

Ph(3-Cl)(5-OCHF$_2$)—(R)CH(OH)C(O)-Aze-Pab(Z)

The title compound was prepared according to the procedure described in Example 4 above starting from Ph(3-Cl)(5-OCHF$_2$)—(R)CH(OH)C(O)-Aze-Pab×TFA (73 mg, 0.13 mmol; see Example 3 above) and benzylchloroformate (35 mg, 0.21 mmol). Additional purification by reverse-phase HPLC (0.1M ammonium acetate/MeCN 40/60) was necessary. The appropriate fractions were concentrated in vacuo and extracted with EtOAc. Yield: 24 mg (32%).

MS (m/z) 602 (M+1)$^+$ $^1$H NMR (400 MHz; CD$_3$OD): δ 7.80 (d, 2H), 7.43-7.25 (m, 8H), 7.20-7.10 (m, 2H), 6.90 (t, 1H, major rotamer), 6.88 (t, 1H, minor rotamer), 5.18 (dd, 1H, minor rotamer), 5.18 (s, 2H), 5.17 (s, 1H, rotamer), 5.11 (s, 1H, rotamer), 4.78 (dd, 1H, major rotamer), 4.45 (m, 2H), 4.34 (m, 1H, major rotamer), 4.15 (s, 1H, major rotamer), 4.06 (s, 1H, minor rotamer), 3.97 (s, 1H, minor rotamer), 2.66 (m, 1H, minor rotamer), 2.51 (s, 1H, major rotamer), 2.27 (s, 1H, major rotamer), 2.15 (s, 1H, minor rotamer)

$^{13}$C NMR (carbonyl and/or amidine protons; 100 MHz): δ 173.6, 173.1, 172.6, 170.5, 164.9

EXAMPLE 6

Ph(3-Cl)(5-OCF$_3$)—(R)CH(OH)C(O)-Aze-Pab×TFA

(i) 2-Nitro-5-trifluoromethoxybenzoic acid

To a solution of 3-trifluoromethoxybenzoic acid (49.0 g, 0.24 mol) in sulfuric acid (500 mL) at less than 0° C. (ice-MeOH bath) was added a solution of potassium nitrate (31.3 g, 0.31 mol) in sulfuric acid (200 mL) over 20 minutes. The resulting solution was stirred at 0° C. for 2 hours, then warmed to room temperature and stirred for 18 hours. The reaction was poured into ice and the resulting acidic solution was extracted with EtOAc (5×). The combined organics were washed with H$_2$O (1×), brine (2×), H$_2$O (1×) and brine (1×), dried (Na$_2$SO$_4$), filtered and concentrated in vacuo to give the crude sub-title compound (65.7 g) as a solid contaminated with HOAc. The crude sub-title compound was dissolved in EtOAc and toluene and concentrated in vacuo to give a HOAc free solid (58.4 g, 97%) that was used in the next step without further purification.

$^1$H NMR (300 MHz, CDCl$_3$): δ 10.10 (br s, 1H), 8.02 (d, 1H, J=8 Hz), 7.69 (d, 1H, J=2 Hz), 7.54 (dd, 1H, J=2 Hz, J=8 Hz)

(ii) 2-Amino-5-trifluoromethoxybenzoic acid

To a solution of 2-nitro-5-trifluoromethoxybenzoic acid (56.8 g, 0.23 mol; see step (i) above) in EtOH (1000 mL) was added 10% Pd/C (5.7 g). The resulting solution was flushed with H$_2$ for 5 h, filtered through Celite® and concentrated in vacuo to give the crude sub-title compound (49.7 g, 98%) as a solid that was used in the next step without further purification.

$^1$H NMR (300 MHz, CD$_3$OD): δ 7.66 (m, 1H), 7.17 (d, 1H, J=8 Hz), 6.77 (d, 1H, J=8 Hz)

(iii) 2-Amino-3-chloro-5-trifluoromethoxybenzoic acid

To a solution of 2-amino-5-trifluoromethoxybenzoic acid (49.0 g, 0.22 mol; see step (ii) above) in HOAc (1200 mL) was slowly added sulfuryl chloride (41.8 g, 0.31 mol). Gas evolution was observed. The resulting heterogeneous mixture was stirred at room temperature for 1 h. Additional HOAc (300 mL) was added to aid stirring, followed by sulfuryl chloride in 5 mL portions until the starting material was consumed based on TLC analysis. The reaction was concentrated in vacuo to give solids that were flushed on a rotary evaporator with EtOAc (2×) followed by Et$_2$O (1×) to remove the HOAc. The resulting solids were further dried to give the HCl salt of the crude sub-title compound (60.5 g, 94%), which was used in the next step without further purification.

$^1$H NMR (300 MHz, CD$_3$OD): δ 7.72 (s, 1H), 7.44 (s, 1H), 7.22 (s, exchangeables)

(iv) 3-Chloro-5-trifluoromethoxybenzoic acid

To a solution of 2-amino-3-chloro-5-trifluoromethoxybenzoic acid (60.5 g, assume 0.22 mol; see step (iii) above) in 1,4-dioxane (1000 mL) was added 6N HCl (750 mL). Some organics oiled out of solution. The dioxane solution was cooled to less than 0° C. (ice-MeOH bath). A solution of sodium nitrite (18.2 g, 0.26 mol) in H$_2$O (250 mL) was added over 15 minutes via an addition funnel. The resulting solution was stirred for 45 min. Hypophosphorous acid (221.5 mL of 50 wt % in H$_2$O, 291.2 g, 2.20 mol) was added slowly via an addition funnel. The solution was stirred at 0° C. for 1.5 hours, then warmed to room temperature (gas evolution observed) and stirred for 18 hours. The crude solution was transferred to a separating funnel and extracted with Et$_2$O (4×). The combined organics were extracted with aqueous NaHCO$_3$ (3×). The basic aqueous layer was cautiously acidified with 6N HCl and extracted with CH$_2$Cl$_2$ (3×). The CH$_2$Cl$_2$ extracts were dried (Na$_2$SO$_4$), filtered and concentrated in vacuo to give the crude sub-title compound (26.5 g, 46% from 3-trifluoromethoxybenzoic acid) as a solid that was used in the next step without further purification.

$^1$H NMR (300 MHz, CD$_3$OD): δ 7.98 (s, 1H), 7.83 (s, 1H), 7.58 (s, 1H)

(v) 3-Chloro-5-trifluoromethoxybenzyl alcohol

To a solution of 3-chloro-5-trifluoromethoxybenzoic acid (22.5 g, 93.5 mmol; see step (iv) above) in anhydrous THF (1200 mL) under a N$_2$ atmosphere at room temperature was added a solution of BH$_3$.THF complex (140 mL of 1M in THF; 140.3 mmol). The solution was refluxed for 2 h, cooled to room temperature and stirred for 18 hours, quenched cautiously with H$_2$O and concentrated in vacuo to remove most of the THF. The residue was diluted with EtOAc and the organics were washed with brine (3×), dried (Na$_2$SO$_4$), filtered and concentrated in vacuo to give the crude sub-title compound (21.2 g, 100%) as an oil that was used without further purification.

$^1$H NMR (300 MHz, CDCl$_3$): δ 7.33 (s, 1H), 7.17 (s, 1H), 7.14 (s, 1H), 4.72 (s, 2H), 2.05 (br s, 1H)

(vi) 3-Chloro-5-trifluoromethoxybenzaldehyde

A solution of DMSO (16.1 g, 205.9 mmol) in anhydrous CH$_2$Cl$_2$ (300 mL) was cooled to −78° C. Oxalyl chloride (13.1 g, 103.0 mmol) was added slowly via a syringe (gas evolution was observed). The resulting solution was stirred at −78° C. for 15 minutes. A solution of 3-chloro-5-trifluoromethoxybenzyl alcohol (21.2 g, 93.6 mmol; see step (v) above) in CH$_2$Cl$_2$ (200 mL) was added via an addition funnel over a period of 15 minutes. The cloudy solution was stirred at −78° C. for 40 minutes and DIPEA (60.5 g, 468.0 mmol) was added via an addition funnel over 10 minutes. The resulting homogeneous solution was stirred at −78° C. for 1.5 hours, then warmed to room temperature and stirred 18 hours. The crude solution was concentrated in vacuo, the residue diluted with EtOAc and washed with H$_2$O (1×), 2N HCl (1×), brine (1×), aqueous NaHCO$_3$ (1×) and brine (1×). The organics were dried (Na$_2$SO$_4$), filtered and concentrated in vacuo to give the crude sub-title compound (19.9 g, 95%) which was used in the next step without further purification.

$^1$H NMR (300 MHz, CDCl$_3$): δ 10.00 (s, 1H), 7.83 (s, 1H), 7.66 (s, 1H), 7.51 (s, 1H)

(vii) Ph(3-Cl)(5-OCF$_3$)—(R,S)CH(OTMS)CN

To a solution of 3-chloro-5-trifluoromethoxybenzaldehyde (19.9 g, 88.6 mmol; see step (vi) above) in CH$_2$Cl$_2$ (600 mL) at 0° C. was added ZnI$_2$ (1.4 g, 4.4 mmol) and trimethylsilyl cyanide (9.7 g, 97.5 mmol). After stirring at 0° C. for 1.5 hours, and at room temperature for 2 hours, TLC analysis showed only the starting material. ZnI$_2$ was added portionwise until the reaction proceeded (over 30.0 g of ZnI$_2$ was added in total). After stirring at room temperature for 18 h, the reaction was quenched with water and the organics were separated. The organics were dried (Na$_2$SO$_4$), filtered and concentrated in vacuo to give the crude sub-title compound (27.7 g, 96%) as a liquid that was used without further purification.

$^1$H NMR (300 MHz, CDCl$_3$): δ 7.43 (s, 1H), 7.28 (s, 1H), 7.25 (s, 1H), 5.49 (s, 1H), 0.38 (s, 9H)

(viii) Ph(3-Cl)(5-OCF$_3$)—(R,S)CH(OH)C(O)OH

A suspension of Ph(3-Cl)(5-OCF$_3$)—(R,S)CH(OTMS)CN (27.7 g, 85.6 mmol; see step (vii) above) in concentrated HCl (300 mL) was refluxed for 3 hours. The resulting brown heterogeneous mixture was cooled to room temperature and extracted with Et$_2$O (2×). The initial organics were extracted with 2N NaOH (2×), then the basic layer was acidified with 2N HCl and extracted with Et$_2$O. The Et$_2$O was dried (Na$_2$SO$_4$), filtered and concentrated in vacuo to give the crude sub-title compound (4.9 g, 21%). TLC analysis of the initial organics showed the sub-title compound was still present so the basic extraction/acidification was repeated using 6N NaOH to afford additional crude sub-title compound (2.8 g, 12%). TLC analysis of the initial organics showed the sub-title compound was still present so the organics were dried (Na$_2$SO$_4$) and concentrated in vacuo to give the sodium salt of the sub-title compound (18.3 g) as an oil. The salt was then re-dissolved in Et$_2$O and the organics acidified with 2N HCl and washed with brine. The resulting organics were dried (Na$_2$SO$_4$), treated with activated charcoal, filtered through Celite® and concentrated in vacuo to give the crude sub-title compound (14.3 g, 62%) as a solid that was used in the next step without further purification.

$^1$H NMR (300 MHz, CD$_3$OD): δ 7.53 (s, 1H), 7.38 (s, 1H), 7.29 (s, 1H), 5.23 (s, 1H)

(ix) Ph(3-Cl)(5-OCF$_3$)—(R)CH(OH)C(O)OH (a)
and Ph(3-Cl)(5-OCF$_3$)—(S)CH(OAc)C(O)OH (b)

A mixture of Ph(3-Cl)(5-OCF$_3$)—(R,S)CH(OH)C(O)OH (7.7 g, 28.5 mmol; see step (viii) above) and Lipase PS "Amano" (3.8 g) in MTBE (100 mL) and vinyl acetate (50 mL) was stirred at 60° C. for 26 hours. The reaction was cooled and filtered through Celite® and the filter cake washed with EtOAc. The combined organics were concentrated in vacuo. Flash chromatography on silica gel eluting with CHCl$_3$:MeOH:concentrated NH$_4$OH (6:3:1) afforded a mixture of the ammonium salts of sub-title compound (a) and sub-title compound (b) (6.7 g) and a pure sample of the ammonium salt of sub-title compound (a) (1.2 g) with less than 95% e.e. The respective fractions were dissolved in Et$_2$O and washed with 2N HCl (1×) and brine (1×), dried (Na$_2$SO$_4$), filtered and concentrated to give the corresponding carboxylic acids (6.7 g and 1.1 g respectively). These fractions were then separately re-submitted to the resolution conditions and re-purified as necessary via chromatography on silica gel eluting with CHCl$_3$:MeOH:concentrated NH$_4$OH (6:3:1 or 75:20:5 or 145:45:10) as needed. The purified sub-title compound (a) was acidified with aqueous HCl or aqueous citric acid prior to further use. The ammonium salt of sub-title compound (b) was used without characterization.

For sub-title compound (a)

$^1$H NMR (300 MHz, CD$_3$OD): δ 7.53 (s, 1H), 7.38 (s, 1H), 7.29 (s, 1H), 5.23 (s, 1H)

$^{13}$C NMR (75 MHz, CD$_3$OD): δ 174.9, 150.9, 145.4, 136.3, 126.8, 122.0, 120.6, 118.9, 72.9

MS (m/z) 269 (M−1)$^-$ (x) Ph(3-Cl)(5-OCF$_3$)—(R)CH(OH)C(O)-Aze-Pab (Teoc)

A solution of Ph(3-Cl)(5-OCF$_3$)—(R)CH(OH)C(O)OH (0.73 g, 2.70 mmol; see step (ix) above) in DMF (40 mL) under a nitrogen atmosphere was cooled to 0° C. To the solution was added H-Aze-Pab(Teoc) (1.46 g, 3.24 mmol), collidine (0.82 g, 6.75 mmol) and PyBOP (1.83 g, 3.51 mmol). The solution was stirred at 0° C. for 2 h, warmed to room temperature and stirred 18 hours, quenched with water and concentrated in vacuo. The residue was diluted with EtOAc and washed with H$_2$O (1×), aqueous NaHCO$_3$ (1×), aqueous citric acid (1×) and brine (1×), dried (Na$_2$SO$_4$), filtered and concentrated in vacuo to give the crude sub-title compound. Flash chromatography on silica gel (2×) eluting with EtOAc:MeOH (30:1) then CH$_2$Cl$_2$:MeOH (93:7) afforded the sub-title compound (0.73 g, 43%) as a crushable foam.

$^1$H NMR (300 MHz, CD$_3$OD, complex mixture of rotamers): δ 7.78-7.82 (d, 2H, J=8 Hz), 7.25-7.54 (m, 5H), 5.25 and 5.16 (s, 1H), 5.22 and 4.79 (m, 1H), 3.92-4.58 (m, 6H), 2.20-2.76 (m, 2H), 1.04-1.13 (m, 2H), 0.08 (s, 9H)

MS (m/z) 629 (M+1)$^+$ (xi) Ph(3-Cl)(5-OCF$_3$)—(R)CH(OH)C(O)-Aze-Pab

Trifluoroacetic acid (1.0 mL) was added to a stirred ice/water-cooled solution of Ph(3-Cl)(5-OCF$_3$)—(R)CH(OH)C (O)-Aze-Pab(Teoc) (101 mg; 160 μmol; see step (x) above), in methylene chloride (10 mL). The cooling bath was removed after 1 hour. After 1.5 hours at room temperature, acetonitrile (30 mL) was added and the solvents were carefully removed under reduced pressure. The residue was dissolved in water and freeze dried to afford 90 mg (92%) of the title compound as its TFA salt.

MS (m/z) 483 (M−1)$^-$; 485 (M+1)$^+$ $^1$H NMR (300 MHz; CD$_3$OD): (complex due to diastereomers/rotamers): δ 7.70-7.80 (m, 2H), 7.45-7.58 (m, 3H), 7.24-7.38 (m, 2H), 5.26 (s, 1H), 5.17 (m, 1H, minor rotamer), 4.82 (m, 1H, major rotamer), 4.35-4.6 (m, 3H), 4.22 (m, 1H, major rotamer), 3.92-4.12 (m, 2H, minor rotamer), 2.70 (m, 1H, minor rotamer), 2.55 (m, 1H, major rotamer), 2.30 (m, 1H, major rotamer), 2.16 (m, 1H, minor rotamer)

$^{13}$C NMR (100 MHz; CD$_3$OD): (carbonyl and/or amidine carbons, rotamers): δ 173.7, 173.4, 173.0, 172.8, 168.1

EXAMPLE 7

Ph(3-Cl)(5-OCF$_3$)—(R)CH(OH)C(O)-Aze-Pab (OMe)

HATU (71 mg; 0.19 mmol) was added to a stirred ice/water-cooled solution of Ph(3-Cl)(5-OCF$_3$)—(R)CH(OH)C(O)OH (39 mg; 0.14 mmol; see Example 6 (ix) above) in DMF (3 mL). After 30 minutes, a solution of H-Aze-Pab(OMe)×2HCl (69 mg; 0.21 mmol; see international patent application WO 00/42059) and 2,4,6-collidine (0.080 mL; 0.58 mmol) in DMF (1.5 mL) was added. The reaction mixture was left overnight and the temperature was allowed to rise slowly to ambient. The solvents were removed in vacuo and the crude product was purified using reverse-phase HPLC (acetonitrile: 0.1M aq. ammonium acetate) to afford, after freeze drying the appropriate fractions, the title compound (61 mg, 97%) as a colourless solid.

MS (m/z) 513 (M−1)$^-$, 515 (M+1)$^+$ $^1$H NMR (500 MHz; CD$_3$OD): δ 7.97 (bt, 1H), 7.53 (d, 2H), 7.27 (t, 1H), 7.22 (d, 2H), 7.19 (t, 1H), 7.11 (t, 2H), 6.77 (s, 1H), 4.92 (s, 1H), 4.9 (bs, 3H), 4.81 (m, 2H), 4.40 (m, 2H), 4.09 (m, 1H) 3.87 (s, 3H), 2.58 (m, 1H), 2.37 (m, 1H)

$^{13}$C NMR (125 MHz; CD$_3$OD): (carbonyl and/or amidine carbons): δ 171.8, 169.9, 156.8

EXAMPLE 8

Parallel Synthesis of Alkoxyamidines

This synthesis was performed in a 96-well Robbins block. To wells containing an appropriate amount of O-substituted hydroxylamine (specified below; all of which are commercially available or were prepared using well known literature procedures) was added a solution of Ph(3-Cl)(5-OCF$_3$)—(R)CH(OH)C(O)-Aze-Pab(Teoc) (10 mg; 17 μmol; see Example 6(x) above) in acetonitrile (1.0 mL). The block was sealed and the reaction mixture was rotated overnight in an oven at 60° C. After cooling and filtration, the solids were washed with acetonitrile (3× 0.3 mL). The combined liquid fractions were concentrated in a vacuum centrifuge. The residue was partitioned between water (0.4 mL) and ethyl acetate (0.4 mL). After liquid-liquid extraction was finished, everything was filtered through a column of Hydromatrix™. After washing three times with ethyl acetate, the combined filtrates were concentrated in a vacuum centrifuge. Deprotection was performed by addition of methylene chloride (0.1 mL) and trifluoroacetic acid (0.3 mL). After stirring at room temperature for 3 hours, the solvents were removed in vacuo. The residue was partitioned between aqueous saturated sodium hydrogen carbonate (0.5 mL) and ethyl acetate (0.5 mL). After extraction, filtration through Hydromatrix™ and concentration (vide infra) the residue was dissolved in isopropanol/water (7/3) (1 mL). About 2% of this solution was removed and diluted with isopropanol/water (7/3) (1 mL) for LC-MS analysis. After removal of the solvents in vacuo the solid residue was transferred to a 96-well plate using acetonitrile and ethyl acetate to dissolve the compound. The solvents were evaporated in a vacuum centrifuge to afford the following title compounds:

Ph(3-Cl)(5-OCF$_3$)—(R)CH(OH)C(O)-Aze-Pab(OCH$_2$-3-(5-Me-isoxazole)) (from 3-[(aminooxy)methyl]-5-methylisoxazole×HCl (18 mg; 0.11 mmol)). Yield: 3.64 mg (35%) (MS (m/z) 596 (M+1)$^+$);

Ph(3-Cl)(5-OCF$_3$)—(R)CH(OH)C(O)-Aze-Pab(OCH$_2$-3-pyridine) (from 3-[(aminooxy)methyl]pyridine×2HCl (19 mg; 96 μmol). Yield: 5.14 mg (50%) (MS (m/z) 592 (M+1)$^+$);

Ph(3-Cl)(5-OCF$_3$)—(R)CH(OH)C(O)-Aze-Pab(OiBu) (from O-isobutyl hydroxylamine×HCl (17 mg; 140 μmol). Yield: 4.4 mg (45%). MS (m/z) 557 (M+1)$^+$);

Ph(3-Cl)(5-OCF$_3$)—(R)CH(OH)C(O)-Aze-Pab(OEt) (from O-ethyl hydroxylamine×HCl (14 mg; 140 μmol). Yield: 4.04 mg (42%). MS (m/z) 529 (M+1)$^+$);

Ph(3-Cl)(5-OCF$_3$)—(R)CH(OH)C(O)-Aze-Pab(OBn) (from O-benzylhydroxylamine×HCl (17 mg; 110 μmol). Yield: 3.22 mg (29%). MS (m/z) 591 (M+1)$^+$);

Ph(3-Cl)(5-OCF$_3$)—(R)CH(OH)C(O)-Aze-Pab(OcHexyl) (from O-cyclohexyl hydroxylamine×HCl (15 mg; 99 μmol). Yield: 2.9 mg (26%). MS (m/z) 583 (M+1)$^+$);

Ph(3-Cl)(5-OCF$_3$)—(R)CH(OH)C(O)-Aze-Pab(OcBu); (from O-cyclobutyl hydroxylamine×HCl (17 mg; 140 μmol). Yield: 3.3 mg (30%). MS (m/z) 555 (M+1)$^+$);

Ph(3-Cl)(5-OCF$_3$)—(R)CH(OH)C(O)-Aze-Pab(OCH$_2$CH$_2$OPh(3-CF$_3$)) (from O-[2-[3-(trifluoromethyl)phenoxy]ethyl]hydroxylamine×HCl (24 mg; 93 μmol). Yield: 6.52 mg (46%). MS (m/z) 689 (M+1)$^+$);

Ph(3-Cl)(5-OCF$_3$)—(R)CH(OH)C(O)-Aze-Pab(OBn(4-Cl)) (from O-(4-chlorobenzyl)hydroxylamine×HCl (16 mg; 82 μmol). Yield: 3.47 mg (29%). MS (m/z) 625 (M+1)$^+$);

Ph(3-Cl)(5-OCF$_3$)—(R)CH(OH)C(O)-Aze-Pab(OBn(3-MeO)) (from O-(3-methoxybenzyl)hydroxylamine×HCl (18 mg; 94 μmol). Yield: 4.33 mg (36%). MS (m/z) 621 (M+1)$^+$);

Ph(3-Cl)(5-OCF$_3$)—(R)CH(OH)C(O)-Aze-Pab(OBn(2-Br)) (from O-(2-bromobenzyl)hydroxylamine×HCl (23 mg; 96 μmol). Yield: 3.87 mg (30%). MS (m/z) 671 (M+1)$^+$);

Ph(3-Cl)(5-OCF$_3$)—(R)CH(OH)C(O)-Aze-Pab(OBn(4-Me)) (from O-(4-methylbenzyl)hydroxylamine×HCl (14 mg; 81 μmol). Yield: 2.91 mg (25%). MS (m/z) 605 (M+1)$^+$); and Ph(3-Cl)(5-OCF$_3$)—(R)CH(OH)C(O)-Aze-Pab(O-4-heptyl) (from O-(4-heptyl)hydroxylamine×HCl (15 mg; 89 μmol). Yield: 17 mg (100%). MS (m/z) 599 (M+1)$^+$).

EXAMPLE 9

Ph(3-Cl)(5-OCHF$_2$)—(S)CH(CH$_2$OH)C(O)-Aze-Pab×HOAc (i) 3-Chloro-5-methoxybenzoic acid Magnesium turnings (Fluka purum for Grignard reactions) were pre-treated in the following way: The turnings were placed in a glass sintered funnel and 0.1 M of hydrochloric acid was poured onto them. The turnings were stirred with a glass rod for a few seconds and then the acid was washed away with 3 portions of water. Finally, the turnings were washed with 2 portions of acetone and bottled. Tetrahydrofuran (100 mL, 99.95%) was dried by adding RedAl (1 g, 70% wt. in toluene). Pre-treated magnesium turnings (5 g, 200 mmol) were placed in a round bottomed flask, and were flushed with nitrogen 3 times. Dichloroanisole (26 g, 146 mmol) was dissolved in THF (100 mL, RedAl-dried) and dibromoethane (1.8 g, 10 mmol) was added. The reaction mixture was flushed with nitrogen and then refluxed for 2 hours. Heating was interrupted and dry ice (10 g) was added portionwise over 2 minutes. When all of the dry ice was dissolved, the reaction mixture was poured into ice containing hydrochloric acid (400 mL, 2 M). Extractive work up (ether, 300 mL) gave 11.2 g, 60.2 mmol (yield: 41%) of the sub-title compound.

$^1$H-NMR (500 MHz; acetone-$d_6$): δ 7.57 (m, 1H), 7.49 (m, 1H), 7.23 (m, 1H), 3.91 (s, 3H)

(ii) 3-Chloro-5-hydroxybenzoic acid

Alumina (1.65 g, 60 mmol) and iodine (21 g, 82 mmol) were refluxed in toluene (200 mL) for 2 hours. Then, 3-chloro-5-methoxybenzoic acid (11.2 g, 60.2 mmol; see step (i) above) dissolved in toluene (50 mL) was added, together with tetrabutylammonium iodide (1.5 g, 4 mmol), and the mixture was refluxed for another 2 hours. After cooling to ambient temperature, extractive work up gave 8.7 g, 50 mmol (yield: 83%) of the sub-title compound.

$^1$H-NMR (300 MHz; acetone-$d_6$): δ 9.27 (s, 1H), 7.48 (m, 1H), 7.44 (m, 1H), 7.11 (m, 1H)

(iii) 3-Chloro-5-difluoromethoxybenzoic acid

3-Chloro-5-hydroxybenzoic acid (6.4 g, 37.2 mmol; see step (ii) above) dissolved in chloroform (200 mL) was transferred to a 500 mL three-necked round-bottomed flask fitted with a dry ice condenser and a gas inlet tube. Sodium hydroxide (100 mL, 5 M) was added and with vigorous stirring. Chlorodifluoromethane (Freon 22; 25 g, 290 mmol) was added portionwise through the gas inlet tube at ambient temperature. After 2 hours, the reaction was complete. Extractive work up gave 6.2 g, 28 mmol (yield: 75%) of the sub-title compound.

$^1$H-NMR (500 MHz; acetone-$d_6$): δ 7.87 (m, 1H), 7.74 (m, 1H), 7.54 (m, 1H), 7.19 (t, 1H, $J_{H-F}$ 73 Hz)

(iv) 3-Chloro-5-difluoromethoxy-N-methoxy-N-methylbenzamide

3-Chloro-5-difluoromethoxybenzoic acid (1.8 g, 8 mmol; see step (iii) above) and oxalyl chloride (1.5 g, 11.8 mmol) were dissolved in methylene chloride (50 mL). DMF (2 drops) was added and the reaction mixture was stirred at ambient temperature for 30 minutes. Then, N,O-dimethylhydroxylamine (1 g, 10.2 mmol) and triethylamine (3 g, 30 mmol) were added and after another 10 minutes stirring at ambient temperature, the reaction mixture was concentrated at reduced pressure. The residue was taken up in ether (100 mL) and water (50 mL). After separation, the organic phase was washed with brine, dried over sodium sulphate, filtered and concentrated. This residue was chromatographed on silica (hexane/ethyl acetate 2:1) which gave 2 g, 7.5 mmol (93%) of the sub-title compound.

$^1$H-NMR (400 MHz; CDCl$_3$): δ 7.54 (m, 1H), 7.37 (m, 1H), 7.27 (m, 1H), 6.53 (t, 1H, $J_{H-F}$ 73 Hz)

(v) 3-Chloro-5-difluoromethoxyacetophenone

3-Chloro-5-difluoromethoxy-N-methoxy-N-methylbenzamide (2 g, 7.5 mmol; see step (iv) above) was dissolved in ether (100 mL) and cooled under nitrogen to −70° C. Methyllithium (7 mL, 11 mmol, 1.6 M in ether) was added dropwise with a syringe to the stirred reaction mixture over 1 minute. The dry ice bath was removed and the mixture was allowed to reach ambient temperature before the reaction was quenched with ammonium chloride solution (50 mL, 5% NH$_4$Cl in water). The organic phase was washed with brine, dried over sodium sulphate, filtered and concentrated at reduced pressure. The residue was chromatographed on silica (hexane:ethyl acetate 2:1) which gave 1.5 g, 6.8 mmol (yield: 90%) of the sub-title compound.

$^1$H-NMR (600 MHz; CDCl$_3$): δ 7.77 (m, 1H), 7.59 (m, 1H), 7.35 (m, 1H), 6.56 (t, 1H, $J_{H-F}$ 73 Hz), 2.60 (s, 3H)

(vi) 3-Chloro-5-difluoromethoxyphenylacetic acid methyl ester

3-Chloro-5-difluoromethoxyacetophenone (1.5 g, 6.8 mmol; see step (v) above) was dissolved in methylene chloride (200 mL). Thallium(III)nitrate×3MeOH on K-10 montmorillonite (6 g, 10 mmol (ca 0.6 mmol/g); see *J. Am. Chem. Soc.*, 98, 6750 (1976)) was added and the mixture was stirred at ambient temperature for 20 hours. The mixture was filtered and the filtrate was washed with sodium bicarbonate (100 mL, 0.5 M), dried over sodium sulphate, filtered and concentrated at reduced pressure. The residue was chromatographed on silica (hexane/ethyl acetate 2:1) which gave 1 g, 4 mmol (yield: 56%) of the sub-title compound.

$^1$H-NMR (500 MHz; CDCl$_3$): δ 7.14 (m, 1H), 7.06 (m, 1H), 6.96 (m, 1H), 6.50 (t, 1H, $J_{H-F}$ 73 Hz), 3.72 (s, 3H), 3.60 (s, 1H)

(vii) α-Formyl(3-chloro-5-difluoromethoxyphenyl) acetic acid methyl ester

3-Chloro-5-difluoromethoxyphenylacetic acid methyl ester (1 g, 4 mmol; see step (vi) above) and methyl formate (1 g, 16 mmol) were dissolved in ether (100 mL) and cooled in an ice-bath (ca. 2° C.). Then, finely cut sodium (180 mg, 7.8 mmol) and methanol (1 mL) were added and the mixture was left in the ice-bath with stirring overnight. Water (100 mL) was added carefully and the phases were separated. The water containing phase was acidified with hydrochloric acid (2 M) to pH 1 and extracted with ether (2×100 mL). The extract was dried over sodium sulphate, filtered and concentrated at reduced pressure. The residue was chromatographed on silica (hexane:ethyl acetate (1:1)) which gave 400 mg, 1.4 mmol (yield: 36%) of the sub-title compound.

$^1$H-NMR (400 MHz): δ 12.10 (d, 1H), 7.32 (d, 1H), 7.11 (m, 1H), 7.07 (m, 1H), 6.94 (m, 1H), 6.51 (t, 1H, $J_{F-H}$ 73), 3.83 (s, 3H)

(viii) 3-Chloro-5-difluoromethoxytropic acid

α-Formyl(3-chloro-5-difluoromethoxyphenyl)acetic acid methyl ester (400 mg, 1.4 mmol; see step (vii) above) was dissolved in THF:methanol (50 mL, 9:1). Sodium borohydride was added and the mixture was stirred at ambient temperature for 30 minutes. Water was added and the mixture was concentrated to produce an aqueous suspension, which was taken up in ethyl acetate and water. The phases were separated and the organic phase was washed with sodium chloride (15% in water), dried over sodium sulphate, filtered and concentrated at reduced pressure. The residue was dissolved in methanol (30 μL) and hydrolyzed with sodium hydroxide (1 mL, 10 M) at ambient temperature for 10 minutes. Extractive work up gave 180 mg, 0.68 mmol (yield: 48%) of the sub-title compound.

$^1$H-NMR (500 MHz; CDCl$_3$): δ 7.18 (m, 1H), 7.10 (m, 1H), 7.00 (m, 1H), 6.50 (t, 1H, J$_{F-H}$ 73), 4.11 (m, 1H), 3.90 (m, 1H), 3.84 (m, 1H)

(ix) Ph(3-Cl)(5-OCHF$_2$)—(S)CH(CH$_2$OH)C(O)-Aze-Pab×HOAc

3-Chloro-5-difluoromethoxytropic acid (180 mg, 0.7 mmol; see step (viii) above), H-Aze-Pab(Teoc)×HCl (450 mg, 1 mmol) and PyBOP (530 mg, 1 mmol) were dissolved in DMF (10 mL), whereafter DIPEA (550 mg, 3.9 mmol) was added. The mixture was stirred at ambient temperature for 1 h before it was diluted with brine (20 mL, 15% NaCl) and extracted with ethyl acetate (40 mL). The extract was dried over sodium sulphate, filtered and evaporated to dryness. The residue was dissolved in methylene chloride (5 mL) and trifluoroacetic acid (5 mL) was added. After 1 h at ambient temperature, the mixture of diastereomers was evaporated to dryness and the residue was chromatographed on a reverse phase column (acetonitrile:water (30:70), buffer: ammonium acetate 0.1 M). Freeze drying gave 36 mg, 0.067 mmol (yield: 10.4%) of the title compound.

MS (ES) 481 (M+1)$^+$ $^1$H-NMR (400 MHz; CDCl$_3$): δ 7.77 (d, 2H), 7.57 (d, 2H), 7.30 (m, 1H), 7.13 (m, 2H), 6.87 (t, 1H, J$_{F-H}$ 73 Hz), 4.76 (m, 1H), 4.55 (s, 2H), 4.37 (m, 1H), 4.03 (m, 2H), 3.82 (m, 1H), 3.72 (m, 1H), 2.53 (m, 1H), 2.28 (m, 1H), 1.92 (s, 1.5H)

$^{13}$C-NMR (100 MHz; CD$_3$OD): (carbonyl and/or amidine carbons) δ 172.3, 171.9, 167.2

EXAMPLE 10

Ph(3-Cl)(5-OCF$_3$)—(S)CH(CH$_2$OH)C(O)-Aze-Pab× TFA (i) 3-Chloro-5-trifluoromethoxybenzyl mesylate To a solution of 3-chloro-5-trifluoromethoxybenzyl alcohol (6.1 g) 26.9 mmol; see Example 6(v) above) in CH$_2$Cl$_2$ (250 mL) at 0° C. under a nitrogen atmosphere was added DIPEA (4.2 g, 32.3 mmol) and methanesulfonyl chloride (3.4 g, 29.6 mmol). The solution was stirred at 0° C. for 1.5 hours and quenched with H$_2$O. The organics were separated and then washed with H$_2$O (1×), 1N HCl (1×), H$_2$O (1×) and aqueous NaHCO$_3$ (1×) and then dried (Na$_2$SO$_4$), filtered and concentrated to afford the sub-title compound (8.2 g, 99%) as an oil.

$^1$H NMR (300 MHz, CDCl$_3$): δ 7.37 (s, 1H), 7.28 (s, 1H), 7.18 (s, 1H) 5.23 (s, 2H), 3.07 (s, 3H)

(ii) 3-Chloro-5-trifluoromethoxybenzyl cyanide

To a solution of 3-chloro-5-trifluoromethoxybenzyl mesylate (8.2 g, 26.8 mmol; see step (i) above) in DMSO (50 mL) was added sodium cyanide (2.6 g, 53.6 mmol). The resulting heterogeneous solution was warmed to 50° C. and sonicated for 1 hour. The reaction was cooled and partitioned between Et$_2$O and H$_2$O. The organics were washed with H$_2$O (2×) and brine (2×). The combined aqueous phases were extracted with Et$_2$O (1×). The combined organics were dried (Na$_2$SO$_4$), filtered and concentrated under a low heat and partial vacuum to afford the sub-title compound (6.3 g, 100%) as a reddish volatile oil which was used in the next step without further purification.

$^1$H NMR (300 MHz, CDCl$_3$) δ 7.32 (s, 1H), 7.24 (s, 1H), 7.12 (s, 1H), 3.78 (s, 2H)

(iii) 3-Chloro-5-trifluoromethoxyphenylacetic acid

To a solution of 3-chloro-5-trifluoromethoxybenzyl cyanide (6.3 g, 26.7 mmol; see step (ii) above) in 2-propanol (100 mL) was added water (200 mL) and potassium hydroxide (7.5 g, 133.5 mmol). The solution was refluxed for 18 h, cooled to room temperature, and the 2-propanol was removed in vacuo. The aqueous phase was washed with CH$_2$Cl$_2$ (2×) and the washings discarded. The basic aqueous phase was acidified with 2N HCl and extracted with CH$_2$Cl$_2$ (3×). The CH$_2$Cl$_2$ extracts were dried (Na$_2$SO$_4$), filtered and concentrated in vacuo to afford the sub-title compound (5.2 g, 76%) as an oil which was used in the next step without further purification.

$^1$H NMR (300 MHz, CDCl$_3$): δ 7.25 (s, 1H), 7.19 (s, 1H), 7.08 (s, 1H), 3.68 (s, 2H)

(iv) Ethyl 3-chloro-5-trifluoromethoxyphenylacetate

To a solution of 3-chloro-5-trifluoromethoxyphenylacetic acid (5.2 g, 20.4 mmol; see step (iii) above) in EtOH (600 mL) was added sulfuric acid (several drops). The solution was refluxed for 18 h, cooled to room temperature, neutralized with solid NaHCO$_3$ and the EtOH removed in vacuo. The residue was diluted with EtOAc then washed with H$_2$O (1×), aqueous NaHCO$_3$ (1×) and brine (1×). The organics were dried (Na$_2$SO$_4$), filtered and concentrated in vacuo to afford the sub-title compound (5.5 g, 96%) as an oil which was used in the next step without further purification.

$^1$H NMR (300 MHz, CDCl$_3$) δ 7.24 (s, 1H), 7.16 (s, 1H), 7.07 (s, 1H), 4.13-4.22 (q, J=8 Hz, 2H), 3.63 (s, 2H), 1.24-1.32 (t, J=8 Hz, 3H)

(v) Ph(3-Cl)(5-OCF$_3$)—(R,S)CH(CHO)C(O)OEt

To a solution of ethyl 3-chloro-5-trifluoromethoxyphenylacetate (4.5 g, 15.9 mmol; see step (iv) above) in anhydrous THF (400 mL) under a nitrogen atmosphere at less than 0° C. (ice-MeOH bath) was added sodium ethoxide (4.5 g, 63.6 mmol). The cold solution was stirred for 40 minutes and ethyl formate (8.1 g, 111.3 mmol) was added. The solution was stirred at 0° C. for 30 minutes, warmed to room temperature and stirred for 2 hours. Then, the THF was removed in vacuo. The residue was diluted with Et$_2$O and extracted with H$_2$O (1×) and 0.5M NaOH (3×). The aqueous extracts were acidified with 2N HCl and extracted with CH$_2$Cl$_2$ (3×). The combined organics were dried (Na$_2$SO$_4$), filtered and concentrated in vacuo to afford the crude sub-title compound (3.9 g). Flash chromatography on silica gel eluting with Hex:EtOAc (4:1) afforded the sub-title compound (3.0 g, 61%) as an oil.

$^1$H NMR (300 MHz, CDCl$_3$, mixture of isomers): δ 12.30 and 12.25 (s, 1H), 7.39 and 7.34 (s, 1H), 7.21 (s, 1H), 7.17 (s, 1H), 7.08 (s, 1H), 4.27-4.37 (q, J=8 Hz, 2H), 1.28-1.38 (t, J=8 Hz, 3H)

(vi) Ph(3-Cl)(5-OCF$_3$)—(R,S)CH(CH$_2$OH)C(O)OEt

To a solution of Ph(3-Cl)(5-OCF$_3$)—(R,S)CH(CHO)C(O)OEt (3.0 g, 9.66 mmol; see step (v) above) in MeOH (200 mL) at −10° C. (ice-MeOH bath) was added sodium borohydride (0.7 g, 19.32 mmol) portion-wise over 5 min. The solution was stirred at −10° C. for 45 minutes and additional sodium borohydride (0.4 g) was added. After another 15 minutes, the reaction was quenched with aqueous ammonium chloride, made weakly acidic with 2N HCl and the MeOH was removed in vacuo. The residue was diluted with EtOAc and washed with $H_2O$ (1×), aqueous $NaHCO_3$ (1×) and brine (1×). The organics were dried ($Na_2SO_4$), filtered and concentrated in vacuo to afford the crude sub-title compound. Flash chromatography on silica gel eluting with Hex:EtOAc (5:1) afforded the sub-title compound (2.0 g, 66%) as an oil.

$^1$H NMR (300 MHz, $CDCl_3$): δ 7.26 (s, 1H), 7.19 (s, 1H), 7.07 (s, 1H), 4.16-4.28 (m, 2H), 4.04-4.15 (m, 1H), 3.76-3.94 (m, 2H), 2.33 (t, J=6 Hz, 1H), 1.18-1.30 (t, J=8 Hz, 3H)

(vii) Ph(3-Cl)(5-$OCF_3$)—(R,S)CH($CH_2OH$)C(O)OH

To a solution of Ph(3-Cl)(5-$OCF_3$)—(R,S)CH($CH_2OH$)C(O)OEt (2.0 g, 6.24 mmol; see step (vi) above) in THF (50 mL) and $H_2O$ (25 mL) was added lithium hydroxide monohydrate (0.5 g, 12.48 mmol). The solution was stirred at room temperature for 1 hour and the THF was removed in vacuo. The residue was diluted with $H_2O$ then washed with $CHCl_3$ (2×) and the washings discarded. The basic aqueous layer was acidified with 2N HCl and extracted with $CHCl_3$ (4×). The $CHCl_3$ extracts were dried ($Na_2SO_4$), filtered and concentrated in vacuo to afford the crude sub-title compound (1.5 g) as an oil. Flash chromatography on silica gel eluting with $CHCl_3$:MeOH:concentrated $NH_4OH$ (gradient from 7.0:2.5: 0.5 to 0.6:3:1) afforded the ammonium salt of the sub-title compound (1.1 g). The ammonium salt was partitioned between 1N HCl and $CHCl_3$. The organics were dried ($Na_2SO_4$), filtered and concentrated in vacuo to afford the sub-title compound (also known as 3-chloro-5-trifluoromethoxytropic acid) as an oil (1.1 g, 62%).

$^1$H NMR (300 MHz, $CD_3OD$): δ 7.41 (s, 1H), 7.27 (s, 1H), 7.24 (s, 1H), 4.03 (m, 1H), 3.75-3.87 (m, 2H)

(viii) Ph(3-Cl)(5-$OCF_3$)—(S)CH($CH_2OH$)C(O)-Aze-Pab(Teoc) (a) and Ph(3-Cl)(5-$OCF_3$)—(R)CH($CH_2OH$)C(O)-Aze-Pab(Teoc) (b)

To a solution of Ph(3-Cl)(5-$OCF_3$)—(R,S)CH($CH_2OH$)C(O)OH (0.65 g, 2.28 mmol; see step (vii) above) in DMF at less than 0° C. (ice-MeOH bath) was added H-Aze-Pab(Teoc) (0.90 g, 2.39 mmol), collidine (0.71 g, 5.70 mmol) and PyBOP (1.31 g, 2.51 mmol). The resulting solution was stirred at less than 0° C. for 1 h, warmed to room temperature and stirred for 1 hour. The DMF was then removed in vacuo. The residue was diluted with EtOAc and washed with dilute aqueous HCl (1×), brine (1×), aqueous $NaHCO_3$ (1×) and brine (1×). The organics were dried ($Na_2SO_4$), filtered and concentrated in vacuo to afford the crude sub-title compound (2.1 g) as a mixture of diastereomers. Flash chromatography (3×) on silica gel eluting first with EtOAc:MeOH (95:5) then with $CH_2Cl_2$:MeOH (97:3) and last with $CH_2Cl_2$:MeOH (95: 5) afforded the sub-title compounds diastereomer (a) (0.51 g, 35%) and diastereomer (b) (0.45 g, 31%) as crushable foams.

For sub-title compound diastereomer (a)
$^1$H NMR (300 MHz, $CD_3OD$, complex mixture of rotamers) δ 7.79-7.85 (d, J=8 Hz, 2H), 7.22-7.49 (m, 5H), 5.17-4.77 (m, 1H), 4.53-4.18 (m, 4H), 3.58-4.11 (m, 5H), 2.47-2.73 (m, 1H), 2.11-2.34 (m, 1H), 1.08-1.12 (m, 2H), 0.07 (s, 9H)
MS (m/z) 643 (M+1)$^+$ (ix) Ph(3-Cl)(5-$OCF_3$)—(S)CH($CH_2OH$)C(O)-Aze-Pab×TFA Ph(3-Cl)(5-$OCF_3$)—(S)CH($CH_2OH$)C(O)-Aze-Pab (Teoc), (78 mg, 0.121 mmol; see step (viii) above—diastereomer (a)), was dissolved in 5 mL of trifluoroacetic acid. After 10 minutes, the reaction was over and the solvent was evaporated. The residue was freeze dried from water and acetonitrile to give the desired product. Yield: 70 mg (94%).

MS (m/z) 483 (M−1)$^-$; 485 (M+1)$^+$ $^1$H-NMR (400 MHz; $D_2O$) rotamers 1:1: δ 8.83 (bt, 1H), 7.79 (d, 1H), 7.72 (d, 1H), 7.54 (d, 1H), 7.43 (d, 2H), 7.35 (m, 1H, rotamer), 7.28 (m, 1H, rotamer), 7.20 (m, 1H, rotamer), 7.05 (m, 1H, rotamer), 5.22 (m, 1H, rotamer), 4.83 (m, 1H, rotamer), 4.57 (m, 2H, rotamer), 4.38 (m, 2H, rotamer), 4.3-3.7 (m, 5H), 2.77 (m, 1H, rotamer), 2.55 (m, 1H, rotamer), 2.27 (m, 1H)

$^{13}$C-NMR (100 MHz; $D_2O$): (carbonyl and/or amidine carbons; rotamers) δ 172.9, 172.2, 172.0, 171.8, 166.9

EXAMPLE 11

Ph(3-Cl)(5-$OCF_3$)—(S)CH($CH_2OH$)C(O)-Aze-Pab(OMe)

(i) Ph(3-Cl)(5-$OCF_3$)—(S)CH($CH_2OH$)C(O)-Aze-Pab(OMe, Teoc)

Ph(3-Cl)(5-$OCF_3$)—(S)CH($CH_2OH$)C(O)-Aze-Pab (Teoc) (100 mg, 0.155 mmol; see Example 10(viii) above), was dissolved in 12 mL of tetrahydrofuran. O-Methylhydroxylamine hydrochloride (44 mg, 0.53 mmol), was added and the reaction was heated at 50° C. overnight. The reaction mixture was evaporated and the residue purified by preparative HPLC ($CH_3CN$/0.1 M $NH_4OAc$ (70/30)). The pertinent fractions were evaporated and the residue dissolved in a small amount of acetonitrile and water and freeze dried. The freeze drying was repeated once. Yield: 80 mg (76%) of pure material.

$^1$H-NMR (400 MHz; $CD_3OD$) rotamers: δ 7.5-7.4 (m, 3H), 7.35-7.2 (m, 4H), 5.15 (m, 1H, minor rotamer), 4.74 (m, 1H, major rotamer), 4.5-4.25 (m, 3H), 4.2-3.95 (m, 4H), 3.91 (b, 3H), 3.9-3.6 (m, 2H), 2.63 (m, 1H, minor rotamer), 2.50 (m, 1H, major rotamer), 2.3-2.1 (m, 1H), 0.95 (m, 2H), 0.02 (s, 9H, major rotamer), 0.01 (s, 9H, minor rotamer)

(ii) Ph(3-Cl)(5-$OCF_3$)—(S)CH($CH_2OH$)C(O)-Aze-Pab(OMe)

Ph(3-Cl)(5-$OCF_3$)—(S)CH($CH_2OH$)C(O)-Aze-Pab (OMe, Teoc), (80 mg, 0.12 mmol; see step (i) above), was dissolved in 1 mL of methylene chloride and cooled in an ice bath. Trifluoroacetic acid, 3 mL, was added and the reaction flask was kept in the ice bath for two hours. The mixture was evaporated and dissolved in ethyl acetate and washed three times with $NaHCO_3$ (aq) then with water and brine. The organic phase was dried ($Na_2SO_4$), filtered and evaporated. The residue was freeze dried from a small amount of acetonitrile and water. Yield: 60 mg (95%) of pure title product.

MS (m/z) 528 (M−1); 531 (M+1)$^+$ $^1$H-NMR (500 MHz; $CD_3OD$) rotamers: δ 7.65-7.55 (m, 3H, rotamers), 7.45 (m, 1H, major rotamer), 7.4-7.2 (m, 4H), 5.15 (m, 1H, minor rotamer), 4.74 (m, 1H, major rotamer), 4.5-4.3 (m, 3H), 4.05-3.95 (m, 2H), 3.85 (m, 1H, major rotamer), 3.82 (s, 3H, major rotamer), 3.81 (s, 3H, minor rotamer), 3.73 (m, 1H, major rotamer), 3.67 (m, 1H, minor rotamer), 3.62 (m, 1H, minor rotamer), 2.63 (m, 1H, minor rotamer), 2.50 (m, 1H, major rotamer), 2.24 (m, 1H, major rotamer), 2.16 (m, 1H, minor rotamer)

¹³C-NMR (125 MHz; CD₃OD): (carbonyl and/or amidine carbons, rotamers) δ 174.0, 173.2, 172.7, 172.6, 155.1

EXAMPLE 12

Ph(3-Cl)(5-OCHF₂)—(R)CH(OH)C(O)-Aze-Pab (OMe)

(i) Ph(3-Cl)(5-OCHF₂)—(R)CH(OH)C(O)-Aze-Pab (OMe, Teoc)

Ph(3-Cl)(5-OCHF₂)—(R)CH(OH)C(O)-Aze-Pab(Teoc) (0.40 g, 0.65 mmol; see Example 1(ix) above), was dissolved in 20 mL of acetonitrile and 0.50 g (6.0 mmol) of O-methyl hydroxylamine hydrochloride was added. The mixture was heated at 70° C. for 2 h. The solvent was evaporated and the residue was partitioned between water and ethyl acetate. The aqueous phase was extracted twice more with ethyl acetate and the combined organic phase was washed with water, brine, dried (Na₂SO₄), filtered and evaporated. Yield: 0.41 g (91%).

¹H-NMR (400 MHz; CDCl₃): δ 7.83 (bt, 1H), 7.57 (bs, 1H), 7.47 (d, 2H), 7.30 (d, 2H), 7.20 (m, 1H), 7.14 (m, 1H), 7.01 (m, 1H), 6.53 (t, 1H), 4.89 (s, 1H), 4.87 (m, 1H), 4.47 (m, 2H), 4.4-4.2 (b, 1H), 4.17-4.1 (m, 3H), 3.95 (s, 3H), 3.67 (m, 1H), 2.68 (m, 1H), 2.42 (m, 1H) 0.97 (m, 2H), 0.01 (s, 9H).

(ii) Ph(3-Cl)(5-OCHF₂)—(R)CH(OH)C(O)-Aze-Pab (OMe)

Ph(3-Cl)(5-OCHF₂)—(R)CH(OH)C(O)-Aze-Pab(OMe, Teoc) (0.40 g, 0.62 mmol; see step (i) above), was dissolved in 5 mL of TFA and allowed to react for 30 min. TFA was evaporated and the residue was partitioned between ethyl acetate and NaHCO₃ (aq.). The aqueous phase was extracted twice more with ethyl acetate and the combined organic phase was washed with water, brine, dried (Na₂SO₄), filtered and evaporated. The product was freeze dried from water/acetonitrile. No purification was necessary. Yield: 0.28 g (85%).

¹H-NMR (600 MHz; CDCl₃): δ 7.89 (bt, 1H), 7.57 (d, 2H), 7.28 (d, 2H), 7.18 (m, 1H), 7.13 (m, 1H), 6.99 (m, 1H), 6.51 (t, 1H), 4.88 (s, 1H), 4.87 (m, 1H), 4.80 (bs, 2H), 4.48 (dd, 1H), 4.43 (dd, 1H), 4.10 (m, 1H), 3.89 (s, 3H), 3.68 (m, 1H), 2.68 (m, 1H), 2.40 (m, 1H).

¹³C-NMR (125 MHz; CDCl₃): (carbonyl and/or amidine carbons, rotamers) 172.9, 170.8, 152.7, 152.6

MS (m/z) 495 (M−1)⁻, 497 (M+1)⁺

EXAMPLE 13

Ph(3-OCHF₂)—(R)CH(OH)C(O)-Aze-Pab×HOAc

Ph(3-Cl)(5-OCHF₂)—(R)CH(OH)C(O)-Aze-Pab(OMe) (13 mg, 0.026 mmol; see Example 12 above) was dissolved in abs. ethanol (5 mL) and 30 mg of 10% Pd/C was added. Finally acetic acid (5 µL) was added and the mixture was hydrogenated at atmospheric pressure for 20 h. The mixture was filtered through Celite®, evaporated, and purified by reversed phase HPLC (0.1 M aq. ammonium acetate/MeCN). The appropriate fractions were freeze-dried to afford the title compound as a white solid: 8.5 mg (66%).

¹H-NMR (400 MHz; CD₃OD) rotamers: δ 7.73-7.78 (m, 2H), 7.55 (d, 2H), 7.19-7.43 (m, 3H), 7.06-7.13 (m, 1H), 6.83 (t, 1H, J_HF=74 Hz, major rotamer), 6.81 (t, 1H, major rotamer), 5.20 (s, 1H, major rotamer), 5.19 (m, 1H, minor rotamer), 5.15 (s, 1H, minor rotamer), 4.78 (m, 1H, major rotamer), 4.4-4.6 (several peaks, 2H), 4.35 (m, 1H, major rotamer), 4.08 (m, 1H), 3.99 (m, 1H, minor rotamer), 2.70 (m, 1H, minor rotamer), 2.52 (m, 1H, major rotamer), 2.30 (m, 1H, major rotamer), 2.15 (m, 1H, minor rotamer), 1.89 (s, 3H).

¹³C-NMR (100 MHz; CD₃OD): (carbonyl and/or amidine carbons, rotamers) δ 173.7, 172.9, 168.3.

MS (m/z) 433 (M+1)⁺; 431 (M−1)⁻

EXAMPLE 14

Ph(3-OCF₃)—(R)CH(OH)C(O)-Aze-Pab×TFA

Ph(3-Cl)(5-OCF₃)—(R)CH(OH)C(O)-Aze-Pab×TFA (34 mg, 0.057 mmol, from Example 6) was dissolved in 5 mL of ethanol and 20 mg of 10% Pd/C was added. The mixture was hydrogenated at atmospheric pressure overnight. The mixture was filtered through Celite®, evaporated, and freeze dried from water/acetonitrile.

¹H-NMR (400 MHz; CD₃OD) rotamers: δ 7.8-7.7 (m, 2H), 7.55 (m, 2H), 7.5-7.2 (m, 4H), 5.24 (s, 1H, major rotamer), 5.23 (m, 1H, minor rotamer), 5.18 (s, 1H, minor rotamer), 4.77 (m, 1H, major rotamer), 4.6-4.45 (m, 2H), 4.36 (m, 1H, major rotamer), 4.08 (m, 1H), 3.99 (m, 1H, minor rotamer), 2.70 (m, 1H, minor rotamer), 2.52 (m, 1H, major rotamer), 2.30 (m, 1H, major rotamer), 2.15 (m, 1H, minor rotamer).

¹³C-NMR (100 MHz; CD₃OD): (carbonyl and/or amidine carbons, rotamers) δ 174.1, 173.9, 173.5, 172.9, 168.2.

¹⁹-F NMR (282 MHz; CD₃OD): −59.8 and −59.9 (3F, minor and major rotamer respectively), −77.4 (3F) indicates that the salt is TFA.

MS (m/z) 451.3 (M+1)⁺

EXAMPLE 15

Ph(3-Cl)(5-OCH₂CF₃)—(R)CH(OH)C(O)-Aze-Pab× TFA (i) 3-Chloro-5-trifluoroethoxybenzaldehyde To a magnetically stirred solution of 3-chloro-5-hydroxybenzaldehyde (2.0 g, 12.8 mmol; see Example 1(ii) above) and potassium carbonate (2.3 g, 16.6 mmol) in DMF (35 mL) under nitrogen was added 2,2,2-trifluoroethyl p-toluenesulfonate (4.2 g, 16.6 mmol) at room temperature. The mixture was heated to 110° C. for 7 h and then stirred overnight at room temperature. The reaction was cooled to 0° C., poured into ice-cold 2 N HCl (100 mL) and extracted with EtOAc (2× 75 mL). The combined organic extracts were washed with 0.5 N HCl (2× 50 mL), dried (Na₂SO₄), filtered, and concentrated in vacuo. The brown oil was chromatographed on silica gel eluting with Hex:EtOAc (6:1) to afford the sub-title compound (1.9 g, 61%) as a yellow oil.

¹H NMR (300 MHz, CDCl₃) δ 9.44 (s, 1H), 7.56 (s, 1H), 7.33 (s, 1H), 7.28 (s, 1H), 4.42 (q, J=8 Hz, 2H)

(ii) Ph(3-Cl)(5-OCH₂CF₃)—(R,S)CH(OTMS)CN

To a solution of 3-chloro-5-trifluoroethoxybenzaldehyde (5.2 g, 21.7 mmol; see step (i) above) and zinc iodide (1.7 g, 5.4 mmol) in CH₂Cl₂ (200 mL) under nitrogen was added trimethylsilyl cyanide (4.3 g, 43.3 mmol) dropwise via syringe at 0° C. The mixture was stirred at 0° C. for 3 h then diluted with H₂O (150 mL). The organic layer was separated, dried (Na₂SO₄), filtered, and concentrated in vacuo to afford the sub-title compound (6.9 g, 95%) as a yellow oil which was used without further purification.

¹H NMR (300 MHz, CDCl₃) δ 7.27 (s, 1H), 6.98 (s, 2H), 5.44 (s, 1H), 4.38 (q, J=8 Hz, 2H), 0.30 (s, 9H)

(iii) Ph(3-Cl)(5-OCH₂CF₃)—(R,S)CH(OH)C(O)OH

Concentrated hydrochloric acid (170 mL) was added to Ph(3-Cl)(5-OCH₂CF₃)—(R,S)CH(OTMS)CN (6.9 g, 20.4 mmol; see step (ii) above) and stirred at 100° C. for 1 h. After cooling to room temperature, the reaction was further cooled to 0° C. and basified slowly with 3 N NaOH (300 mL). This mixture was washed with Et₂O (2× 100 mL) and the aqueous layer was acidified with 2 N HCl (50 mL). The aqueous layer was then extracted with EtOAc (2× 100 mL), dried (Na₂SO₄), filtered, and concentrated in vacuo to afford the sub-title compound (5.3 g, 92%) as a pale yellow oil which was used without further purification.

¹H NMR (300 MHz, CD₃OD) δ 7.18 (s, 1H), 7.07 (s, 1H), 7.02 (s, 1H), 5.13 (s, 1H), 4.58 (q, J=8 Hz, 2H)

(iv) Ph(3-Cl)(5-OCH₂CF₃)—(R)CH(OH)C(O)OH (a) and Ph(3-Cl)(5-OCH₂CF₃)—(S)CH(OAc)C(O)OH (b)

A solution of Ph(3-Cl)(5-OCH₂CF₃)—(R,S)CH(OH)C(O)OH (7.06 g, 24.8 mmol; see step (iii) above) and Lipase PS "Amano" (4.30 g) in vinyl acetate (250 mL) and MTBE (250 mL) was heated at 70° C. under nitrogen for 40 h. The reaction was cooled to room temperature, the enzyme was removed by filtration washing with EtOAc, and the filtrate concentrated in vacuo. Chromatography on silica gel eluting with CHCl₃: MeOH:Et₃N (92:6:2) afforded the triethylamine salt of the sub-title compound (a) (3.02 g) as a yellow oil. The salt of sub-title compound (a) was dissolved in H₂O (150 mL), acidified with 2 N HCl and extracted with EtOAc (2× 75 mL). The combined organic extracts were dried (Na₂SO₄), filtered, and concentrated in vacuo to yield the sub-title compound (a) (2.18 g) as an off-white solid. In addition, the triethylamine salt of sub-title compound (b) (4.73 g) was obtained from the column chromatography mentioned above.

Data for Sub-Title Compound (a):

mp: 98-103° C.

¹H NMR (300 MHz, CD₃OD) δ 7.18 (s, 1H), 7.07 (s, 1H), 7.02 (s, 1H), 5.13 (s, 1H), 4.58 (q, J=8 Hz, 2H).

¹³C NMR (75 MHz, CD₃OD) δ 175.4, 159.6, 144.6, 136.2, 125.0 (q, J=277 Hz), 121.8, 115.9, 113.1, 73.3, 67.0 (q, J=35 Hz)

HPLC Analysis: 98.6%, >99% ee, Chiralcel OD Column (97:3:0.5 Hex:EtOH:TFA mobile phase)

$[\alpha]^{25}_D = -81.5°$ (c=1.0, MeOH)

APCI-MS: (M−1)=283 m/z (v) Ph(3-Cl)(5-OCH₂CF₃)—(R)CH(OH)C(O)-Aze-Pab(Teoc)

To a solution of Ph(3-Cl)(5-OCH₂CF₃)—(R)CH(OH)C(O)OH (0.50 g, 1.8 mmol; see step (iv) above (compound (a))) in DMF (20 mL) under nitrogen was added H-Aze-Pab(Teoc)×HCl (1.03 g, 2.3 mmol), PyBOP (1.01 g, 1.9 mmol), and DIPEA (0.57 g, 4.4 mmol) at 0° C. The reaction was stirred at 0° C. for 2 h and then at room temperature for 20 h. The mixture was concentrated in vacuo and the residue chromatographed twice on silica gel, eluting first with CHCl₃:EtOH (10:1) and then with EtOAc:EtOH (10:1) to afford the sub-title compound (0.55 g, 48%) as a crushable white foam.

mp: 90-95° C.

$R_f$=0.42 (10:1 CHCl₃:EtOH)

¹H NMR (300 MHz, CD₃OD, complex mixture of rotamers) δ 7.78-7.81 (m, 2H), 7.38-7.41 (m, 2H), 7.12-7.16 (m, 1H), 7.00-7.06 (m, 2H), 5.09-5.22 and 4.75-4.79 (m, 2H), 3.94-4.61 (m, 8H), 2.09-2.75 (m, 2H), 1.04-1.11 (m, 2H), 0.70 (s, 9H)

APCI-MS: (M+1)=643 m/z (vi) Ph(3-Cl)(5-OCH₂CF₃)—(R)CH(OH)C(O)-Aze-Pab×TFA

Ph(3-Cl)(5-OCH₂CF₃)—(R)CH(OH)C(O)-Aze-Pab(Teoc) (0.066 g, 0.103 mmol; see step (v) above), was dissolved in 3 mL of TFA and allowed to react for 30 min. TFA was evaporated and the residue was freeze dried from water/acetonitrile to yield 0.060 g (94%) of the title compound as its TFA salt.

¹H-NMR (400 MHz; CD₃OD) rotamers: δ 7.8-7.7 (m, 2H), 7.6-7.5 (m, 2H), 7.2-7.0 (m, 3H), 5.21 (m, 1H, minor rotamer), 5.17 (s, 1H, major rotamer), 5.11 (s, 1H, minor rotamer), 4.81 (m, 1H, major rotamer), 4.6-4.4 (m, 4H), 4.37 (m, 1H, major rotamer), 4.16 (m, 1H, major rotamer), 4.06 (m, 1H, minor rotamer), 3.99 (m, 1H, minor rotamer), 2.70 (m, 1H, minor rotamer), 2.54 (m, 1H, major rotamer), 2.29 (m, 1H, major rotamer), 2.15 (m, 1H, minor rotamer)

¹³C-NMR (100 MHz; CD₃OD): (carbonyl and/or amidine carbons, rotamers) δ 172.2, 171.8, 171.7, 167.0.

MS (m/z) 499.3 (M+1)⁺

EXAMPLE 16

Ph(3-Cl)(5-OCH₂CF₃)—(R)CH(OH)C(O)-Aze-Pab(OMe)

To a solution of Ph(3-Cl)(5-OCH₂CF₃)—(R)CH(OH)C(O)OH (0.48 g, 1.7 mmol; see Example 15(iv) above (compound (a)) in DMF (20 mL) under nitrogen was added H-Aze-Pab(OMe)×2HCl (0.74 g, 2.2 mmol), PyBOP (0.97 g, 1.9 mmol), and DIPEA (0.55 g, 4.2 mmol) at 0° C. The reaction was stirred at 0° C. for 2 h and then at room temperature for 20 h. The mixture was concentrated in vacuo and the residue chromatographed twice on silica gel, eluting first with CHCl₃:EtOH (10:1) and second with EtOAc:EtOH (10:1) to afford the title compound (0.62 g, 69%) as a crushable white foam.

mp: 75-80° C.

$R_f$=0.43 (10:1 CHCl₃:EtOH)

¹H NMR (300 MHz, CD₃OD, complex mixture of rotamers) δ 7.57-7.60 (m, 2H), 7.32-7.36 (m, 2H), 7.13-7.17 (m, 1H), 7.00-7.06 (m, 2H), 5.09-5.19 and 4.74-4.80 (m, 2H), 3.93-4.62 (m, 6H), 3.81 (s, 3H), 2.10-2.73 (m, 2H)

APCI-MS: (M+1)=529 m/z

EXAMPLE 17

Ph(3-Cl)(5-OCH₂CHF₂)—(R)CH(OH)C(O)-Aze-Pab×TFA (i) 2,2-Difluoroethyl ester methanesulfonic acid To a magnetically stirred solution of 2,2-difluoroethanol (1.52 g, 18.5 mmol) in CH₂Cl₂ (20 mL) under nitrogen was added triethylamine (5.61 g, 55.5 mmol) and methanesulfonyl chloride (2.54 g, 22.2 mmol) at 0° C. The mixture was stirred at 0° C. for 1.5 h, diluted with CH₂Cl₂ (50 mL), and washed with 2 N HCl (50 mL). The aqueous layer was extracted with CH₂Cl₂ (30 mL) and the combined organic extracts washed with brine (30 mL), dried (Na₂SO₄), filtered, and concentrated in vacuo to afford the sub-title compound (2.52 g, 85%) as a yellow oil which was used without further purification.

$^1$H NMR (300 MHz, CDCl$_3$) δ 6.02 (tt, J=3 Hz, J=55 Hz, 1H), 4.39 (dt, J=3 Hz, J=13 Hz, 2H), 3.13 (s, 3H)

(ii) 3-Chloro-5-difluoroethoxybenzaldehyde

To a solution of 3-chloro-5-hydroxybenzaldehyde (1.50 g, 9.6 mmol; see Example 1(ii) above) and potassium carbonate (1.72 g, 12.5 mmol) in DMF (10 mL) under nitrogen was added a solution of 2,2-difluoroethyl ester methanesulfonic acid (2.0 g, 12.5 mmol; see step (i) above) in DMF (10 mL) dropwise at room temperature. The mixture was heated to 10° C. for 6 h and then stirred overnight at room temperature. The reaction was cooled to 0° C., poured into ice-cold 2 N HCl (100 mL), and extracted with EtOAc (2× 75 mL). The combined organic extracts were washed with 0.5 N HCl (2× 50 mL), dried (Na$_2$SO$_4$), filtered, and concentrated in vacuo. The brown oil was chromatographed on silica gel eluting with Hex:EtOAc (5:1) to afford the sub-title compound (1.35 g, 64%) as a yellow oil.

$^1$H NMR (300 MHz, CDCl$_3$) δ 9.92 (s, 1H), 7.52 (s, 1H), 7.31 (s, 1H), 7.22 (s, 1H), 6.12 (tt, J=3 Hz, J=55 Hz, 1H), 4.26 (dt, J=3 Hz, J=15 Hz, 2H)

(iii) Ph(3-Cl)(5-OCH$_2$CHF$_2$)—(R,S)CH(OTMS)CN

To a solution of 3-chloro-5-difluoroethoxybenzaldehyde (1.35 g, 6.1 mmol; see step (ii) above) and zinc iodide (0.48 g, 1.5 mmol) in CH$_2$Cl$_2$ (50 mL) was added trimethylsilyl cyanide (1.21 g, 12.2 mmol) dropwise at 0° C. under nitrogen. The mixture was stirred at 0° C. for 3 h, then diluted with H$_2$O (50 mL). The organic layer was separated, dried (Na$_2$SO$_4$), filtered, and concentrated in vacuo to afford the sub-title compound (1.85 g, 95%) as a brown oil which was used without further purification.

$^1$H NMR (300 MHz, CDCl$_3$) δ 7.13 (s, 1H), 6.94 (s, 2H), 6.10 (tt, J=3 Hz, J=55 Hz, 1H), 5.43 (s, 1H), 4.20 (dt, J=3 Hz, J=15 Hz, 2H), 0.28 (s, 9H)

(iv) Ph(3-Cl)(5-OCH$_2$CHF$_2$)—(R,S)CH(OH)C(O)OH

Concentrated hydrochloric acid (60 mL) was added to Ph(3-Cl)(5-OCH$_2$CHF$_2$)—(R,S)CH(OTMS)CN (1.85 g, 5.8 mmol; see step (iii) above) and stirred at 100° C. for 1 h. After cooling to room temperature, the reaction was further cooled to 0° C., basified slowly with 3 N NaOH (~180 mL) and washed with Et$_2$O (2× 75 mL). The aqueous layer was acidified with 2 N HCl (20 mL) and extracted with EtOAc (2× 75 mL). The combined organic extracts were dried (Na$_2$SO$_4$), filtered, and concentrated in vacuo to afford the sub-title compound (1.50 g, 97%) as a pale yellow solid which was used without further purification.

$^1$H NMR (300 MHz, CD$_3$OD) δ 7.15 (s, 1H), 7.05 (s, 1H), 6.98 (s, 1H), 6.19 (tt, J=4 Hz, J=55 Hz, 1H), 5.12 (s, 1H), 4.25 (dt, J=4 Hz, J=17 Hz, 2H)

(v) Ph(3-Cl)(5-OCH$_2$CHF$_2$)—(S)CH(OAc)C(O)OH (a) and Ph(3-Cl)(5-OCH$_2$CHF$_2$)—(R)CH(OH)C(O)OH (b)

A solution of Ph(3-Cl)(5-OCH$_2$CHF$_2$)—(R,S)CH(OH)C(O)OH (3.90 g, 14.6 mmol; see step (iv) above) and Lipase PS "Amano" (2.50 g) in vinyl acetate (140 mL) and MTBE (140 mL) was heated at 70° C. under nitrogen for 40 h. The reaction was cooled to room temperature, the enzyme removed by filtration washing with EtOAc, and the filtrate concentrated in vacuo. Chromatography on silica gel eluting with CHCl$_3$:MeOH:Et$_3$N (92:6:2) afforded the triethylamine salt of the sub-title compound (a) as a yellow oil. In addition, the triethylamine salt of the sub-title compound (b) (1.47 g) was obtained and the salt was dissolved in H$_2$O (100 mL), acidified with 2 N HCl and extracted with EtOAc (2× 75 mL). The combined organic extracts were dried (Na$_2$SO$_4$), filtered, and concentrated in vacuo to yield the sub-title compound (b) (1.00 g) as an off-white solid.

Data for Sub-Title Compound (b):

mp: 103-106° C.

R$_f$=0.39 (90:8:2 CHCl$_3$:MeOH:Et$_3$N)

$^1$H NMR (300 MHz, CD$_3$OD) δ 7.13 (s, 1H), 7.04 (s, 1H), 6.97 (s, 1H), 6.17 (tt, J=4 Hz, J=55 Hz, 1H), 5.12 (s, 1H), 4.24 (dt, J=4 Hz, J=8 Hz, 2H).

$^{13}$C NMR (75 MHz, CD$_3$OD) δ 175.5, 160.3, 144.5, 136.1, 121.3, 115.7, 115.3, (t, J=240 Hz), 112.9, 73.4, 68.6 (t, J=29 Hz)

HPLC Analysis: 96.2%, >95.0% ee, ChiralPak AD Column (95:5:0.5 Hex:EtOH:TFA mobile phase)

[α]$^{25}_D$=−84.00 (c=0.85 MeOH)

APCI-MS: (M−1)=265 m/z

(vi) Ph(3-Cl)(5-OCH$_2$CHF$_2$)—(R)CH(OH)C(O)-Aze-Pab(Teoc)

To a solution of Ph(3-Cl)(5-OCH$_2$CHF$_2$)—(R)CH(OH)C(O)OH (0.35 g, 1.3 mmol; see step (v) above (compound (b))) in DMF (18 mL) under nitrogen was added H-Aze-Pab(Teoc)×HCl (0.76 g, 1.7 mmol), PyBOP (0.75 g, 1.4 mmol), and DIPEA (0.43 g, 3.3 mmol) at 0° C. The reaction was stirred at 0° C. for 2 h and then at room temperature for 20 h. The mixture was concentrated in vacuo and the residue chromatographed twice on silica gel, is eluting first with CHCl$_3$:EtOH (10:1), and then with EtOAc:EtOH (10:1) to afford the sub-title compound (0.69 g, 84%) as a crushable white foam.

mp: 108-118° C.

R$_f$=0.48 (10:1 CHCl$_3$:EtOH)

$^1$H NMR (300 MHz, CD$_3$OD, complex mixture of rotamers) δ 7.78-7.81 (m, 2H), 7.40-7.43 (m, 2H), 7.09-7.12 (m, 1H), 6.96-7.02 (m, 2H), 6.16 (t, J=57 Hz, 1H), 5.09-5.20 and 4.75-4.80 (m, 2H), 3.95-4.55 (m, 8H), 2.10-2.75 (m, 2H), 1.04-1.11 (m, 2H), 0.07 (s, 9H)

APCI-MS: (M+1)=625 m/z

(vii) Ph(3-Cl)(5-OCH$_2$CHF$_2$)—(R)CH(OH)C(O)-Aze-Pab×TFA

Ph(3-Cl)(5-OCH$_2$CHF$_2$)—(R)CH(OH)C(O)-Aze-Pab(Teoc) (0.086 g, 0.138 mmol; see step (vi) above), was dissolved in 3 mL of TFA and allowed to react for 1 h. TFA was evaporated and the residue was freeze dried from water/acetonitrile to yield 0.080 g (98%) of the title compound as its TFA salt.

$^1$H-NMR (300 MHz; CD$_3$OD) rotamers: δ 7.8-7.7 (m, 2H), 7.6-7.5 (m, 2H), 7.15-6.95 (m, 3H), 6.35-5.95 (m, 1H), 5.20 (m, 1H, minor rotamer), 5.14 (s, 1H, major rotamer), 5.10 (s, 1H, minor rotamer), 4.80 (m, 1H, major rotamer), 4.6-4.0 (m, 6H), 2.70 (m, 1H, minor rotamer), 2.53 (m, 1H, major rotamer), 2.29 (m, 1H, major rotamer), 2.15 (m, 1H, minor rotamer).

$^{13}$C-NMR (100 MHz; CD$_3$OD): (carbonyl and/or amidine carbons, rotamers) δ 174.0, 173.8, 173.4, 172.9, 168.2

MS (m/z) 481.2 (M+1)$^+$

EXAMPLE 18

Ph(3-Cl)(5-OCH$_2$CHF$_2$)—(R)CH(OH)C(O)-Aze-Pab(OMe)

To a solution of Ph(3-Cl)(5-OCH$_2$CHF$_2$)—(R)CH(OH)C(O)OH (0.30 g, 1.7 mmol; see Example 17(v) above (compound (b))) in DMF (15 mL) under nitrogen was added H-Aze-Pab(OMe)×2HCl (0.49 g, 1.5 mmol), PyBOP (0.65 g, 1.2 mmol), and DIPEA (0.36 g, 2.8 mmol) at 0° C. The reaction was stirred at 0° C. for 2 h and then at room temperature for 20 h. The mixture was concentrated in vacuo and the residue chromatographed three times on silica gel, eluting first with CHCl$_3$:EtOH (10:1), then with EtOAc:EtOH (10:1), and finally with CHCl$_3$:MeOH (20:1) to afford the title compound (0.47 g, 81%) as a crushable white foam.

mp: 65-75° C.
R$_f$=0.37 (10:1 CHCl$_3$:EtOH)
$^1$H NMR (300 MHz, CD$_3$OD, complex mixture of rotamers) δ 7.58-7.60 (m, 2H), 7.32-7.35 (m, 2H), 7.09-7.12 (m, 1H), 6.96-7.02 (m, 2H), 6.16 (t, J=55 Hz, 1H), 5.08-5.18 and 4.74-4.80 (m, 2H), 3.96-4.50 (m, 6H), 3.80 (s, 3H), 2.10-2.75 (m, 2H)
APCI-MS: (M+1)=511 m/z.

EXAMPLE 19

Ph(3-Cl)(5-OCH$_2$F)—(R)CH(OH)C(O)-Aze-Pab×TFA (i) Ph(3-Cl)(5-TMSO)—(R,S)CH(OTMS)CN

To a solution of 3-chloro-5-hydroxybenzaldehyde (9.8 g, 62.6 mmol; see Example 1(ii) above) and ZnI$_2$ (5.0 g, 15.7 mmol) in anhydrous CH$_2$Cl$_2$ (500 mL) at 0° C. was added trimethylsilyl cyanide (13.7 g, 138 mmol). The reaction mixture was allowed to warm to room temperature and stirred overnight. Water (250 mL) was added, and the layers were separated. The aqueous layer was extracted with CH$_2$Cl$_2$ (2× 300 mL). The combined organic extracts were dried (Na$_2$SO$_4$), filtered, and concentrated in vacuo to afford the sub-title compound (16.9 g, 83%) as a yellow oil that was used without further purification.

R$_f$=0.42 (3:1 Hex:EtOAc)
$^1$H-NMR (300 MHz, CDCl$_3$) δ 7.06 (s, 1H), 6.86 (s, 2H), 5.40 (s, 1H), 0.30 (s, 9H), 0.24 (s, 9H).

(ii) Ph(3-Cl)(5-OH)—(R,S)CH(OH)C(O)OH

A solution of Ph(3-Cl)(5-OTMS)—(R,S)CH(OTMS)CN (22.6 g, 68.8 mmol; see step (i) above) in concentrated HCl (200 mL) was refluxed under nitrogen for 3 h. The reaction was cooled to 0° C. and basified slowly with 2N NaOH. The mixture was washed with Et$_2$O (3× 100 mL) to remove the organic impurities. The aqueous layer was acidified with 2N HCl and extracted with EtOAc (3× 200 mL). The combined organic extracts were dried (Na$_2$SO$_4$), filtered, and concentrated in vacuo to afford the sub-title compound (9.3 g, 67%) as a brown oil that was used without further purification.

R$_f$=0.23 (6:3:1 CHCl$_3$:MeOH:concentrated NH$_4$OH)
$^1$H NMR (300 MHz, CD$_3$OD) δ 7.05 (s, 1H), 6.94 (s, 1H), 6.73 (s, 1H), 5.03 (s, 1H).

(iii) Ph(3-Cl)(5-OH)—(R,S)CH(OH)C(O)OEt

To a solution of Ph(3-Cl)(5-OH)—(R,S)CH(OH)C(O)OH (9.3 g, 46.0 mmol; see step (ii) above) in absolute EtOH (200 mL) was added concentrated sulfuric acid (0.25 mL) and the reaction was refluxed under nitrogen for 4 h. The reaction was cooled to 0° C. and solid NaHCO$_3$ (0.2 g) was added. The reaction was concentrated in vacuo and partitioned with saturated NaHCO$_3$ (100 mL) and Et$_2$O (3× 50 mL). The combined organic extracts were dried (Na$_2$SO$_4$), filtered, and concentrated in vacuo to give the sub-title compound (6.9 g, 65%) as a yellow oil which was used without further purification.

R$_f$=0.62 (6:3:1 CHCl$_3$:MeOH:concentrated NH$_4$OH).
$^1$H NMR (300 MHz, CDCl$_3$) δ 6.99 (s, 1H), 6.81 (s, 2H), 5.07 (s, 1H), 4.16-4.32 (m, 2H), 1.23 (t, J=7 Hz, 3H).

(iv) Ph(3-Cl)(5-OCH$_2$F)—(R,S)CH(OH)C(O)OEt

To a solution of Ph(3-Cl)(5-OH)—(R,S)CH(OH)C(O)OEt (6.1 g, 26.8 mmol; see step (iii) above) in DMF (100 mL) in a sealed flask under nitrogen at 0° C. was added cesium carbonate (13.1 g, 40.2 mmol). The reaction mixture was stirred at 0° C. for 15 minutes followed by the addition of potassium iodide (0.5 g, 2.7 mmol). The reaction was cooled to −78° C. and chlorofluoromethane (18.4 g, 268 mmol) was bubbled into the vessel. The sealed flask was then allowed to warm to room temperature and stirred for 18 h. The reaction mixture was cooled to 0° C., vented carefully to remove any excess chlorofluoromethane, and partitioned with H$_2$O (20 mL) and Et$_2$O (3× 50 mL). The combined organics were washed with brine (2×50 mL), dried (Na$_2$SO$_4$), filtered and concentrated in vacuo. Flash chromatography on silica gel eluting with Hex:EtOAc (gradient from 9:1 to 3:1) afforded the sub-title compound (2.4 g, 35%) as a light yellow oil. Note: The compound is faintly uv-visible on TLC. It can be visualised by staining the TLC with bromocresol green.

R$_f$=0.46 (2:1 Hex:EtOAc)
$^1$H NMR (300 MHz, CDCl$_3$) δ 7.21 (s, 1H), 7.08 (s, 1H), 7.05 (s, 1H), 5.70 (d, J$_{H-F}$=54 Hz, 2H), 5.12 (d, J=5 Hz, 1H), 3.80-4.35 (m, 2H), 3.50 (d, J=5 Hz, 1H), 1.26 (t, J=7 Hz, 3H).

(v) Ph(3-Cl)(5-OCH$_2$F)—(R,S)CH(OH)C(O)OH

To a solution of Ph(3-Cl)(5-OCH$_2$F)—(R,S)CH(OH)C(O)OEt (1.8 g, 6.8 mmol; see step (iv) above) in H$_2$O:THF (30 mL, 1:2) at 0° C. under nitrogen was added lithium hydroxide monohydrate (0.40 g, 10.3 mmol). The mixture was stirred at 0° C. for 2 h. The reaction mixture was concentrated in vacuo and partitioned with H$_2$O (5 mL) and Et$_2$O (2× 20 mL). The aqueous layer was acidified carefully with 0.2N HCl at 0° C. and extracted with EtOAc (3× 30 mL). The combined organics were dried (Na$_2$SO$_4$), filtered and concentrated in vacuo to afford the sub-title compound (1.4 g, 87%) as a colourless oil which solidified to a white solid upon standing.

R$_f$=0.43 (6:2:1 CHCl$_3$:MeOH:Et$_3$N)
$^1$H NMR (300 MHz, CD$_3$OD) δ 7.24 (s, 1H), 7.17 (s, 1H), 7.07 (s, 1H), 5.78 (d, J$_{H-F}$=54 Hz, 2H), 5.13 (s, 1H).

(vi) Ph(3-Cl)(5-OCH$_2$F)—(R)CH(OH)C(O)OH (a)
and Ph(3-Cl)(5-OCH$_2$F)—(S)CH(OAc)C(O)OH (b)

A mixture of Ph(3-Cl)(5-OCH$_2$F)—(R,S)CH(OH)C(O)OH (3.2 g, 13.9 mmol; see step (v) above) and Lipase PS "Amano" (1.9 g) in vinyl acetate (150 mL) and MTBE (150 mL) was heated at 70° C. under a nitrogen atmosphere for 3 d. The reaction mixture was cooled, filtered through Celite® and the filter cake washed with EtOAc. The filtrate was concentrated in vacuo and subjected to flash chromatography on a silica gel eluting with CHCl$_3$:MeOH:Et$_3$N (15:1:0.5) to afford the triethylamine salt of the sub-title compound (a) (0.50 g, 21%) that was used without neutralisation. In addition, the triethylamine salt of the sub-title compound (b) (0.46 g, 20%) was obtained.

Data for Sub-Title Compound (a):

$R_f$=0.19 (15:1:0.5 CHCl$_3$:MeOH:Et$_3$N)

$^1$H NMR (300 MHz, CD$_3$OD) δ 7.26 (s, 1H), 7.18 (s, 1H), 6.97 (s, 1H), 5.74 (d, $J_{H-F}$=54 Hz, 2H), 4.81 (s, 1H), 3.17 (q, J=7 Hz, 6H), 1.28 (t, J=7 Hz, 9H).

Data for Sub-Title Compound (b)

$R_f$=0.33 (15:1:0.5 CHCl$_3$:MeOH:Et$_3$N)

$^1$H NMR (300 MHz, CD$_3$OD) δ 7.28 (s, 1H), 7.19 (s, 1H), 7.09 (s, 1H), 5.76 (d, $J_{H-F}$=54 Hz, 2H), 5.75 (s, 1H), 3.17 (q, J=7 Hz, 6H), 2.16 (s, 3H), 1.28 (t, J=7 Hz, 9H).

(vii) Ph(3-Cl)(5-OCH$_2$F)—(R)CH(OH)C(O)-Aze-Pab(Teoc)

To a solution of the triethylamine salt of Ph(3-Cl)(5-OCH$_2$F)—(R)CH(OH)C(O)OH (0.50 g, 1.50 mmol; see step (vi) above) and HAze-Pab(Teoc).HCl (0.87 g, 1.90 mmol) in dry DMF (15 mL) under nitrogen at 0° C. was added PyBOP (0.85 g, 2.60 mmol) and DIPEA (0.48 g, 3.70 mmol). The reaction was allowed to warm to room temperature and stirred overnight. The reaction mixture was concentrated in vacuo and flash chromatographed twice on silica gel, eluting first with CHCl$_3$:EtOH (9:1) and second with EtOAc:EtOH (20:1) to afford the sub-title compound (0.23 g, 26%) as a crushable white foam.

Mp: 88-92° C.

$R_f$=0.61 (9:1 CHCl$_3$:EtOH)

$^1$H NMR (300 MHz, CD$_3$OD, complex mixture of rotamers) δ 7.81 (d, J=8 Hz, 2H), 7.40-7.42 (m, 2H), 7.06-7.23 (m, 3H), 5.76 (d, $J_{H-F}$=51 Hz, 2H), 5.10-5.16 and 4.77-4.83 (m, 2H), 3.80-4.49 (m, 6H), 2.30-2.53 (m, 2H), 1.08 (t, J=7 Hz, 2H), 0.08 (s, 9H).

APCI-MS (M+1)=593 m/z (viii) Ph(3-Cl)(5-OCH$_2$F)—(R)CH(OH)C(O)-Aze-Pab×TFA

Ph(3-Cl)(5-OCH$_2$F)—(R)CH(OH)C(O)-Aze-Pab(Teoc) (0.051 g, 0.086 mmol; see step (vii) above), was dissolved in 3 mL of TFA and allowed to react for 20 min. TFA was evaporated and the residue was freeze dried from water/acetonitrile. The product was 95% pure with 5% of defluoromethylated material. Attempts to purify it by preparative RPLC with CH$_3$CN:0.1M NH$_4$OAc failed, and the material, partially as an acetate, was dissolved in 5 mL of TFA, evaporated and freeze dried to yield 26 mg (51%) of the title compound as its TFA salt. Purity: 95%.

$^1$H-NMR (600 MHz; CD$_3$OD) rotamers: δ 7.8-7.7 (m, 2H), 7.6-7.5 (m, 2H), 7.21 (s, 1H, major rotamer), 7.17 (s, 1H, minor rotamer), 7.13 (s, 1H, major rotamer), 7.09 (s, 1H, minor rotamer), 7.07 (m, 1H, major rotamer), 7.04 (m, 1H, minor rotamer), 5.73 (d, 2H), 5.18 (m, 1H, minor rotamer), 5.16 (s, 1H, major rotamer), 5.09 (s, 1H, minor rotamer), 4.78 (m, 1H, minor rotamer), 4.56 (d, 1H, major rotamer), 4.50 (d, 1H, minor rotamer), 4.46 (d, 1H, minor rotamer), 4.45 (d, 1H, major rotamer), 4.35 (m, 1H, major rotamer), 4.14 (m, 1H, major rotamer), 4.05 (m, 1H, minor rotamer), 3.97 (m, 1H, minor rotamer), 2.68 (m, 1H, major rotamer), 2.52 (m, 1H, major rotamer), 2.28 (m, 1H, major rotamer), 2.19 (m, 1H, minor rotamer).

$^{13}$C-NMR (150 MHz; CD$_3$OD): (carbonyl and/or amidine carbons, rotamers) δ 173.9, 17.3.3, 172.9, 168.2.

ESI-MS+: (M+1)=449 (m/z)

EXAMPLE 20

Ph(3-Cl)(5-OCH$_2$F)—(R)CH(OH)C(O)-Aze-Pab (OMe)

To a solution of the triethylamine salt of Ph(3-Cl)(5-OCH$_2$F)—(R)CH(OH)C(O)OH (0.60 g, 1.80 mmol; see Example 19(vi)) and HAze-Pab(OMe).2HCl (0.79 g, 2.30 mmol) in DMF (15 mL) under nitrogen at 0° C. was added PyBOP (1.04 g, 1.90 mmol) and DIPEA (0.58 g, 4.50 mmol). The reaction was allowed to warm to room temperature and stirred overnight. The reaction mixture was concentrated in vacuo and flash chromatographed three times on silica gel, eluting first with CHCl$_3$:EtOH (9:1) and then twice with EtOAc:EtOH (20:1) to afford the title compound (0.22 g, 26%) as a crushable white foam.

Mp: 66-70° C.

$R_f$=0.45 (9:1 CHCl$_3$:EtOH)

$^1$H NMR (300 MHz, CD$_3$OD, complex mixture of rotamers) δ 7.59 (d, J=8 Hz, 2H), 7.32 (d, J=7 Hz, 2H), 7.06-7.23 (m, 3H), 5.75 (s, $J_{H-F}$=54 Hz, 1H), 5.10-5.16 and 4.78-4.84 (m, 2H), 4.11-4.45 (m, 4H), 3.80 (s, 3H), 2.10-2.75 (m, 2H).

$^{13}$C-NMR (150 MHz; CD$_3$OD): (carbonyl and/or amidine carbons, rotamers) δ 173.0, 170.8, 170.7, 152.5.

APCI-MS: (M+1)=479 m/z

EXAMPLE 21

Ph(3-Cl)(5-OCH$_2$H$_2$F)—(R)CH(OH)C(O)-Aze-Pab×TFA (i) (2-Monofluoroethyl)methanesulfonate To a magnetically stirred solution of 2-fluoroethanol (5.0 g, 78.0 mmol) in CH$_2$Cl$_2$ (90 ml) under nitrogen at 0° C. was added triethylamine (23.7 g, 234 mmol) and methanesulfonyl chloride (10.7 g, 93.7 mmol). The mixture was stirred at 0° C. for 1.5 h, diluted with CH$_2$Cl$_2$ (100 mL) and washed with 2N HCl (100 mL). The aqueous layer was extracted with CH$_2$Cl$_2$ (50 mL) and the combined organic extracts washed with brine (75 mL), dried (Na$_2$SO$_4$), filtered and concentrated in vacuo to afford the sub-title compound (9.7 g, 88%) as a yellow oil which was used without further purification.

$^1$H NMR (300 MHz, CDCl$_3$) δ 4.76 (t, J=4 Hz, 1H), 4.64 (t, J=4 Hz, 1H), 4.52 (t, J=4 Hz, 1H), 4.43 (t, J=4 Hz, 1H), 3.09 (s, 3H).

(ii) 3-Chloro-5-monofluoroethoxybenzaldehyde

To a solution of 3-chloro-5-hydroxybenzaldehyde (8.2 g, 52.5 mmol; see Example 1(ii) above) and potassium carbonate (9.4 g, 68.2 mmol) in DMF (10 mL) under nitrogen was added a solution of (2-monofluoroethyl)methanesulfonate (9.7 g, 68.2 mmol; see step (i) above) in DMF (120 mL) dropwise at room temperature. The mixture was heated to 100° C. for 5 h and then stirred overnight at room temperature. The reaction was cooled to 0° C., poured into ice-cold 2N HCl and extracted with EtOAc. The combined organic extracts were washed with brine, dried (Na$_2$SO$_4$), filtered and concentrated in vacuo. The brown oil was chromatographed on silica gel eluting with Hex:EtOAc (4:1) to afford the sub-title compound (7.6 g, 71%) as a yellow oil.

$^1$H NMR (300 MHz, CDCl$_3$) δ 9.92 (s, 1H), 7.48 (s, 1H), 7.32 (s, 1H), 7.21 (s, 1H), 4.87 (t, J=4 Hz, 1H), 4.71 (t, J=3 Hz, 1H), 4.33 (t, J=3 Hz, 1H), 4.24 (t, J=3 Hz, 1H).

(iii) Ph(3-Cl)(5-OCH₂CH₂F)—(R,S)CH(OTMS)CN

To a solution of 3-chloro-5-monofluoroethoxybenzaldehyde (7.6 g, 37.5 mmol; see step (ii) above) and zinc iodide (3.0 g, 9.38 mmol) in CH₂Cl₂ (310 mL) was added trimethylsilyl cyanide (7.4 g, 75.0 mmol) dropwise at 0° C. under nitrogen. The mixture was stirred at 0° C. for 3 h and at room temperature overnight. The reaction was diluted with H₂O (300 mL), the organic layer was separated, dried (Na₂SO₄), filtered and concentrated in vacuo to afford the sub-title compound (10.6 g, 94%) as a brown oil that was used without further purification or characterisation.

(iv) Ph(3-Cl)(5-OCH₂CH₂F)—(R,S)CH(OH)C(O)OH

Concentrated hydrochloric acid (100 mL) was added to Ph(3-Cl)(5-OCH₂CH₂F)—(R,S)CH(OTMS)CN (10.6 g, 5.8 mmol; see step (iii) above) and the solution stirred at 100° C. for 3 h. After cooling to room temperature, the reaction was further cooled to 0° C., basified slowly with 3N NaOH (~300 mL) and washed with Et₂O (3× 200 mL). The aqueous layer was acidified with 2N HCl (80 mL) and extracted with EtOAc (3× 300 mL). The combined EtOAc extracts were dried (Na₂SO₄), filtered and concentrated in vacuo to afford the sub-title compound (8.6 g, 98%) as a pale yellow solid that was used without further purification.

$R_f$=0.28 (90:8:2 CHCl₃:MeOH:concentrated NH₄OH)
¹H NMR (300 MHz, CD₃OD) δ 7.09 (s, 1H), 7.02 (s, 1H), 6.93 (s, 1H), 5.11 (s, 1H), 4.77-4.81 (m, 1H), 4.62-4.65 (m, 1H), 4.25-4.28 (m, 1H), 4.15-4.18 (m, 1H).

(v) Ph(3-Cl)(5-OCH₂CH₂F)—(S)CH(OAc)C(O)OH (a) and Ph(3-Cl)(5-OCH₂CH₂F)—(R)CH(OH)C(O)OH (b)

A solution of Ph(3-Cl)(5-OCH₂CH₂F)—(R,S)CH(OH)C(O)OH (8.6 g, 34.5 mmol; see step (iv) above) and Lipase PS "Amano" (4.0 g) in vinyl acetate (250 mL) and MTBE (250 mL) was heated at 70° C. under nitrogen for 3 d. The reaction was cooled to room temperature and the enzyme removed by filtration through Celite®. The filter cake was washed with EtOAc and the filtrate concentrated in vacuo. Chromatography on silica gel eluting with CHCl₃:MeOH:Et₃N (90:8:2) afforded the triethylamine salt of sub-title compound (a) as a yellow oil. In addition, the triethylamine salt of sub-title compound (b) (4.0 g) was obtained. The salt of sub-title compound (b) was dissolved in H₂O (250 mL), acidified with 2N HCl and extracted with EtOAc (3× 200 mL). The combined organic extracts were dried (Na₂SO₄), filtered and concentrated in vacuo to yield the sub-title compound (b) (2.8 g, 32%) as a yellow oil.

Data for Sub-Title Compound (b):
$R_f$=0.28 (90:8:2 CHCl₃:MeOH:concentrated NH₄OH)
¹H NMR (300 MHz, CD₃OD) δ 7.09 (s, 1H), 7.02 (s, 1H), 6.93 (s, 1H), 5.11 (s, 1H), 4.77-4.81 (m, 1H), 4.62-4.65 (m, 1H), 4.25-4.28 (m, 1H), 4.15-4.18 (m, 1H).

(vi) Ph(3-Cl)(5-OCH₂CH₂F)—(R)CH(OH)C(O)-Aze-Pab(Teoc)

To a solution of Ph(3-Cl)(5-OCH₂CH₂F)—(R)CH(OH)C(O)OH (940 mg, 3.78 mmol; see step (v) above) in DMF (30 mL) under nitrogen at 0° C. was added HAze-Pab(Teoc).HCl (2.21 g, 4.91 mmol), PyBOP (2.16 g, 4.15 mmol), and DIPEA (1.22 g, 9.45 mmol). The reaction was stirred at 0° C. for 2 h and then at room temperature for 4 h. The mixture was concentrated in vacuo and the residue chromatographed twice on silica gel, eluting first with CHCl₃:EtOH (15:1) and second with EtOAc:EtOH (20:1) to afford the sub-title compound (450 mg, 20%) as a crushable white foam.

Mp: 80-88° C.
$R_f$=0.60 (10:1 CHCl₃:EtOH)
¹H NMR (300 MHz, CD₃OD, complex mixture of rotamers) δ 7.79 (d, J=8 Hz, 2H), 7.42 (d, J=8 Hz, 2H), 7.05-7.08 (m, 1H), 6.93-6.99 (m, 2H), 5.08-5.13 (m, 1H), 4.75-4.80 (m, 2H), 4.60-4.68 (m, 1H), 3.95-4.55 (m, 8H), 2.10-2.75 (m, 2H), 1.05-1.11 (m, 2H), 0.08 (s, 9H).
APCI-MS: (M+1)=607 m/z.

(vii) Ph(3-Cl)(5-OCH₂CH₂F)—(R)CH(OH)C(O)-Aze-Pab×TFA

Ph(3-Cl)(5-OCH₂CH₂F)—(R)CH(OH)C(O)-Aze-Pab (Teoc) (0.357 g, 0.589 mmol; see step (vi) above), was dissolved in 10 mL of TFA and allowed to react for 40 min. TFA was evaporated and the residue was freeze dried from water/acetonitrile to yield 0.33 g (93%) of the title compound as its TFA salt.

¹H-NMR (600 MHz; CD₃OD) rotamers: δ 7.8-7.7 (m, 2H), 7.54 (d, 2H), 7.08 (s, 1H, major rotamer), 7.04 (s, 1H, minor rotamer), 6.99 (s, 1H, major rotamer), 6.95 (s, 1H), 6.92 (s, 1H, minor rotamer), 5.18 (m, 1H, minor rotamer), 5.14 (s, 1H, major rotamer), 5.08 (s, 1H, minor rotamer), 4.80 (m, 1H, major rotamer), 4.73 (m, 1H), 4.65 (m, 1H), 4.6-4.4 (m, 2H), 4.35 (m, 1H, major rotamer), 4.21 (doublet of multiplets, 2H), 4.12 (m, 1H, major rotamer), 4.06 (m, 1H, minor rotamer), 3.99 (m, 1H, minor rotamer), 2.69 (m, 1H, minor rotamer), 2.53 (m, 1H, major rotamer), 2.29 (m, 1H, major rotamer), 2.14 (m, 1H, minor rotamer).
¹³C-NMR (150 MHz; CD₃OD): (carbonyl and/or amidine carbons) δ 172.8, 172.1, 167.4.
ESI-MS+: (M+1)=463 (m/z)

EXAMPLE 22

Ph(3-Cl)(5-OCH₂CH₂F)—(R)CH(OH)C(O)-Aze-Pab(OMe)

To a solution of Ph(3-Cl)(5-OCH₂CH₂F)—(R)CH(OH)C(O)OH (818 mg, 3.29 mmol; see Example 21(v) above) in DMF (30 mL) under nitrogen at 0° C. was added HAze-Pab(OMe).2HCl (1.43 g, 4.27 mmol), PyBOP (1.89 g, 3.68 mmol), and DIPEA (1.06 g, 8.23 mmol). The reaction was stirred at 0° C. for 2 h and then at room temperature overnight. The mixture was concentrated in vacuo and the residue chromatographed two times on silica gel, eluting first with CHCl₃:EtOH (15:1) and second with EtOAc:EtOH (20:1) to afford the title compound (880 mg, 54%) as a crushable white foam.

Mp: 65-72° C.
$R_f$=0.60 (10:1 CHCl₃:EtOH)
¹H NMR (300 MHz, CD₃OD, complex mixture of rotamers) δ 7.58-7.60 (d, J=8 Hz, 2H), 7.34 (d, J=7 Hz, 2H), 7.05-7.08 (m, 2H), 6.95-6.99 (m, 1H), 5.08-5.13 (m, 1H), 4.77-4.82 (m, 1H), 4.60-4.68 (m, 1H), 3.99-4.51 (m, 7H), 3.82 (s, 3H), 2.10-2.75 (m, 2H).
¹³C-NMR (150 MHz; CD₃OD): (carbonyl and/or amidine carbons) δ 173.3, 170.8, 152.5.
APCI-MS: (M+1)=493 m/z.

EXAMPLE 23

Ph(3-Cl)(5-OCH(CH₂F)₂)—(R)CH(OH)C(O)-Aze-Pab×TFA

(i) 1,3-Difluoroisopropyl methanesulfonate

To a magnetically stirred solution of 1,3-difluoro-2-propanol (7.0 g, 72.8 mmol) in CH₂Cl₂ (100 mL) under nitrogen at 0° C. was added triethylamine (22.1 g, 219 mmol) and methanesulfonyl chloride (10.0 g, 87.4 mmol). The mixture was stirred at 0° C. for 3 h. The mixture was washed with 2N HCl (150 mL) and the layers were separated. The aqueous layer was extracted with $CH_2Cl_2$ (200 mL) and the combined organic extracts washed with brine (100 mL), dried ($Na_2SO_4$), filtered and concentrated in vacuo to afford the sub-title compound (11.5 g, 91%) as a yellow oil which was used without further purification.

$^1$H NMR (300 MHz, $CDCl_3$) δ 4.97-5.08 (m, 1H), 4.75-4.77 (m, 2H), 4.59-4.61 (m, 2H), 3.12 (s, 3H).

(ii) Ph(3-Cl)(5-OCH($CH_2F)_2$)CHO

To a solution of 3-chloro-5-hydroxybenzaldehyde (8.0 g, 50.7 mmol; see Example 1(ii) above) and potassium carbonate (9.1 g, 66.0 mmol) in DMF (75 mL) under nitrogen was added a solution of 1,3-difluoroisopropyl methanesulfonate (11.5 g, 66.0 mmol; see step (i) above) in DMF (75 mL) dropwise at room temperature. The mixture was heated to 110° C. for 18 h. The reaction was cooled to 0° C., poured into ice-cold 2N HCl (200 mL) and extracted with EtOAc (3× 250 mL). The combined organic extracts were dried ($Na_2SO_4$), filtered and concentrated in vacuo. The brown oil was chromatographed on silica gel eluting with Hex:EtOAc (4:1) to afford the sub-title compound (4.4 g, 37%) as a yellow oil.

$^1$H NMR (300 MHz, $CDCl_3$) δ 9.92 (s, 1H), 7.51 (s, 1H), 7.36 (s, 1H), 7.26 (s, 1H), 4.70-4.89 (m, 3H), 4.63-4.68 (m, 2H).

(iii) Ph(3-Cl)(5-OCH($CH_2F)_2$)—(R,S)CH(OTMS)CN

To a solution of Ph(3-Cl)(5-OCH($CH_2F)_2$)CHO (4.4 g, 18.7 mmol; see step (ii) above) and zinc iodide (1.5 g, 4.67 mmol) in $CH_2Cl_2$ (200 mL) at 0° C. under nitrogen was added trimethylsilyl cyanide (3.7 g, 37.3 mmol) dropwise. The mixture was stirred at 0° C. for 3 h and overnight at room temperature, then diluted with $H_2O$ (200 mL). The organic layer was separated, dried ($Na_2SO_4$), filtered and concentrated in vacuo to afford the sub-title compound (5.5 g, 87%) as a brown oil that was used without further purification.

$^1$H NMR (300 MHz, $CDCl_3$) δ 7.12 (s, 1H), 7.00 (s, 2H), 5.42 (s, 1H), 4.70-4.80 (m, 3H), 4.59-4.64 (m, 2H), 0.26 (s, 9H).

(iv) Ph(3-Cl)(5-OCH($CH_2F)_2$)—(R,S)CH(OH)C(O)OH

Concentrated hydrochloric acid (50 mL) was added to Ph(3-Cl)(5-OCH($CH_2F)_2$)—(R,S)CH(OTMS)CN (5.5 g, 16.3 mmol; see step (iii) above) and the solution stirred at 100° C. for 1.5 h. After cooling to room temperature, the reaction was further cooled to 0° C., basified slowly with 3N NaOH (~200 mL) and washed with $Et_2O$ (3× 200 mL). The aqueous layer was acidified with 2N HCl (75 mL) and extracted with EtOAc (3× 200 mL). The combined EtOAc extracts were dried ($Na_2SO_4$), filtered and concentrated in vacuo to afford the sub-title compound (4.6 g, 100%) as a brown oil that was used without further purification.

$^1$H NMR (300 MHz, $CD_3OD$) δ 7.14 (s, 1H), 7.08 (s, 1H), 7.02 (s, 1H), 5.12 (s, 1H), 4.70-4.90 (m, 3H), 4.52-4.67 (m, 2H).

(v) Ph(3-Cl)(5-OCH($CH_2F)_2$)—(S)CH(OAc)C(O)OH (a) and Ph(3-Cl)(5-OCH($CH_2F)_2$)—(R)CH(OH)C(O)OH (b)

A solution of Ph(3-Cl)(5-OCH($CH_2F)_2$)—(R,S)CH(OH)C(O)OH (4.6 g, 16.4 mmol; see step (iv) above) and Lipase PS "Amano" (3.0 g) in vinyl acetate (150 mL) and MTBE (150 mL) was heated at 70° C. under nitrogen for 2.5 d. The reaction was cooled to room temperature, the enzyme removed by filtration through Celite®. The filter cake was washed with EtOAc and the filtrate concentrated in vacuo. Chromatography on silica gel eluting with $CHCl_3$:MeOH:$Et_3N$ (90:8:2) afforded the triethylamine salt of the sub-title compound (a) as a yellow oil. In addition, the triethylamine salt of the sub-title compound (b) (2.2 g) was obtained and the salt was dissolved in $H_2O$ (100 mL), acidified with 2N HCl and extracted with EtOAc (3× 200 mL). The combined organic extracts were dried ($Na_2SO_4$), filtered and concentrated in vacuo to yield the sub-title compound (b) (1.4 g, 29%) as a is yellow oil.

Data for Sub-Title Compound (b):

$^1$H NMR (300 MHz, $CD_3OD$) δ 7.14 (s, 1H), 7.08 (s, 1H), 7.02 (s, 1H), 5.12 (s, 1H), 4.70-4.90 (m, 3H), 4.52-4.67 (m, 2H).

(vi) Ph(3-Cl)(5-OCH($CH_2F)_2$)—(R)CH(OH)C(O)-Aze-Pab(Teoc)

To a solution of Ph(3-Cl)(5-OCH($CH_2F)_2$)—(R)CH(OH)C(O)OH (824 mg, 2.94 mmol; see step (v) above) in DMF (30 mL) under nitrogen at 0° C. was added HAze-Pab(Teoc).HCl (1.71 g, 3.81 mmol), PyBOP (1.68 g, 3.23 mmol), and DIPEA (949 mg, 7.34 mmol). The reaction was stirred at 0° C. for 2 h and then at room temperature overnight. The mixture was concentrated in vacuo and the residue chromatographed twice on silica gel, eluting first with $CHCl_3$:EtOH (15:1), and second with EtOAc:EtOH (20:1) to afford the sub-title compound (720 mg, 38%) as a crushable white foam.

Mp: 78-84° C.

$R_f$=0.62 (10:1 $CHCl_3$:EtOH)

$^1$H NMR (300 MHz, $CD_3OD$, complex mixture of rotamers) δ 7.79 (d, J=8 Hz, 2H), 7.42 (d, J=8 Hz, 2H), 7.00-7.12 (m, 3H), 5.08-5.20 (m, 1H), 3.97-4.80 (m, 12H), 2.10-2.75 (m, 2H), 1.05-1.11 (m, 2H), 0.08 (s, 9H).

APCI-MS: (M+1)=639 m/z.

(vii) Ph(3-Cl)(5-OCH($CH_2F)_2$)—(R)CH(OH)C(O)-Aze-Pab×TFA

Ph(3-Cl)(5-OCH($CH_2F)_2$)—(R)CH(OH)C(O)-Aze-Pab(Teoc) (0.129 g, 0.202 mmol; see step (vi) above), was dissolved in 3 mL of TFA and allowed to react for 20 min. TFA was evaporated and the residue was freeze dried from water/acetonitrile to yield 0.123 g (100%) of the title compound as its TFA salt.

$^1$H-NMR (400 MHz; $CD_3OD$) rotamers: δ 7.8-7.7 (m, 2H), 7.55 (d, 2H), 7.2-7.0 (m, 3H), 5.18 (m, 1H, minor rotamer), 5.15 (s, 1H, major rotamer), 5.08 (s, 1H, minor rotamer), 4.80 (m, 1H, major rotamer partly obscured by the $CD_3OH$ peak), 4.75-4.4 (m, 7H), 4.38 (m, 1H, major rotamer), 4.15 (m, 1H, major rotamer), 4.1-3.9 (m, 2H, 2 signals from minor rotamer), 2.70 (m, 1H, minor rotamer), 2.53 (m, 1H, major rotamer), 2.30 (m, 1H, major rotamer), 2.15 (m, 1H, minor rotamer).

$^{13}$C-NMR (100 MHz; $CD_3OD$): (carbonyl and/or amidine carbons, rotamers) δ 172.9, 172.6, 172.2, 171.7, 167.1.

ESI-MS+: (M+1)=495 (m/z)

EXAMPLE 24

Ph(3-Cl)(5-OCH($CH_2F)_2$)—(R)CH(OH)C(O)-Aze-Pab(OMe)

To a solution of Ph(3-Cl)(5-OCH($CH_2F)_2$)—(R)CH(OH)C(O)OH (513 mg, 1.83 mmol; see Example 23(v) above) in DMF (30 mL) under nitrogen at 0° C. was added HAze-Pab (OMe).2HCl (797 mg, 2.38 mmol), PyBOP (1.04 g, 2.01 mmol), and DIPEA (591 mg, 4.57 mmol). The reaction was stirred at 0° C. for 2 h and then at room temperature overnight. The mixture was concentrated in vacuo and the residue chromatographed two times on silica gel, eluting first with $CHCl_3$:EtOH (15:1) and second with EtOAc:EtOH (20:1) to afford the title compound (370 mg, 39%) as a crushable white foam.

Mp: 58-63° C.

$R_f$=0.66 (10:1 $CHCl_3$:EtOH)

$^1$H NMR (300 MHz, $CD_3OD$, complex mixture of rotamers) δ 7.58-7.60 (d, J=8 Hz, 2H), 7.34 (d, J=8 Hz, 2H), 7.00-7.12 (m, 3H), 5.08-5.20 (m, 1H), 4.65-4.82 (m, 3H), 4.28-4.65 (m, 5H), 3.92-4.18 (m, 2H), 3.82 (s, 3H), 2.10-2.75 (m, 2H).

$^{13}$C-NMR (150 MHz; $CD_3OD$): (carbonyl and/or amidine carbons) δ 173.2, 170.8, 152.5.

APCI-MS: (M+1)=525 m/z.

EXAMPLE 25

Ph(3-F)(5-OCHF$_2$)—(R)CH(OH)C(O)-Aze-Pab× TFA (i) 1-Bromo-3-fluoro-5-benzyloxybenzene Sodium hydride (60% dispersion in oil, 24.0 g, 0.48 mol) was added portionwise to a stirred solution of anhydrous benzyl alcohol (64.5 g, 0.60 mol) in THF (1.0 L). After the mixture was stirred for 1 h, a solution of 1-bromo-3,5-difluorobenzene (76.8 g, 0.40 mmol) in THF (100 mL) was added dropwise over a period of 1 h. The reaction was stirred at room temperature for 2 d. Water (400 mL) was added and the THF was removed in vacuo. The aqueous layer was extracted with hexane (3× 150 mL). The combined organic extracts were washed with 2N NaOH (2× 100 mL) then, dried ($Na_2SO_4$), filtered and concentrated in vacuo to afford the sub-title compound (110.7 g, 98%) as a light yellow oil that was used without further purification.

$R_f$=0.47 (Hex)

$^1$H NMR (300 MHz, $CDCl_3$) δ 7.36-7.41 (m, 5H), 6.94 (bs, 1H), 6.87 (d, $J_{H-F}$=8 Hz, 1H), 6.63 (d, $J_{H-F}$=10 Hz, 1H), 5.03 (s, 2H).

(ii) 3-Bromo-5-fluorophenol

To a solution of 1-bromo-3-fluoro-5-benzyloxybenzene (110.0 g, 0.39 mol; see step (i) above) and N,N-dimethylaniline (474.0 g, 3.92 mol) in anhydrous $CH_2Cl_2$ (1.0 L) at 0° C. was added aluminium chloride (156.0 g, 1.17 mol). After 10 min, the ice bath was removed and the stirring was continued for 2 h. The reaction was quenched by the cautious addition of 3N HCl (600 mL). The layers were separated, and the aqueous layer was extracted with $CH_2Cl_2$ (2× 150 mL). The combined organic extracts were washed with 2N HCl (250 mL) and $H_2O$ (3× 250 mL). To the organic layer was added 15% KOH (500 mL), and the layers were separated. The organic layer was further extracted with 2 N KOH (2× 70 mL). The combined aqueous layers were washed with $CH_2Cl_2$ (3× 100 mL) and then acidified with 4N HCl. The aqueous layer was extracted with $Et_2O$ (3× 125 mL) then, the combined $Et_2O$ extracts were dried ($Na_2SO_4$), filtered and concentrated in vacuo to afford the sub-title compound (69.0 g, 92%) as a brown oil that was used without further purification.

Mp: 33-35° C.

$R_f$=0.25 ($CHCl_3$)

$^1$H NMR (300 MHz, DMSO-$d_6$) δ 10.38 (s, 1H), 6.90 (dd, $J_{H-F}$=11 Hz, J=2 Hz, 1H), 6.81 (s, 1H), 6.59 (dt, $J_{H-F}$=11 Hz, J=2 Hz, 1H).

APCI-MS: (M−1)=189 m/z (iii) 1-Bromo-3-fluoro-5-difluoromethoxybenzene

A mixture of 3-bromo-5-fluorophenol (6.1 g, 31.0 mmol; see step (ii) above) and chlorodifluoromethane (13.0 g, 150.0 mmol) in i-PrOH (100 mL) and 30% KOH (80 mL) was heated in a sealed flask for 18 h at 80-85° C. The reaction mixture was cooled to room temperature and the layers were separated. The organic layer was concentrated in vacuo to afford a colourless oil. The aqueous layer was extracted with $Et_2O$ (3× 30 mL). The crude oil and the combined organic extracts were washed with 2N NaOH (3× 30 mL) and $H_2O$ (3× 30 mL). The organics were then dried ($Na_2SO_4$), filtered through a small silica gel plug, and concentrated in vacuo to afford the sub-title compound (6.1 g, 79%) as a colourless oil that was used without further purification.

$^1$H NMR (300 MHz, $CDCl_3$) δ 7.11-7.14 (m, 2H), 6.84 (dt, J=9 Hz, J=2 Hz, 1H), 6.50 (t, $J_{H-F}$=72 Hz, 1H).

(iv) 1-Fluoro-3-difluoromethoxy-5-vinylbenzene

Tri(butyl)vinylstannane (7.0 g, 22.2 mmol) was added to a suspension of 1-bromo-3-fluoro-5-difluoromethoxybenzene (4.9 g, 20.2 mmol; see step (iii) above), dichlorobis(triphenylphosphine)palladium(II) (1.42 g, 2.02 mmol) and anhydrous lithium chloride (0.90 g, 20.2 mmol) in THF (40 mL) under nitrogen at 65° C. and the mixture was stirred for 5 h. The reaction mixture was cooled to 0° C. and 1N NaOH (90 mL) was added. The biphasic mixture was vigorously stirred for 1 h then the layers were separated. The aqueous layer was extracted with $Et_2O$ (3× 70 mL). The combined organic layers were washed with 2N NaOH (2× 40 mL) and $H_2O$ (40 mL) then dried ($Na_2SO_4$), filtered and concentrated in vacuo. Flash chromatography on silica gel eluting with hexane afforded the sub-title compound (2.2 g, 57%) as a colourless oil.

$R_f$=0.47 (Hex)

$^1$H NMR (300 MHz, $CDCl_3$) δ 6.93-6.99 (m, 2H), 6.73-6.78 (m, 1H), 6.67 (dd, J=18 Hz, J=11 Hz, 1H), 6.51 (t, $J_{H-F}$=73 Hz, 1H), 5.77 (d, J=18 Hz, 1H), 5.36 (d, J=11 Hz, 1H).

(v) Ph(3-F)(5-OCHF$_2$)—(R)CH(OH)CH$_2$OH

2-Methyl-2-propanol (140 mL), $H_2O$ (140 mL), and AD-mix-β (39.2 g) were combined together and cooled to 0° C. 1-Fluoro-3-difluoromethoxy-5-vinylbenzene (5.0 g, 26.4 mmol; see step (iv) above) dissolved in a small amount of 2-methyl-2-propanol was added at once, and the heterogeneous slurry was vigorously stirred at 0° C. until TLC revealed the absence of the starting material. The reaction was quenched at 0° C. by addition of sodium sulfite (42.0 g) and then warmed to room temperature and stirred for 60 min. The reaction mixture was extracted with $Et_2O$ (3× 120 mL). The combined organic extracts were dried ($Na_2SO_4$), filtered and concentrated in vacuo. Flash chromatography on silica gel eluting with $CHCl_3$:EtOAc (3:2) afforded the sub-title compound (5.8 g, 98%) as a colourless oil.

$R_f$=0.41 (3:2 $CHCl_3$:EtOAc)

$^1$H NMR (300 MHz, $CDCl_3$) δ 6.96-6.99 (m, 2H), 6.77-6.82 (m, 1H), 6.51 (t, $J_{H-F}$=73 Hz, 1H), 4.79-4.85 (m, 1H), 3.76-3.84 (m, 1H), 3.58-3.66 (m, 1H), 2.66 (d, J=3 Hz, 1H), 2.00 (t, J=6 Hz, 1H).

HPLC Analysis: 89.2%, >99% ee, ChiralPak AD Column (95:5 Hex:EtOH mobile phase).

(vi) Ph(3-F)(5-OCHF$_2$)—(R)CH(OH)CH$_2$OTBS

A solution of Ph(3-F)(5-OCHF$_2$)—(R)CH(OH)CH$_2$OH (5.5 g, 24.7 mmol; see step (v) above), 4-(dimethylamino)pyridine (121 mg, 1.0 mmol) and triethylamine (3.0 g, 29.6 mmol) in anhydrous CH$_2$Cl$_2$ (100 mL) was cooled to 0° C. A 1.0 M solution of tert-butyldimethylsilyl chloride in CH$_2$Cl$_2$ (26.0 mL, 26.0 mmol) was added dropwise, and the reaction mixture was allowed to warm to room temperature and stirred overnight. Saturated ammonium chloride solution (60 mL) was added, and the layers were separated. The organic layer was washed with saturated ammonium chloride solution (60 mL) and H$_2$O (2× 35 mL) then dried (Na$_2$SO$_4$), filtered, and concentrated in vacuo. Flash chromatography on silica gel eluting with CHCl$_3$:Hex (3:1) afforded the sub-title compound (7.9 g, 85%) as a yellow oil.

R$_f$=0.47 (3:1 CHCl$_3$:Hex)

$^1$H NMR (300 MHz, CDCl$_3$) δ 6.95-6.98 (m, 2H), 6.76-6.79 (m, 1H), 6.51 (t, J$_{H-F}$=73 Hz, 1H), 4.71-4.74 (m, 1H), 3.75-3.80 (m, 1H), 3.48-3.54 (m, 1H), 2.99 (bs, 1H), 0.91 (s, 9H), 0.05 (s, 3H), 0.00 (s, 3H).

(vii) Ph(3-F)(5-OCHF$_2$)—(R)CH(OMEM)CH$_2$OTBS

To a solution of Ph(3-F)(5-OCHF$_2$)—(R)CH(OH)CH$_2$OTBS (7.9 g, 0.51 mmol; see step (vi) above) and DIPEA (4.9 g, 48.1 mmol) in anhydrous CH$_2$Cl$_2$ (50 mL) at 0° C. under nitrogen was added dropwise 2-methoxyethoxymethyl chloride (6.6 g, 48.1 mmol). The mixture was stirred for 24 h. Saturated ammonium chloride solution (70 mL) was added, and the layers were separated. The organic layer was washed with saturated ammonium chloride solution (70 mL) and H$_2$O (3× 60 mL) then dried (Na$_2$SO$_4$), filtered and concentrated in vacuo to afford the sub-title compound (8.8 g, 99%) as a yellow oil that was used without further purification.

R$_f$=0.41 (4:1 CHCl$_3$:EtOAc)

$^1$H NMR (300 MHz, CDCl$_3$) δ 7.20 (s, 1H), 7.06 (s, 1H), 7.02 (s, 1H), 6.50 (t, J$_{H-F}$=73 Hz, 1H), 4.79-4.81 (m, 1H), 4.66-4.68 (m, 2H), 3.47-3.82 (m, 6H), 3.36 (s, 3H), 0.85 (s, 9H), 0.01 (s, 3H), 0.00 (s, 3H).

(viii) Ph(3-F)(5-OCHF$_2$)—(R)CH(OMEM)CH$_2$OH

To a solution of Ph(3-F)(5-OCHF$_2$)—(R)CH(OMEM)CH$_2$OTBS (9.3 g, 21.9 mmol; see step (vii) above) in THF (60 mL) at room temperature was added a 1.0 M solution of tetrabutylammonium fluoride in THF (70.0 mL, 70.0 mmol) and the mixture was stirred overnight under nitrogen. The reaction was concentrated in vacuo. The yellow residue was dissolved in Et$_2$O (100 mL) and hexane (100 mL) and washed successively with saturated ammonium chloride solution (2× 150 mL) and H$_2$O (3× 70 mL). The organic layer was dried (Na$_2$SO$_4$), filtered and concentrated in vacuo. Flash chromatography on silica gel eluting with Hex:EtOAc (1:1) afforded the sub-title compound (4.2 g, 62%) as a yellow oil.

R$_f$=0.42 (1:1 Hex:EtOAc)

$^1$H NMR (300 MHz, CDCl$_3$) δ 6.91-6.95 (m, 2H), 6.75-6.81 (m, 1H), 6.51 (t, J$_{H-F}$=73 Hz, 1H), 4.80-4.82 (m, 1H), 4.70-4.74 (m, 2H), 3.88-3.93 (m, 1H), 3.67-3.71 (m, 3H), 3.53-3.56 (m, 2H), 3.39 (s, 3H), 2.96-2.99 (m, 1H).

(ix) Ph(3-F)(5-OCHF$_2$)—(R)CH(OMEM)C(O)OH

A solution of Ph(3-F)(5-OCHF$_2$)—(R)CH(OMEM)CH$_2$OH (4.2 g, 13.4 mmol; see step (viii) above) in acetone (100 mL) was added to an aqueous 5% NaHCO$_3$ solution (35 mL). This magnetically stirred heterogeneous mixture was cooled to 0° C. and potassium bromide (159 mg, 1.3 mmol) and 2,2,6,6-tetramethyl-1-piperidinyloxy, free radical (2.2 g, 14.1 mmol) were added. Sodium hypochlorite (5.25%, 30 mL) was then added dropwise over a period of 20 min while the mixture was vigorously stirred and maintained at 0° C. After 1 h, additional sodium hypochlorite (30 mL) and 5% NaHCO$_3$ solution (35 mL) were added and stirring was continued at 0° C. for 2 h. The acetone was removed in vacuo. The aqueous layer was washed with Et$_2$O (4× 40 mL). The aqueous layer was acidified to pH 3.5 with 10% citric acid and extracted with EtOAc (4× 50 mL). The combined EtOAc extracts were successively washed with H$_2$O (4× 30 mL) and brine (60 mL) then, dried (Na$_2$SO$_4$), filtered and concentrated in vacuo to afford the sub-title compound (4.3 g, 98%) as a colourless oil which was used without further purification.

R$_f$=0.74 (8.0:1.5:0.5 CHCl$_3$:MeOH:Et$_3$N)

$^1$H NMR (300 MHz, acetone-d$_6$) δ 7.16-7.18 (m, 2H), 7.16 (t, J$_{H-F}$=89 Hz, 1H), 7.00-7.03 (m, 1H), 5.30 (s, 1H), 4.88 (d, J=7 Hz, 1H), 4.80 (d, J=7 Hz, 1H), 3.54-3.75 (m, 2H), 3.46-3.49 (m, 2H), 3.28 (s, 3H).

(x) Ph(3-F)(5-OCHF$_2$)—(R)CH(OMEM)C(O)-Aze-Pab(Teoc)

To a solution of Ph(3-F)(5-OCHF$_2$)—(R)CH(OMEM)C(O)OH (1.1 g, 3.4 mmol; see step (ix) above) in DMF (20 mL) under nitrogen at 0° C. was added HAze-Pab(Teoc).HCl (2.0 g, 4.4 mmol), PyBOP (1.9 g, 3.7 mmol), and DIPEA (1.1 g, 8.4 mmol). The reaction was stirred at 0° C. for 2 h and then at room temperature overnight. The mixture was concentrated in vacuo and the residue chromatographed twice on silica gel, eluting first with CHCl$_3$:EtOH (15:1) and second with EtOAc:EtOH (20:1) to afford the sub-title compound (1.3 g, 56%) as a crushable white foam.

R$_f$=0.65 (15:1 CHCl$_3$:EtOH)

$^1$H NMR (300 MHz, CD$_3$OD, complex mixture of rotamers) δ 7.80-7.84 (m, 2H), 7.40-7.46 (m, 2H), 6.95-7.16 (m, 3H), 6.92 and 6.88 (t, J$_{H-F}$=73 Hz, 1H), 5.28 and 5.08 (s, 1H), 5.18-5.22 and 4.70-4.78 (m, 1H), 4.50-4.75 (m, 1H), 4.30-4.49 (m, 2H), 4.21-4.26 (m, 3H), 3.97-4.08 (m, 1H), 3.35-3.72 (m, 6H), 3.30 (s, 3H), 2.10-2.75 (m, 2H), 1.05-1.11 (m, 2H), 0.08 (s, 9H).

(xi) Ph(3-F)(5-OCHF$_2$)—(R)CH(OH)C(O)-Aze-Pab (Teoc)

A mixture of Ph(3-F)(5-OCHF$_2$)—(R)CH(OMEM)C(O)-Aze-Pab(Teoc) (590 mg, 0.87 mmol; see step (x) above) and carbon tetrabromide (287 mg, 0.87 mmol) in 2-propanol (20 mL) was refluxed for 1.5 h. The mixture was concentrated in vacuo then, partitioned with H$_2$O (50 mL) and EtOAc (3× 50 mL). The aqueous layer was extracted with additional EtOAc (2× 10 mL). The combined organic extracts were washed with brine (30 mL) then dried (Na$_2$SO$_4$), filtered and concentrated in vacuo. Flash chromatography on silica gel eluting with CHCl$_3$:EtOH (15:1) afforded the sub-title compound (60 mg, 12%) as a crushable white foam.

R$_f$=0.46 (15:1 CHCl$_3$:EtOH)

$^1$H NMR (300 MHz, CD$_3$OD, complex mixture of rotamers) δ 7.74 (d, J=8 Hz, 2H), 7.35-7.37 (m, 2H), 6.97-7.07 (m, 2H), 6.80-6.84 (m, 1H), 6.82 and 6.80 (t, J$_{H-F}$=73 Hz, 1H), 5.10 and 5.06 (s, 1H), 4.68-4.70 (m, 1H), 3.97-4.60 (m, 6H), 2.10-2.75 (m, 2H), 1.05-1.11 (m, 2H), 0.08 (s, 9H).

APCI-MS: (M+1)=595 m/z

(xii) Ph(3-F)(5-OCHF$_2$)—(R)CH(OH)C(O)-Aze-Pab×TFA

Ph(3-F)(5-OCHF$_2$)—(R)CH(OH)C(O)-Aze-Pab(Teoc) (0.053 g, 0.089 mmol; see step (xi) above), was dissolved in 3 mL of TFA and allowed to react for 80 min while cooled on an ice bath. TFA was evaporated and the residue was freeze dried from water/acetonitrile to yield 0.042 g (80%) of the title compound as its TFA salt.

$^1$H-NMR (300 MHz; CD$_3$OD) rotamers: δ 7.7-7.6 (m, 2H), 7.5-7.4 (m, 2H), 7.1-6.6 (m, 4H), 5.2-5.0 (m, 1H plus minor rotamer of 1H), ca 4.8 (major rotamer of previous signal obscured by the CD$_3$OH signal), 4.6-4.3 (m, 2H), 4.26 (m, 1H, major rotamer), 4.10 (m, 1H, major rotamer), 3.96 (m, 1H, minor rotamer), 3.89 (m, 1H, minor rotamer), 2.60 (m, 1H, minor rotamer), 2.44 (m, 1H, major rotamer), 2.19 (m, 1H, major rotamer), 2.05 (m, 1H, minor rotamer).

$^{13}$C-NMR (100 MHz; CD$_3$OD): (carbonyl and/or amidine carbons) δ 172.8, 172.0, 167.0.

ESI-MS+: (M+1)=451 (m/z)

EXAMPLE 26

Ph(3-F)(5-OCHF$_2$)—(R)CH(OH)C(O)-Aze-Pab(OMe)

(i) Ph(3-F)(5-OCHF$_2$)—(R)CH(OMEM)C(O)-Aze-Pab(OMe)

To a solution of Ph(3-F)(5-OCHF$_2$)—(R)CH(OMEM)C(O)OH (1.0 g, 3.1 mmol; see Example 25(ix) above) in DMF (30 mL) under nitrogen at 0° C. was added HAze-Pab(OMe).2HCl (1.4 g, 4.1 mmol), PyBOP (1.8 g, 3.4 mmol), and DIPEA (1.0 g, 7.8 mmol). The reaction was stirred at 0° C. for 2 h and then at room temperature overnight. The mixture was concentrated in vacuo and the residue chromatographed two times on silica gel, eluting first with CHCl$_3$:EtOH (15:1) and second with EtOAc to afford the sub-title compound (1.5 g, 79%) as a crushable white foam.

R$_f$=0.24 (EtOAc)

$^1$H NMR (300 MHz, CD$_3$OD, complex mixture of rotamers) δ 7.58-7.62 (m, 2H), 7.32-7.38 (m, 2H), 7.03-7.16 (m, 3H), 6.92 and 6.88 (d, J$_{H-F}$=73 Hz, 1H), 5.27 and 5.08 (s, 1H), 5.22-5.15 and 4.75-4.80 (m, 1H), 4.38-4.65 (m, 5H), 3.92-4.27 (m, 1H), 3.82 (s, 3H), 3.43-3.68 (m, 4H), 3.29 (s, 3H), 2.28-2.85 (m, 2H).

(ii) Ph(3-F)(5-OCHF$_2$)—(R)CH(OH)C(O)-Aze-Pab(OMe)

A mixture of Ph(3-F)(5-OCHF$_2$)—(R)CH(OMEM)C(O)-Aze-Pab(OMe) (828 mg, 2.33 mmol; see step (i) above) and carbon tetrabromide (525 mg, 2.33 mmol) in 2-propanol (20 mL) was refluxed for 8 h and then stirred at room temperature overnight. The mixture was concentrated in vacuo and the residue partitioned with H$_2$O (70 mL) and EtOAc (50 mL). The aqueous layer was extracted with EtOAc (2× 25 mL). The combined organic extracts were washed with brine (35 mL) then, dried (Na$_2$SO$_4$), filtered and concentrated in vacuo. Flash chromatography on silica gel eluting with CHCl$_3$:EtOH (15:1) afforded the title compound (520 mg, 74%) as a crushable white foam.

Mp: 73-81° C.

R$_f$=0.43 (15:1 CHCl$_3$:EtOH)

$^1$H NMR (300 MHz, CD$_3$OD, complex mixture of rotamers) δ 7.59 (d, J=8 Hz, 2H), 7.32-7.37 (m, 2H), 7.05-7.14 (m, 2H), 6.87-6.92 (m, 1H), 6.90 and 6.86 (t, J$_{H-F}$=73 Hz, 1H), 5.13-5.18 and 4.75-4.85 (m, 2H), 4.15-4.45 (m, 4H), 3.81 (s, 3H), 2.10-2.75 (m, 2H).

$^{13}$C-NMR (100 MHz; CD$_3$OD): (carbonyl and/or amidine carbons) δ 172.0, 171.4, 153.9.

APCI-MS: (M+1)=481 m/z

EXAMPLE 27

Ph(3-Br)(5-OCH$_2$F)—(R)CH(OH)C(O)-Aze-Pab×TFA

(i) 1,3-Dibromo-5-benzyloxybenzene

Sodium hydride (9.9 g, 0.414 mol, 95% dry) was added in portions to a stirred solution of benzyl alcohol (41.0 g, 0.394 mol) in THF (1.0 L) at room temperature under a nitrogen atmosphere and stirred for 1 h. To this solution was added dropwise 1,3-dibromo-5-fluorobenzene (100.0 g, 0.394 mol). After stirring overnight, the mixture was partitioned with H$_2$O (600 mL) and EtOAc (4× 600 mL). The combined organic extracts were dried (Na$_2$SO$_4$), filtered and concentrated in vacuo. Flash chromatography on silica gel eluting with hexanes afforded the sub-title compound (101.3 g, 75%) as a yellow oil.

$^1$H NMR (300 MHz, CDCl$_3$) δ 7.30-7.48 (m, 5H), 7.18 (s, 1H), 7.06 (s, 2H), 4.99 (s, 2H).

(ii) 3,5-Dibromophenol

Aluminium chloride (11.7 g, 87.6 mmol) was added in portions to a solution of 1,3-dibromo-5-benzyloxybenzene (10.0 g, 29.2 mmol; see step (i) above) and N,N-dimethylaniline (35.4 g, 292 mmol) in CH$_2$Cl$_2$ (100 mL) at room temperature under a nitrogen atmosphere. After 30 min, the mixture was partitioned with 1N HCl (300 mL) and EtOAc (5× 150 mL). The combined organic extracts were washed with saturated NaHCO$_3$ (150 mL) and brine (150 mL) then, dried (Na$_2$SO$_4$), filtered and concentrated in vacuo. Flash chromatography on silica gel eluting with Hex:EtOAc (9:1) afforded the sub-title compound (6.1 g, 82%) as a white solid.

$^1$H NMR (300 MHz, CDCl$_3$) δ 7.21 (s, 1H), 6.97 (s, 2H), 5.88 (bs, 1H).

(iii) 1,3-Dibromo-5-monofluoromethoxybenzene

To a tared, sealed 350 mL round-bottomed pressure flask containing a suspension of 3,5-dibromophenol (10.0 g, 39.7 mmol; see step (ii) above) and Cs$_2$CO$_3$ (20.7 g, 63.5 mmol) in DMF (150 mL) at −78° C. was added chlorofluoromethane via bubbling for 5 min through the septum. The septum was replaced with a Teflon stopper and the flask was then sealed and allowed to warm to room temperature where the flask was weighed and determined to contain 9.0 g (131 mmol) of chlorofluoromethane. The solution was heated in an oil bath set at 70° C. overnight. The flask was cooled to room temperature, the pressure cautiously released and the contents diluted with water (100 mL). The aqueous layer was extracted with Et$_2$O (3× 200 mL) then, the combined organics were dried (Na$_2$SO$_4$), filtered and concentrated in vacuo. Flash chromatography on silica gel eluting with hexanes afforded the sub-title compound (7.9 g, 71%) as a white solid.

$^1$H NMR (300 MHz, CDCl$_3$) δ 7.40 (s, 1H), 7.18 (s, 2H), 5.67 (d, J$_{H-F}$=53 Hz, 2H).

(iv) 1-Bromo-3-monofluoromethoxy-5-vinylbenzene

Tri(butyl)vinyltin (10.0 g, 31.4 mmol) was added dropwise to a solution of 1,3-dibromo-5-monofluoromethoxybenzene (8.5 g, 29.9 mmol; see step (iii) above), tetrakis(triphenylphosphine)palladium(0) (690 mg, 0.599 mmol), and 2,6-di-tert-butyl-4-methylphenol (spatula tip) in toluene (100 mL) under nitrogen. The mixture was stirred at 70° C. for 8 h. The mixture was cooled to 0° C. and 1N NaOH (70 mL) was added. After 1 h, the mixture was extracted with $CH_2Cl_2$ (3×300 mL) then, the combined organics were dried ($Na_2SO_4$), filtered and concentrated in vacuo. Flash chromatography on silica gel eluting with hexanes afforded the sub-title compound (4.3 g, 57%) as a colourless oil.

$^1$H NMR (300 MHz, $CDCl_3$) δ 7.30 (s, 1H), 7.16 (s, 1H), 7.01 (s, 1H), 6.60 (dd, J=6 Hz, J=11 Hz, 1H), 5.74 (d, J=16 Hz, 1H), 5.67 (d, $J_{H-F}$=53 Hz, 2H), 5.32 (d, J=8 Hz, 1H).

(v) Ph(3-Br)(5-OCH$_2$F)—(R)CH(OH)CH$_2$OH

2-Methyl-2-propanol (100 mL), $H_2O$ (100 mL), and AD-mix-β (27.5 g) were combined together and cooled to 0° C. 1-Bromo-3-monofluoromethoxy-5-vinylbenzene (4.3 g, 17.3 mmol; see step (iv) above) was added at once, and the heterogeneous slurry was vigorously stirred at 0° C. until TLC revealed the absence of the starting material. The reaction was quenched at 0° C. by addition of saturated sodium sulfite (200 mL) and then warmed to room temperature and stirred for 60 min. The reaction mixture was extracted with EtOAc (3× 150 mL). The combined organic extracts were dried ($Na_2SO_4$), filtered and concentrated in vacuo to afford the sub-title compound (4.9 g, 100%) as a colourless oil that was used without further purification.

$^1$H NMR (300 MHz, $CD_3OD$) δ 7.30 (s, 1H), 7.15 (s, 1H), 7.11 (s, 1H), 5.70 (d, $J_{H-F}$=53 Hz, 2H), 4.62-4.70 (m, 1H), 3.52-3.70 (m, 2H).

HPLC Analysis: 92.1%, 96.9% ee, ChiralPak AD Column (95:5 Hex:EtOH mobile phase).

(vi) Ph(3-Br)(5-OCH$_2$F)—(R)CH(OMEM) CH$_2$OTBS

To a solution of Ph(3-Br)(5-OCH$_2$F)—(R)CH(OH) CH$_2$OH (4.9 g, 18.6 mmol; see step (v) above), 4-(dimethylamino)pyridine (453 mg, 3.71 mmol), and DIPEA (8.9 g, 93.0 mmol) in anhydrous $CH_2Cl_2$ (200 mL) was added dropwise a 1.0 M solution of tert-butyldimethylsilyl chloride in $CH_2Cl_2$ (22.3 mL, 22.3 mmol). The reaction mixture was stirred 10 h at room temperature. To the mixture was added DIPEA (8.9 g, 93.0 mmol) and 2-methoxyethoxymethyl chloride (13.9 g, 111 mmol) dropwise. After 16 h, additional 2-methoxyethoxymethyl chloride (2.2 g) was added and the reaction stirred overnight. The mixture was diluted with $H_2O$ (100 mL), and the layers were separated. The aqueous layer was extracted with $CH_2Cl_2$ (3× 200 mL) then, the combined organic layers were dried ($Na_2SO_4$), filtered and concentrated in vacuo. Flash chromatography on silica gel eluting with Hex:EtOAc (5:1) afforded the sub-title compound (4.8 g, 55%) as a colourless oil.

$^1$H NMR (300 MHz, $CDCl_3$) δ 7.29 (s, 1H), 7.22 (s, 1H), 7.05 (s, 1H), 5.74 (d, $J_{H-F}$=53 Hz, 2H), 4.84 (d, J=7 Hz, 1H), 4.70-4.74 (m, 2H), 3.50-3.91 (m, 6H), 3.42 (s, 3H), 0.90 (s, 9H), 0.05 (s, 3H), 0.01 (s, 3H).

(vii) Ph(3-Br)(5-OCH$_2$F)—(R)CH(OMEM)CH$_2$OH

To a solution of Ph(3-Br)(5-OCH$_2$F)—(R)CH(OMEM) CH$_2$OTBS (4.7 g, 10.1 mmol; see step (vi) above) in THF (100 mL) was added a 1.0 M solution of tetrabutylammonium fluoride in THF (13.1 mL, 13.1 mmol) at room temperature and the mixture was stirred 1 h. The mixture was partitioned with $H_2O$ (100 mL) and EtOAc (3×—100 mL) then, the combined organics were dried ($Na_2SO_4$), filtered and concentrated in vacuo to afford the sub-title compound (3.3 g, 92%) as a colourless oil that was used without further purification.

$^1$H NMR (300 MHz, $CD_3OD$) δ 7.22 (s, 1H), 7.14 (s, 1H), 7.03 (s, 1H), 5.71 (d, $J_{H-F}$=53 Hz, 2H), 4.80-4.82 (m, 1H), 4.58-4.66 (m, 2H), 3.71-3.77 (m, 1H), 3.39-3.65 (m, 5H), 3.27 (s, 3H).

(viii) Ph(3-Br)(5-OCH$_2$F)—(R)CH(OMEM)C(O) OH

A solution of Ph(3-Br)(5-OCH$_2$F)—(R)CH(OMEM) CH$_2$OH (2.1 g, 6.0 mmol; see step (vii) above) in acetone (40 mL) was added to an aqueous 5% NaHCO$_3$ solution (15 mL). This magnetically stirred heterogeneous mixture was cooled to 0° C. and potassium bromide (70 mg, 0.60 mmol) and 2,2,6,6-tetramethyl-1-piperidinyloxy, free radical (976 mg, 5.8 mmol) were added. Sodium hypochlorite (5.25%, 15 mL) was then added dropwise over a period of 10 min while the mixture was vigorously stirred and maintained at 0° C. After 1 h, additional sodium hypochlorite (10 mL) and NaHCO$_3$ solution (20 mL) were added and stirring was continued at 0° C. for an additional 4 h. The acetone was removed on a rotary evaporator. The aqueous layer was diluted with 10% NaHCO$_3$ solution (30 mL) and was washed with Et$_2$O (3× 20 mL). The aqueous layer was acidified to pH 3.5 with 10% citric acid and extracted with EtOAc (3× 40 mL). The combined EtOAc extracts were washed with $H_2O$ (3× 50 mL) and brine (50 mL) then, dried ($Na_2SO_4$), filtered and concentrated in vacuo to afford the sub-title compound (1.7 g, 78%) as a colourless oil which was used without further purification.

$^1$H NMR (300 MHz, $CD_3OD$) δ 7.38 (s, 1H), 7.25 (s, 1H), 7.18 (s, 1H), 5.76 (d, $J_{H-F}$=53 Hz, 2H), 5.21 (s, 1H), 4.83 (d, J=7 Hz, 1H), 4.75 (d, J=7 Hz, 1H), 3.62-3.78 (m, 2H), 3.48-3.52 (m, 2H), 3.32 (s, 3H).

(ix) Ph(3-Br)(5-OCH$_2$F)—(R)CH(OMEM)C(O)-Aze-Pab(Teoc)

To a solution of Ph(3-Br)(5-OCH$_2$F)—(R)CH(OMEM)C (O)OH (1.0 g, 2.72 mmol; see step (viii) above) in DMF (20 mL) under nitrogen at 0° C. was added HAze-Pab(Teoc).HCl (1.6 g, 3.5 mmol), PyBOP (1.6 g, 3.0 mmol), and DIPEA (880 mg, 6.81 mmol). The reaction was stirred at 0° C. for 2 h and then at room temperature overnight. The mixture was concentrated in vacuo and the residue chromatographed twice on silica gel, eluting first with CHCl$_3$:EtOH (15:1) and second with EtOAc:EtOH (20:1) to afford the sub-title compound (1.2 g, 62%) as a crushable white foam.

$^1$H NMR (300 MHz, $CD_3OD$, complex mixture of rotamers) δ 7.80-7.84 (m, 2H), 7.40-7.46 (m, 2H), 7.13-7.32 (m, 3H), 5.84-5.87 (m, 1H), 5.67-5.69 (m, 1H), 5.25 and 5.07 (s, 1H), 5.18-5.23 and 4.80-4.88 (m, 1H), 3.97-4.79 (m, 8H), 3.60-3.71 (m, 2H), 3.40-3.53 (m, 2H), 3.32 (s, 3H), 2.10-2.75 (m, 2H), 1.05-1.11 (m, 2H), 0.08 (s, 9H).

(x) Ph(3-Br)(5-OCH$_2$F)—(R)CH(OH)C(O)-Aze-Pab (Teoc)

A mixture of Ph(3-Br)(5-OCH$_2$F)—(R)CH(OMEM)C (O)-Aze-Pab(Teoc) (347 mg, 0.478 mmol; see step (ix) above) and carbon tetrabromide (159 mg, 0.478 mmol) in 2-propanol (10 mL) was refluxed for 1.5 h. The mixture was concentrated in vacuo then partitioned with $H_2O$ (20 mL) and EtOAc (3× 30 mL). The combined organics were dried ($Na_2SO_4$), filtered and concentrated in vacuo. Flash chromatography on silica gel eluting with CHCl₃:EtOH (15:1) afforded the sub-title compound (59 mg, 19%) as a crushable white foam.

Mp: 81-87° C.

$R_f$=0.58 (9:1 CHCl₃:EtOH)

¹H NMR (300 MHz, CD₃OD, complex mixture of rotamers) δ 7.84 (d, J=8 Hz, 2H), 7.40-7.48 (m, 2H) 7.18-7.30 (m, 3H), 5.80 (d, $J_{H-F}$=53 Hz, 2H), 5.21 and 5.15 (s, 1H), 5.18-5.24 and 4.80-4.88 (m, 1H), 3.98-4.54 (m, 6H), 2.10-2.70 (m, 2H), 1.05-1.11 (m, 2H), 0.08 (s, 9H).

APCI-MS: (M+1)=637 m/z (xi) Ph(3-Br)(5-OCH₂F)—(R)CH(OH)C(O)-Aze-Pab×TFA

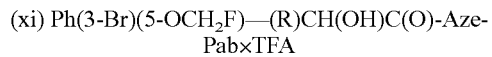

Ph(3-Br)(5-OCH₂F)—(R)CH(OH)C(O)-Aze-Pab(Teoc) (0.073 g, 0.11 mmol; see step (x) above), was dissolved in 5 mL of TFA and allowed to react for 90 min while being cooled on an ice bath. TFA was evaporated and the residue purified by prep RPLC with CH₃CN:0.1M NH₄OAc (30:70). The pertinent fractions were evaporated and freeze dried from water/acetonitrile to yield 49 mg (77%) of the title compound as its acetate salt.

¹H-NMR (300 MHz; CD₃OD) rotamers: δ 7.8-7.7 (m, 2H), 7.54 (m, 2H), 7.37 (s, 1H, major rotamer), 7.33 (s, 1H, minor rotamer), 7.25-7.1 (m, 2H), 5.75 (d, 2H), 5.22 (m, 1H, minor rotamer), 5.18 (s, 1H, major rotamer), 5.11 (s, 1H, minor rotamer), 4.80 (m, 1H, major rotamer), 4.6-4.4 (m, 2H), 4.37 (m, 1H, major rotamer), 4.16 (m, 1H, major rotamer), 4.1-3.9 (m, 2H, two signals from minor rotamer), 2.70 (m, 1H, minor rotamer), 2.52 (m, 1H, major rotamer), 2.30 (m, 1H, major rotamer), 2.15 (m, 1H, minor rotamer), 1.89 (s, 3H).

ESI-MS+: (M+1)=493/495 (m/z)

EXAMPLE 28

Ph(3-Br)(5-OCHF₂)—(R)CH(OH)C(O)-Aze-Pab×TFA (i) 1,3-Dibromo-5-difluoromethoxybenzene To a tared, sealed 350 mL round-bottomed pressure flask containing a solution of 3,5-dibromophenol (10.0 g, 39.7 mmol; see Example 27(ii) above) in 2-propanol (100 mL) and 30% KOH (80 mL) at −78° C. was added chlorodifluoromethane via bubbling for 15 min through the septum. The septum was replaced with a Teflon stopper and the flask was then sealed and allowed to warm to room temperature where the flask was weighed and determined to contain 12.0 g (138 mmol) of chlorodifluoromethane. The solution was refluxed overnight in an oil bath set at 80° C. The flask was cooled to room temperature, the pressure cautiously released and the contents diluted with H₂O (200 mL). The aqueous layer was extracted with CHCl₃ (2× 150 mL), then the combined organics were dried (Na₂SO₄), filtered and concentrated in vacuo. The residue was purified by Kugelrohr distillation at 80° C. at 0.2 mm Hg to afford the sub-title compound (9.6 g, 80%) as clear liquid.

¹H NMR (300 MHz, CDCl₃) δ 7.55 (s, 1H), 7.26 (s, 2H), 6.52 (t, $J_{H-F}$=68 Hz, 1H).

(ii) I-Bromo-3-difluoromethoxy-5-vinylbenzene

Tri(butyl)vinyltin (10.5 g, 33.1 mmol) was added dropwise to a solution of 1,3-dibromo-5-difluoromethoxybenzene (9.1 g, 30.1 mmol; see step (i) above), tetrakis(triphenylphosphine)palladium(0) (700 mg, 0.60 mmol), and 2,6-di-tert-butyl-4-methylphenol (spatula tip) in toluene (125 mL) under nitrogen. The mixture was stirred at 50° C. overnight. The mixture was cooled to 0° C. and 1N NaOH (70 mL) was added. After 1 h, the mixture was extracted with CH₂Cl₂ (3× 300 mL) then, the combined organics were dried (Na₂SO₄), filtered and concentrated in vacuo. Flash chromatography on silica gel eluting with hexanes afforded the sub-title compound (5.1 g, 68%) as a colourless oil.

¹H NMR (300 MHz, CDCl₃) δ 7.53 (s, 1H), 7.18 (s, 1H), 7.08 (s, 1H), 6.60 (dd, J=6 Hz, J=11 Hz, 1H), 6.57 (t, $J_{H-F}$=68 Hz, 1H), 5.77 (d, J=11 Hz, 1H), 5.36 (d, J=8 Hz, 1H).

(iii) Ph(3-Br)(5-OCHF₂)—(R)CH(OH)CH₂OH

2-Methyl-2-propanol (150 mL), H₂O (150 mL), and AD-mix-β (27.8 g) were combined together and cooled to 0° C. I-Bromo-3-difluoromethoxy-5-vinylbenzene (4.6 g, 18.6 mmol; see step (ii) above) was added at once, and the heterogeneous slurry was vigorously stirred at 0° C. until TLC indicated the absence of the starting material, then the solution was warmed to room temperature and stirred overnight. The reaction was quenched at 0° C. by addition of saturated sodium sulfite (300 mL) and then warmed to room temperature and stirred for 60 min. The reaction mixture was extracted with EtOAc (3× 200 mL). The combined organic extracts were dried (Na₂SO₄), filtered and concentrated in vacuo to afford the sub-title compound (5.0 g, 95%) as a colourless oil that was used without further purification.

¹H NMR (300 MHz, CD₃OD) δ 7.43 (s, 1H), 7.23 (s, 1H), 7.16 (s, 1H), 6.86 (t, $J_{H-F}$=75 Hz, 1H), 4.64-4.67 (m, 1H), 3.54-3.59 (m, 2H).

HPLC Analysis: 88.6%, 96.3% ee, ChiralPak AD Column (95:5 Hex:EtOH mobile phase).

(iv) Ph(3-Br)(5-OCHF₂)—(R)CH(OMEM)CH₂OTBS

To a solution of Ph(3-Br)(5-OCHF₂)—(R)CH(OH)CH₂OH (4.9 g, 17.3 mmol; see step (iii) above), 4-(dimethylamino)pyridine (420 mg, 3.5 mmol), and DIPEA (11.2 g, 86.3 mmol) in anhydrous CH₂Cl₂ (250 mL) was added dropwise a 1.0 M solution of tert-butyldimethylsilyl chloride in CH₂Cl₂ (20.7 mL, 20.7 mmol). The reaction mixture was stirred overnight at room temperature. To the mixture was added DIPEA (11.2 g, 86.3 mmol) and 2-methoxyethoxymethyl chloride (12.9 g, 104 mmol) dropwise. After 3 d, additional 2-methoxyethoxymethyl chloride (3.3 g) was added and the reaction stirred overnight. The mixture was diluted with water (250 mL), and the layers were separated. The aqueous layer was extracted with CH₂Cl₂ (2× 250 mL), then the combined organics were dried (Na₂SO₄), filtered and concentrated in vacuo. Flash chromatography on silica gel eluting with Hex:EtOAc (4:1) afforded the sub-title compound (4.3 g, 51%) as a colourless oil.

¹H NMR (300 MHz, CDCl₃) δ 7.40 (s, 1H), 7.25 (s, 1H), 7.08 (s, 1H), 6.58 (t, $J_{H-F}$=75 Hz, 1H), 4.84 (d, J=7 Hz, 1H), 4.70-4.74 (m, 2H), 3.50-3.91 (m, 6H), 3.42 (s, 3H), 0.90 (s, 9H), 0.12 (s, 3H), 0.05 (s, 3H).

(v) Ph(3-Br)(5-OCHF₂)—(R)CH(OMEM)CH₂OH

To a solution of Ph(3-Br)(5-OCHF₂)—(R)CH(OMEM)CH₂OTBS (3.3 g, 6.9 mmol; see step (iv) above) in THF (60 mL) was added a 1.0 M solution of tetrabutylammonium fluoride in THF (9.0 mL, 9.0 mmol) at room temperature. The reaction was stirred for 45 min, then the mixture was partitioned with water (150 mL) and EtOAc (2×120 mL). The combined organics were dried ($Na_2SO_4$), filtered and concentrated in vacuo to afford the sub-title compound (2.5 g, 98%) as a yellow oil that was used without further purification.

$^1$H NMR (300 MHz, $CD_3OD$)) δ 7.35 (s, 1H), 7.21 (s, 1H), 7.08 (s, 1H), 6.83 (t, $J_{H-F}$=73 Hz, 1H), 4.73 (d, J=7 Hz, 1H), 4.59-4.68 (m, 2H), 3.40-380 (m, 6H), 3.26 (s, 3H).

(vi) Ph(3-Br)(5-OCHF$_2$)—(R)CH(OMEM)C(O)OH

A solution of Ph(3-Br)(5-OCHF$_2$)—(R)CH(OMEM)$CH_2OH$ (3.0 g, 8.1 mmol; see step (v) above) in acetone (60 mL) was added to an aqueous 5% $NaHCO_3$ solution (25 mL). This magnetically stirred heterogeneous mixture was cooled to 0° C. then potassium bromide (100 mg, 0.81 mmol) and 2,2,6,6-tetramethyl-1-piperidinyloxy, free radical (1.3 g, 8.5 mmol) were added. Sodium hypochlorite (5.25%, 19 mL) was then added dropwise over a period of 10 min while the mixture was vigorously stirred and maintained at 0° C. After 1 h, additional sodium hypochlorite (17 mL) and $NaHCO_3$ solution (34 mL) were added and stirring was continued at 0° C. for an additional 4 h. The acetone was removed on a rotary evaporator. The aqueous layer was diluted with 10% $NaHCO_3$ solution (30 mL) and was washed with $Et_2O$ (3× 20 mL). The aqueous layer was acidified to pH 3.5 with 10% citric acid and extracted with EtOAc (3× 40 mL). The combined EtOAc layers were washed with $H_2O$ (3× 50 mL) and brine (50 mL), and then dried ($Na_2SO_4$), filtered and concentrated in vacuo to afford the sub-title compound (2.1 g, 66%) as a colourless oil which was used without further purification.

$^1$H NMR (300 MHz, $CD_3OD$) δ 7.51 (s, 1H), 7.32 (s, 1H), 7.24 (s, 1H), 6.88 (t, $J_{H-F}$=73 Hz, 1H), 5.21 (s, 1H), 4.84 (d, J=7 Hz, 1H), 4.76 (d, J=7 Hz, 1H), 3.62-3.80 (m, 2H), 3.48-3.52 (m, 2H), 3.32 (s, 3H).

(vii) Ph(3-Br)(5-OCHF$_2$)—(R)CH(OMEM)C(O)-Aze-Pab(Teoc)

To a solution of Ph(3-Br)(5-OCHF$_2$)—(R)CH(OMEM)C(O)OH (1.0 g, 2.62 mmol; see step (vi) above) in DMF (50 mL) under nitrogen at 0° C. was added HAze-Pab(Teoc).HCl (1.5 g, 3.38 mmol), PyBOP (1.5 g, 2.9 mmol), and DIPEA (840 mg, 6.50 mmol). The reaction was stirred at 0° C. for 2 h and then at room temperature overnight. The mixture was concentrated in vacuo and the residue chromatographed on silica gel eluting with $CHCl_3$:EtOH (15:1) to afford the sub-title compound (1.1 g, 59%) as a crushable white foam.

$^1$H NMR (300 MHz, $CD_3OD$, complex mixture of rotamers) δ 7.79-7.83 (m, 2H), 7.26-7.52 (m, 5H), 6.94 and 6.91 (t, $J_{H-F}$=73 Hz, 1H), 5.27 and 5.07 (s, 1H), 5.20-5.23 and 4.80-4.88 (m, 1H), 4.01-4.79 (m, 8H), 3.60-3.71 (m, 2H), 3.40-3.53 (m, 2H), 3.32 (s, 3H), 2.10-2.75 (m, 2H), 1.05-1.11 (m, 2H), 0.08 (s, 9H).

(viii) Ph(3-Br)(5-OCHF$_2$)—(R)CH(OH)C(O)-Aze-Pab(Teoc)

A mixture of Ph(3-Br)(5-OCHF$_2$)—(R)CH(OMEM)C(O)-Aze-Pab(Teoc) (369 mg, 0.496 mmol; see step (vii) above) and carbon tetrabromide (165 mg, 0.496 mmol) in 2-propanol (10 mL) was refluxed for 12 h. The mixture was concentrated in vacuo, then partitioned with $H_2O$ (15 mL) and EtOAc (5× 20 mL). The combined organics were dried ($Na_2SO_4$), filtered and concentrated in vacuo. Flash chromatography on silica gel eluting with $CHCl_3$:EtOH (15:1) afforded the sub-title compound (134 mg, 41%) as a crushable white foam.

Mp: 92-98° C.
$R_f$=0.37 (9:1 $CHCl_3$:EtOH)

$^1$H NMR (300 MHz, $CD_3OD$, complex mixture of rotamers) δ 7.80-7.86 (m, 2H), 7.40-7.48 (m, 2H) 7.10-7.33 (m, 3H), 6.92 and 6.88 (t, $J_{H-F}$=73. Hz, 1H), 5.18 and 5.11 (s, 1H), 5.18-5.24 and 4.76-4.80 (m, 1H), 3.98-4.54 (m, 6H), 2.10-2.70 (m, 2H), 1.05-1.11 (m, 2H), 0.08 (s, 9H).

APCI-MS: (M+1)=655 m/z (ix) Ph(3-Br)(5-OCHF$_2$)—(R)CH(OH)C(O)-Aze-Pab×TFA

Ph(3-Br)(5-OCHF$_2$)—(R)CH(OH)C(O)-Aze-Pab(Teoc) (0.081 g, 0.124 mmol; see step (viii) above), was dissolved in 5 mL of TFA and allowed to react for 80 min while being cooled on an ice bath. TFA was evaporated and the residue purified by prep RPLC with $CH_3CN$:0.1M $NH_4OAc$ (30:70). The pertinent fractions were evaporated and freeze dried from water/acetonitrile to yield 59 mg (83%) of the title compound as its acetate salt.

$^1$H-NMR (300 MHz; $CD_3OD$) rotamers: δ 7.8-7.7 (m, 2H), 7.6-7.4 (m, 3H), 7.3-7.2 (m, 2H), 6.89 (t, 1H, major rotamer), 6.87 (t, 1H, minor rotamer), 5.23 (m, 1H, minor rotamer), 5.21 (s, 1H, major rotamer), 5.13 (s, 1H, minor rotamer), 4.80 (m, 1H, major rotamer), 4.6-4.4 (m, 2H), 4.38 (m, 1H, major rotamer), 4.20 (m, 1H, major rotamer), 4.1-3.9 (m, 2H, two signals from minor rotamer), 2.70 (m, 1H, minor rotamer), 2.54 (m, 1H, major rotamer), 2.29 (m, 1H, major rotamer), 2.15 (m, 1H, minor rotamer), 1.89 (s, 3H).

$^{13}$C-NMR (75 MHz; $CD_3OD$): (carbonyl and/or amidine carbons) δ 172.0, 171.7, 167.0.

MS (m/z) 511/513 (M+1)$^+$

EXAMPLE 29

Ph(3-Br)(5-OCHF$_2$)—(R)CH(OH)C(O)-Aze-Pab(OMe)

(i) Ph(3-Br)(5-OCHF$_2$)—(R)CH(OMEM)C(O)-Aze-Pab(OMe)

To a solution of Ph(3-Br)(5-OCHF$_2$)—(R)CH(OMEM)C(O)OH (957 mg, 2.48 mmol; see Example 28(vi) above) in DMF (30 mL) under nitrogen at 0° C. was added HAze-Pab(OMe).2HCl (1.1 g, 3.2 mmol), PyBOP (1.4 g, 2.7 mmol), and DIPEA (804 mg, 6.2 mmol). The reaction was stirred at 0° C. for 2 h and then at room temperature overnight. The mixture was concentrated in vacuo and the residue chromatographed twice on silica gel, eluting first with $CHCl_3$:EtOH (9:1) and second with EtOAc:EtOH (15:1) to afford the sub-title compound (1.1 g, 72%) as a crushable white foam.

$^1$H NMR (300 MHz, $CD_3OD$, complex mixture of rotamers) δ 7.59-7.65 (m, 2H), 7.20-7.55 (m, 5H), 6.95 and 6.91 (t, $J_{H-F}$=73 Hz, 1H), 5.27 and 5.07 (s, 1H), 5.18-5.23 and 4.75-4.84 (m, 1H), 3.87-4.89 (m, 6H), 3.84 (s, 3H), 3.60-3.71 (m, 2H), 3.40-3.53 (m, 2H), 3.32 (s, 3H), 2.10-2.75 (m, 2H).

(ii) Ph(3-Br)(5-OCHF$_2$)—(R)CH(OH)C(O)-Aze-Pab(OMe)

A mixture of Ph(3-Br)(5-OCHF$_2$)—(R)CH(OMEM)C(O)-Aze-Pab(OMe) (1.1 g, 1.8 mmol; see step (i) above) and carbon tetrabromide (583 mg, 1.8 mmol) in 2-propanol (30 mL) was refluxed for 2.5 d. During this time, additional carbon tetrabromide (5 portions of 50 mg at intervals for an additional 0.90 mmol) was added to ensure completion of the reaction. The mixture was concentrated in vacuo, then partitioned with H₂O (50 mL) and EtOAc (5× 25 mL). The combined organics were dried (Na$_2$SO$_4$), filtered and concentrated in vacuo. Flash chromatography on silica gel eluting with CHCl$_3$:EtOH (15:1) afforded the title compound (460 mg, 50%) as a crushable white foam.

Mp: 71-75° C.

R$_f$=0.63 (9:1 CHCl$_3$:EtOH)

¹H NMR (300 MHz, CD$_3$OD, complex mixture of rotamers) δ 7.59 (d, J=8 Hz, 2H), 7.20-7.54 (m, 5H), 6.90 and 6.87 (t, J$_{H-F}$=73 Hz, 1H), 5.18 and 5.11 (s, 1H), 4.76-4.80 (m, 1H), 3.98-4.54 (m, 4H), 3.82 (s, 3H), 2.10-2.70 (m, 2H).

¹³C-NMR (100 MHz; CD$_3$OD): (carbonyl and/or amidine carbons, rotamers) δ 172.5, 172.1, 171.6, 154.1.

APCI-MS: (M+1)=542 m/z

EXAMPLE 30

Ph(3-Cl)(5-OCH$_2$CHF$_2$)—(R)CH(OH)C(O)-Aze-Pab(OH)

(i) Ph(3-Cl)(5-OCH$_2$CHF$_2$)—(R)CH(OH)C(O)-Aze-Pab(Z)

Boc-Aze-Pab(Z) (see international patent application WO 97/02284, 92 mg, 0.197 mmol) was dissolved in 10 mL of EtOAc saturated with HCl(g) and allowed to react for 10 min. The solvent was evaporated and the residue was mixed with Ph(3-Cl)(5-OCH$_2$CHF$_2$)—(R)CH(OH)C(O)OH (50 mg, 0.188 mmol; see Example 17(v) above), PyBOP (109 mg, 0.209 mmol) and finally diisopropylethyl amine (96 mg, 0.75 mmol) in 2 mL of DMF. The mixture was stirred for 2 h and then poured into 50 mL of water and extracted three times with EtOAc. The combined organic phase was washed with water, dried (Na$_2$SO$_4$) and evaporated. The crude product was flash chromatographed on silica gel with EtOAc:MeOH (9:1). Yield: 100 mg (87%).

¹H NMR (300 MHz, CD$_3$OD, mixture of rotamers) δ 7.85-7.75 (m, 2H), 7.45-7.25 (m, 7H), 7.11 (m, 1H, major rotamer), 7.08 (m, 1H, minor rotamer), 7.05-6.9 (m, 2H), 6.13 (bt, 1H), 5.25-5.05 (m, 3H), 4.77 (m, 1H, partially hidden by the CD$_3$OH signal), 4.5-3.9 (m, 7H), 2.64 (m, 1H, minor rotamer), 2.47 (m, 1H, major rotamer), 2.25 (m, 1H, major rotamer), 2.13 (m, 1H, minor rotamer)

(ii) Ph(3-Cl)(5-OCH$_2$CHF$_2$)—(R)CH(OH)C(O)-Aze-Pab(OH)

Hydroxylamine hydrochloride (65 mg, 0.94 mmol) and triethylamine (0.319 g, 3.16 mmol) were mixed in 8 mL of THF and sonicated for 1 h at 40° C. Ph(3-Cl)(5-OCH$_2$CHF$_2$)—(R)CH(OH)C(O)-Aze-Pab(Z) (96 mg, 0.156 mmol; see step (i) above) was added with 8 mL more of THF. The mixture was stirred at 40° C. for 4.5 days. The solvent was evaporated and the crude product was purified by preparative RPLC with CH$_3$CN:0.1M NH$_4$OAc (40:60). Yield: 30 mg (38%). Purity: 99%.

¹H NMR (300 MHz, CD$_3$OD, mixture of rotamers) δ 7.6-7.55 (m, 2H), 7.35-7.3 (m, 2H), 7.12 (m, 1H, major rotamer), 7.09 (m, 1H, minor rotamer), 7.05-6.9 (m, 2H), 6.15 (triplet of multiplets, 1H), 5.15 (m, 1H, minor rotamer), 5.13 (s, 1H, major rotamer), 5.08 (s, 1H, minor rotamer), 4.77 (m, 1H, major rotamer), 4.5-4.2 (m, 5H), 4.08 (m, 1H, major rotamer), 3.97 (m, 1H, minor rotamer), 2.66 (m, 1H, minor rotamer), 2.50 (m, 1H major rotamer), 2.27 (m, 1H, major rotamer), 2.14 (m, 1H, minor rotamer).

¹³C-NMR (100 MHz; CD$_3$OD): (carbonyl and/or amidine carbons, mixture of rotamers) δ 172.8, 172.2, 171.4, 159.1, 158.9, 154.2.

APCI-MS: (M+1) 497/499 m/z

EXAMPLE 31

Ph(3-Cl)(5-OCH$_2$CH$_2$F)—(R)CH(OH)C(O)-Aze-Pab(OH)

(i) Ph(3-Cl)(5-OCH$_2$CH$_2$F)—(R)CH(OH)C(O)-Aze-Pab(Z)

Boc-Aze-Pab(Z) (130 mg, 0.279 mmol) was dissolved in 15 mL of EtOAc saturated with HCl(g) and allowed to react for 10 min. The solvent was evaporated and the residue was mixed with Ph(3-Cl)(5-OCH$_2$CH$_2$F)—(R)CH(OH)—C(O)OH (63 mg, 0.188 mmol; see Example 21(v) above) in 3 mL of DMF, PyBOP (147 mg, 0.279 mmol) and finally diisopropylethyl amine (134 mg, 1.03 mmol). The mixture was stirred for 130 min and then poured into 75 mL of water and extracted three times with EtOAc. The combined organic phase was washed with water, dried (Na$_2$SO$_4$) and evaporated. The crude product was flash chromatographed on silica gel with EtOAc/MeOH=95/5. Yield: 119 mg (79%).

¹H NMR (400 MHz, CDCl$_3$) δ 8.06 (bt, 1H), 7.67 (d, 2H), 7.45-7.25 (m, 5H), 7.18 (d, 2H), 6.89 (m, 1H), 6.84 (m, 1H), 6.76 (m, 1H), 5.16 (s, 2H), 4.84 (s, 1H), 4.79 (m, 1H), 4.66 (doublet of multiplets, 2H), 4.4-4.3 (m, 2H), 4.10 (doublet of multiplets, 2H), 4.02 (m, 1H), 3.67 (m, 1H), 2.46 (m, 1H), 2.28 (m, 1H).

(ii) Ph(3-Cl)(5-OCH$_2$CH$_2$F)—(R)CH(OH)C(O)-Aze-Pab(OH)

Hydroxylamine hydrochloride (80 mg, 1.16 mmol) and triethylamine (0.392 g, 3.87 mmol) were mixed in 9 mL of THF and sonicated for 1 h at 40° C. Ph(3-Cl)(5-OCH$_2$CH$_2$F)—(R)CH(OH)C(O)-Aze-Pab(Z) (96 mg, 0.156 mmol; see step (i) above) was added with 9 mL more of THF. The mixture was stirred at 40° C. for 48 h and 3 days at room temperature. The solvent was evaporated and the crude product was purified by preparative RPLC with CH$_3$CN:0.1M NH$_4$OAc (30:70). Yield: 72 mg (78%). Purity: 100%.

¹H NMR (400 MHz, CD$_3$OD, mixture of rotamers) δ 7.6-7.55 (m, 2H), 7.35-7.25 (m, 4H), 7.07 (m, 1H, major rotamer), 7.04 (m, 1H, minor rotamer), 7.0-6.9 (M, 2 h), 5.12 (m, 1H, minor rotamer), 5.08 (s, 1H, minor rotamer), 5.04 (s, 1H), 4.78 (m, 1H, major rotamer), 4.68 (doublet of multiplets, 2H), 4.5-4.25 (m, 3H), 4.20 (doublet of multiplets, 2H) 4.06 (m, 1H, major rotamer), 3.97 (m, 1H, minor rotamer), 2.65 (m, 1H, minor rotamer), 2.48 (m, 1H major rotamer), 2.27 (m, 1H, major rotamer), 2.14 (m, 1H, minor rotamer)

¹³C-NMR (100 MHz; CD$_3$OD): (carbonyl and/or amidine carbons, mixture of rotamers) δ 172.3, 171.5, 159.8, 154.3

APCI-MS: (M+1)=479/481 m/z

EXAMPLE 32

Ph(3-Cl)(5-OCHF$_2$)—(R)CH(OH)—C(O)-Pro-Pab (i) Boc-Pro-Pab(Teoc)

Boc-Pro-Pab(Z) (see international patent application WO 97/02284, 15.0 g, 0.0321 mol) was dissolved in 150 mL of ethanol and 200 mg 10% Pd/C (50% moisture) was added. The mixture was stirred and hydrogenated at atmospheric pressure for 2 h, filtered through Hyflo and concentrated. The product was used without further purification. Of this product was taken 10 g (0.029 mol), which was dissolved in 300 mL of THF. Teoc-p-nitrophenyl carbonate (10 g, 0.035 mol) was added. A solution of potassium carbonate (5.2 g, 0.038 mol) in 50 mL of water was added over 3 min and the resulting solution was stirred for 3 days, concentrated and the remainder was extracted with EtOAc three times. The combined organic layer was washed with water, dried ($Na_2SO_4$) and evaporated. The crude product was flash chromatographed on silica gel using methylene chloride:acetone (4:1). Yield: 9.8 g (69%).

(ii) Ph(3-Cl)(5-OCHF$_2$)—(R)CH(OH)—C(O)-Pro-Pab(Teoc)

Boc-Pro-Pab(Teoc) (107 mg, 0.218 mmol; see step (i) above) was dissolved in 10 mL of EtOAc saturated with HCl(g) and allowed to react for 10 min. The solvent was evaporated and the residue was mixed with Ph(3-Cl)(5-OCHF$_2$)—(R)CH(OH)C(O)OH (50 mg, 0.198 mmol; see Example 1(viii) above) in 3 mL of DMF, PyBOP (115 mg, 0.218 mmol) and finally diisopropylethyl amine (104 mg, 0.80 mmol). The mixture was stirred for 2 h and then poured into 75 mL of water and extracted three times with EtOAc. The combined organic phase was washed with water, dried ($Na_2SO_4$) and evaporated. The crude product was flash chromatographed on silica gel with EtOAc:MeOH (95:5). Yield: 89 mg (72%).

$^1$H NMR (400 MHz, CDCl$_3$) δ 7.54 (bt, 1H), 7.47 (d, 2H), 7.12 (m, 1H), 7.08 (d, 2H), 7.02 (m, 1H), 6.95 (m, 1H), 6.50 (t, 1H), 5.21 (s, 1H), 4.42 (m, 1H), 4.35-4.15 (m, 3H), 3.59 (m, 1H), 2.94 (m, 1H), 2.1-1.7 (m, 4H), 1.06 (m, 2H), 0.04 (s, 9H).

(iii) Ph(3-Cl)(5-OCHF$_2$)—(R)CH(OH)—C(O)-Pro-Pab×TFA

Ph(3-Cl)(5-OCHF$_2$)—(R)CH(OH)—C(O)-Pro-Pab(Teoc) (85 mg, 0.136 mmol; see step (ii) above) was dissolved in 1 mL of methylene chloride and cooled on an ice bath. TFA (4 mL) was added and the reaction was stirred for 90 min. The TFA was evaporated and the residue was freeze-dried from water and acetonitrile. Yield: 79 mg (92%). Purity: 94%.

$^1$H NMR (400 MHz, CD$_3$OD, mixture of rotamers) δ 7.85-7.7 (m, 2H), 7.58 (d, 2H major rotamer), 7.47 (d, 2H, minor rotamer), 7.35 (m, 1H, major rotamer), 7.27 (m, 1H, minor rotamer), 7.2.7.1 (m, 2H), 6.88 (t, 1H), 5.38 (s, 1H, major rotamer), 5.22 (s, 1H, minor rotamer), 4.58 (d, 1H), 4.5-4.2 (m, 2H), 3.8-3.5 (m, 1H), 3.35 (m, 1H), 2.2-1.8 (m, 4H).

$^{13}$C-NMR (100 MHz; CD$_3$OD): (carbonyl and/or amidine carbons) δ 173.6, 171.1, 167.0.

APCI-MS: (M+1)=481/483 m/z

EXAMPLE 33

Ph(3-Cl)(5-OCHF$_2$)—(R)CH(OH)—C(O)-Pro-Pab(OMe)

(i) 4-Azidomethyl-N-methoxy-benzamidine

4-Azidomethylbenzonitrile (17.3 g, 0.109 mol; Nishiyama et al; *Chem. Lett.* (1982) 1477) was dissolved in 500 mL of toluene and 200 mL of absolute ethanol. The solution was cooled to −10° C. and HCl(g) was bubbled through until saturation. The mixture was kept in the refrigerator for 2 days when most of the solvents were evaporated. Diethyl ether was added and was decanted off. The product was re-dissolved in a solution of O-methylhydroxylamine (10.5 g, 0.125 mol) and triethyl amine (56 mL) in 200 mL of methanol. The mixture was allowed to stand for 3 days whence the methanol was evaporated with addition of EtOAc. The organic phase was washed with water, dilute HOAc and aqueous sodium bicarbonate, dried ($Na_2SO_4$) and diluted with more EtOAc to a total volume of 500 mL. A sample of 25 mL was evaporated to dryness. The remainder was 932 mg. Total yield: 18.6 g (83%).

(ii) 4-Aminomethyl-N-methoxy-benzamidine

To a solution of 4-azidomethyl-N-methoxy-benzamidine (11.3 g, 0.055 mol; see step (i) above) in 200 mL of ethanol was added 200 mg of PtO$_2$. The mixture was hydrogenated with constant bubbling of hydrogen for 4 h and subsequently filtered through Celite® and evaporated. Yield: 7.34 g (74%).

(iii) Boc-Pro-Pab(OMe)

To a suspension of Boc-Pro-OH (9.7 g, 0.045 mol), 4-aminomethyl-N-methoxy-benzamidine (7.34 g, 0.041 mol; see step (ii) above) and dimethylaminopyridine (7.8 g, 0.064 mol) in 300 mL of acetonitrile was added EDC base (11.7 mL, 0.068 mol). The mixture was stirred for 18 h, concentrated and partitioned between water and EtOAc. The organic layer was washed with water, aqueous sodium bicarbonate, dried (MgSO$_4$) and evaporated. The crude product was flash chromatographed on silica gel with EtOAc. Yield: 9.73 g (63%).

(iv) H-Pro-Pab(OMe)×2HCl

Boc-Pro-Pab(OMe) (9.7 g, 0.026 mol; see step (iii) above) was dissolved in 250 mL of EtOAc. The ice cooled solution was saturated with HCl(g) by bubbling for 5 min. The product precipitated immediately and 125 mL of absolute ethanol was added. The mixture was sonicated until most of the material had solidified. Diethyl ether (200 mL) was added and the suspension was filtered. A few lumps that had not solidified were again treated with absolute ethanol and diethyl ether. The solid was dried. Yield: 7.57 g (86%).

$^1$H NMR (400 MHz, CD$_3$OD) δ 7.74 (d, 2H), 7.58 (d, 2H), 4.55 (s, 2H), 4.38 (m, 1H), 3.98 (s, 3H), 3.45-3.3 (m, 2H), 2.50 (m, 1H), 2.15-2.0 (m, 3H)

(v) Ph(3-Cl)(5-OCHF$_2$)—(R)CH(OH)—C(O)-Pro-Pab(OMe)

Ph(3-Cl)(5-OCHF$_2$)—(R)CH(OH)C(O)OH (50 mg, 0.198 mmol; see Example 1(viii) above), H-Pro-Pab(OMe) (76 mg, 0.218 mmol, see step (iv) above) and PyBOP (115 mg, 0.218 mmol) were dissolved in 2 mL of DMF. Diisopropylethyl amine (104 mg, 0.80 mmol) was added and the mixture was stirred for 2.5 h. The mixture was poured into 50 mL of water and extracted three times with EtOAc and the combined organic phase was washed with brine, dried ($Na_2SO_4$) and evaporated. The residue was flash chromatographed on silica gel with EtOAc:MeOH (95:5). Yield: 37 mg (36%). Purity: 98%.

$^1$H NMR (400 MHz, CD$_3$OD, mixture of rotamers) δ 7.60 (d, 2H, major rotamer), 7.57 (d, 2H, minor rotamer), 7.4-7.1 (m, 5H), 6.89 (t, 1H, major rotamer), 6.87 (t, 1H, minor rotamer), 5.35 (s, 1H, major rotamer), 5.21 (s, 1H, minor rotamer), 4.72 (m, 1H, minor rotamer), 4.5-4.35 (m, 1H and 2H, major rotamer), 4.3-4.25 (m, 2H, minor rotamer), 3.814

(s, 3H, major rotamer), 3.807 (s, 3H, minor rotamer), 3.75-3.5 (m, 1H), 3.35 (m, 1H), 2.2-1.8 (m, 4H)

$^{13}$C-NMR (100 MHz; CD$_3$OD): (carbonyl and/or amidine carbons, mixture of rotamers) δ 173.3, 173.2, 171.3, 171.0, 153.9, 152.4

APCI-MS: (M+1)=511/513 m/z

EXAMPLE 34

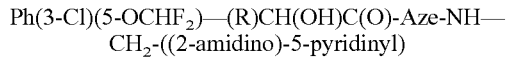
Ph(3-Cl)(5-OCHF$_2$)—(R)CH(OH)C(O)-Aze-NH—CH$_2$-((2-amidino)-5-pyridinyl)

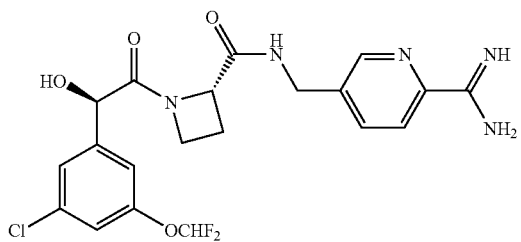

(i) 6-Cyanonicotinic acid

To a solution of the nicotinic acid N-oxide (51 g, 0.37 mol) in 1.2 L of DMF, NaCN (54 g, 1.1 mol) was added, followed by triethylamine (255 mL, 1.83 mol) and TMSCl (185 mL). The reaction mixture was stirred at 110° C. for 10 h, filtered and the filtrate was concentrated. The residue was dissolved in 100 mL of 2N HCl and extracted with methylene chloride. The organic layers were combined, concentrated and recrystallised from water to yield 12 g (22%) of the product.

(ii) 5-(Hydroxymethyl)pyridine-2-carbonitrile

To a solution of 6-cyanonicotinic acid (12 g, 0.081 mol; see step (i) above) in THF at 0° C., Et$_3$N (12.4 mL, 0.0892 mol) was added followed by ethyl chloroformate (8.53 mL, 0.0892 mol). The reaction mixture was stirred for 15 min and NaBH$_4$ (6.14 g, 0.162 mol) was added. Then the mixture was stirred at RT overnight, quenched with water and extracted with methylene chloride. The organic layer was concentrated and purified by column chromatography to yield 4 g (20%) of the alcohol.

(iii) 5-(Azidomethyl)pyridine-2-carbonitrile 5-(Hydroxymethyl)pyridine-2-carbonitrile (4 g, 0.03 mol; see step (ii) above) was dissolved in 25 mL of methylene chloride and cooled in an ice bath. Mesyl chloride (2.32 mL, 0.0300 mol) and then triethylamine (4.6 mL, 0.033 mol) were added dropwise. The reaction mixture was stirred and after work up the crude mesylate was treated with NaN$_3$ (7.35 g, 0.113 mol) in 20 mL of DMF. The reaction mixture was stirred at 40° C. for 2 h, diluted with water and extracted with ethyl acetate. The organic layer was concentrated to yield 3.95 g (83%) of the crude azide.

(iv) 5-(tert-Butoxycarbonylaminomethyl)pyridine-2-carbonitrile

To a solution of 5-(azidomethyl)pyridine-2-carbonitrile (3.95 g, 0.0248 mol; see step (iii) above) in 30 mL of THF and 10 mL of water, triphenyl phosphine (7.8 g, 0.0298 mol) was added and the resultant stirred for 24 h. Then, triethylamine (3.8 mL, 0.027 mol) was added, followed by Boc anhydride (5.4 g, 0.025 mol) and stirring for 2 h. The reaction mixture was partitioned between water and ethyl acetate. The organic layer was concentrated and purified by column chromatography to yield 2.1 g (36%) of the sub-title compound.

$^1$H NMR (300 MHz, CDCl$_3$) δ 8.6 (s, 1H), 8.0 (d, 1H), 8.9 (d, 1H), 4.1 (m, 2H), 1.4 (s, 9H)

(v) 5-(Aminomethyl)pyridine-2-carbonitrile×2 HCl 5-(tert-Butoxycarbonylaminomethyl)pyridine-2-carbonitrile (0.200 g, 0.86 mmol, see step (iv) above) was dissolved in 10 mL of EtOAc saturated with HCl(g) and was stirred for 30 min. The solvent was evaporated and 0.175 g (99%) of the sub-title compound was obtained as its dihydrochloride salt.

$^1$H NMR (500 MHz, D$_2$O) δ 8.79 (s, 1H), 8.17 (d, 1H), 8.05 (d, 1H), 4.38 (s, 2H)

(vi) Boc-Aze-NH—CH$_2$-5-Py(2-CN)

To a mixture of 5-(aminomethyl)pyridine-2-carbonitrile×2HCl (0.175 g, 0.85 mmol; see step (v) above), Boc-Aze-OH (0.201 g, 1.00 mmol) and TBTU (0.321 g, 1.00 mmol) in 5 mL of DMF was added dimethylaminopyridine (0.367 g, 3.00 mmol). The mixture was stirred overnight and subsequently poured into water and extracted three times with EtOAc. The combined organic phase was washed with aqueous sodium bicarbonate, dried (Na$_2$SO$_4$) and evaporated. The crude product started to crystallise and was used as such in the next step. Yield: 0.23 g (73%).

$^1$H NMR (500 MHz, CDCl$_3$) δ 8.66 (s, 1H), 8.2-7.8 (broad, 1H), 7.79 (d, 1H), 7.67 (d, 1H), 4.73 (m, 1H), 4.65-4.5 (m, 2H), 3.94 (m, 1H), 3.81 (m, 1H), 2.6.2.35 (m, 2H), 1.8 (broad, 1H), 1.45 (s, 9H)

(vii) H-Aze-NH—CH$_2$-5-Py(2-CN)×2HCl

Boc-Aze-NH—CH$_2$-5-Py(2-CN) (0.23 g, 0.73 mmol; see step (vi) above) was dissolved in 10 mL of EtOAc saturated with HCl(g) and was stirred for 30 min. The solvent was evaporated and 0.21 g (100%) of the sub-title compound was obtained as its dihydrochloride salt.

$^1$H NMR (500 MHz, D$_2$O) δ 8.64 (s, 1H), 8.0-7.9 (m, 2H), 5.19 (m, 1H), 4.65-4.55 (m, 2H), 4.20 (m, 1H), 4.03 (m, 1H), 2.88 (m, 1H), 2.64 (m, 1H)

(viii) Ph(3-Cl)(5-OCHF$_2$)—(R)CH(OH)—C(O)-Aze-NH—CH$_2$-5-Py(2-CN)

To a mixture of H-Aze-NH—CH$_2$-5-Py(2-CN)×2HCl (0.206 g, 0.713 mmol; see step (vii) above), Ph(3-Cl)(5-OCHF$_2$)—(R)CH(OH)C(O)OH (0.180 g, 0.713 mmol; see Example 1(viii) above) and PyBOP (0.408 g, 0.784 mmol) in 5 mL of DMF was added dimethylaminopyridine (0.367 g, 3.00 mmol). The mixture was stirred overnight and subsequently poured into water and extracted three times with EtOAc. The combined organic phase was washed with aqueous sodium bicarbonate, dried (Na$_2$SO$_4$) and evaporated. The crude product was flash chromatographed on silica gel with EtOAc gave a pure product. Yield: 0.197 g (61%).

$^1$H NMR (500 MHz, CDCl$_3$) δ 8.63 (m, 1H), 8.22 (bt, 1H), 7.78 (m, 1H), 7.67 (m, 1H), 7.21 (m, 1H), 7.16 (m, 1H), 7.04 (m, 1H), 6.56 (t, 1H), 4.97 (bd, 1H), 4.92 (m, 1H), 4.6-4.5 (m, 2H), 4.40 (bd, 1H), 4.18 (m, 1H), 3.80 (m, 1H), 2.69 (m, 1H), 2.46 (m, 1H), 1.92 (s, 1H)

APCI-MS: (M+1)=451/453 m/z (ix) Ph(3-Cl)(5-OCHF$_2$)—(R)CH(OH)—C(O)-Aze-NH—CH$_2$-((2-amidino)-5-pyridinyl)×HOAc Ph(3-Cl)(5-OCHF$_2$)—(R)CH(OH)—C(O)-Aze-NH—CH$_2$-5-Py(2-CN) (0.200 g, 0.444 mmol; see step (viii) above), ammonium acetate (1.00 g, 0.0130 mol) and N-acetylcysteine (2.00 g, 0.0122 mol) in 10 mL of methanol was heated at 50° C. for 2 days. Preparative RPLC with CH$_3$CN:0.1M NH$_4$OAc (30:79) and running the appropriate fractions again with CH$_3$CN:0.1M NH$_4$OAc (5:95-40:60) gave 60 mg (26%) of pure title compound as its acetate salt after freeze drying from water and acetonitrile. Purity: 100%.

$^1$H NMR (500 MHz, D$_2$O, mixture of rotamers) δ 8.68 (s, 1H, major rotamer), 8.62 (s, 1H, minor rotamer), 8.05-7.9 (m, 2H), 7.33 (m, 1H, rotamer), 7.27 (m, 1H, rotamer), 7.22 (m, 1H, rotamer), 7.17 (m, 1H, rotamer), 7.01 (m, 1H, rotamer), 6.84 (t, 1H), 5.32 (s, 1H, major rotamer), 5.20 (m, 1H, minor rotamer), 5.13 (s, 1H, minor rotamer), 4.88 (m, 1H, major rotamer), 4.65-4.55 (m, 2H, major rotamer), 4.45-4.35 (m, 1H, rotamer plus 1H, minor rotamer), 4.31 (d, 1H, minor rotamer), 4.2-4.05 (m, 1H plus 1H, rotamer), 2.80 (m, 1H, minor rotamer), 2.61 (m, 1H, major rotamer), 2.33 (m, 1H, major rotamer), 2.24 (m, 1H, minor rotamer), 1.93 (s, 3H)

$^{13}$C-NMR (100 MHz; D$_2$O): (carbonyl and/or amidine carbons, mixture of rotamers) δ 181.6, 173.3, 172.7, 172.6, 172.3, 162.6, 162.3

APCI-MS: (M+1)=468/470 m/z

EXAMPLE 35

Ph(3-Cl)(5-OCHF$_2$)—(R)CH(OH)C(O)-Aze-NH—CH$_2$-((2-methoxyamidino)-5-pyridinyl)

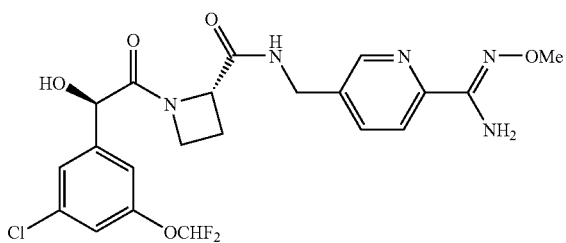

(i) Boc-NH—CH$_2$-[(2-(amino(hydroxylimino)methyl))-5-pyridinyl]

5-(tert-Butoxycarbonylaminomethyl)pyridine-2-carbonitrile (1.00 g, 4.29 mmol; see Example 34(iv) above) was dissolved in 10 mL of ethanol and hydroxylamine hydrochloride (0.894 g, 0.0129 mol) and triethyl amine (1.30 g, 0.0129 mol) were added. The mixture was stirred at room temperature for 6 days. The mixture was partitioned between water and methylene chloride. The aqueous layer was extracted with methylene chloride and the combined organic phase was washed with water, dried (Na$_2$SO$_4$) and evaporated. Yield: 0.96 g (84%).

$^1$H NMR (400 MHz, acetone-d$_6$) δ 9.01 (bs, 1H), 8.50 (bs, 1H), 7.87 (m, 1H), 7.70 (m, 1H), 6.58 (broad, 1H), 5.70 (broad, 2H), 4.31 (d, 2H), 1.41 (s, 9H)

(ii) Boc-Aze-NH—CH$_2$-(2-(amidino)-5-pyridinyl)×HOAc

This reaction was carried out according to the method described in Judkins et al, *Synth. Comm.* (1998) 4351. A suspension of Boc-NH—CH$_2$-[(2-(amino(hydroxylimino)methyl))-5-pyridinyl] (0.910 g, 3.42 mmol; see step (i) above), acetic anhydride (0.35 mL, 3.7 mmol) and 0.35 g of 10% Pd/C (50% moisture) in 100 mL of acetic acid was hydrogenated at a pressure of 5 atm. for 5 h. The mixture was filtered through Celite and concentrated. The residue was freeze-dried from water and acetonitrile to give 0.97 g (92%) of the sub-title compound.

$^1$H NMR (500 MHz, CD$_3$OD) δ 8.74 (s, 1H), 8.12 (d, 1H), 7.98 (d, 1H), 4.38 (s, 2H), 1.92 (s, 3H), 1.46 (s, 9H)

(iii) Boc-NH—CH$_2$-(2-(amino(trimethylsilylethylimino)methyl)-5-pyridinyl)

To a suspension of Boc-NH—CH$_2$-(2-(amidino)-5-pyridinyl)×HOAc (0.96 g, 3.1 mmol; see step (ii) above) in 75 mL of THF was added a solution of potassium carbonate (1.07 g, 7.7 mmol) and Teoc-p-nitrophenyl carbonate (1.14 g, 4.02 mmol) in 15 mL of water. The mixture was stirred overnight. An excess of glycine and potassium carbonate was added, and the reaction was continued for 2 h. The THF was evaporated and the remainder was extracted three times with EtOAc. The combined organic phase was washed with water, dried (Na$_2$SO$_4$) and evaporated. The product could be used without further purification.

$^1$H NMR (500 MHz, CDCl$_3$) δ 9.31 (broad, 1H), 8.52 (s, 1H), 8.41 (d, 1H), 8.35 (broad, 1H), 7.74 (d, 1H), 4.97 (broad, 1H), 4.39 (m, 2H), 4.26 (m, 2H), 1.46 (s, 9H), 1.14 (m, 2H), 0.07 (s, 9H)

(iv) H$_2$N—CH$_2$-(2-(amino(trimethylsilylethylimino)methyl)-5-pyridinyl)×2 HCl Boc-NH—CH$_2$-(2-(amino(trimethylsilylethylimino)methyl)-5-pyridinyl) (0.23 g, 0.58 mmol; see step (iii) above) was dissolved in 25 mL of EtOAc saturated with HCl(g) and stirred for 30 min. The solvent was evaporated and the product used without further purification. Yield: 9.21 g (98%).

$^1$H NMR (500 MHz, D$_2$O) δ 8.89 (s, 1H), 8.25 (s, 2H), 4.55 (m, 2H), 4.42 (s, 2H), 1.20 (m, 2H), 0.09 (s, 9H)

(v) Boc-Aze-NH—CH$_2$-(2-(amino(trimethylsilylethylimino)methyl)-5-pyridinyl)

To a solution of H$_2$N—CH$_2$-(2-(amino(trimethylsilylethylimino)methyl)-5-pyridinyl)×2HCl (0.21 g, 0.57 mmol; see step (iv) above), Boc-Aze-OH (0.127 g, 0.631 mmol), and TBTU (233 mg, 0.726 mmol) in 5 mL of DMF was added dimethylaminopyridine (269 mg, 2.20 mmol). The mixture was stirred overnight, poured into 100 mL of water and extracted with EtOAc three times. The combined organic phase was washed with aqueous sodium bicarbonate and water, dried (Na$_2$SO$_4$) and evaporated. The crude product was flash chromatographed on silica gel with EtOAc to give 170 mg (56%) of the desired product.

$^1$H NMR (500 MHz, CDCl$_3$) δ 9.33 (broad, 1H), 8.54 (s, 1H), 8.41 (d, 1H), 8.36 (broad, 1H), 7.75 (m, 1H), 4.72 (m, 1H), 4.56 (m, 2H), 4.26 (m, 2H), 3.93 (m, 1H), 3.80 (m, 1H), 2.6-2.4 (m, 2H), 1.42 (s, 9H), 1.14 (m, 2H), 0.07 (s, 9H)

(vi) H-Aze-NH—CH$_2$-(2-(amino(trimethylsilylethylimino)methyl)-5-pyridinyl)×2HCl Boc-Aze-NH—CH$_2$-(2-(amino(trimethylsilylethylimino)methyl)-5-pyridinyl) (170 mg, 0.356 mmol; see step (v) above) was dissolved in 25 mL of EtOAc saturated with HCl(g) and stirred for 30 min. The solvent was evaporated and the product used without further purification. Yield: 160 mg (100%).

$^1$H NMR (500 MHz, CD$_3$OD) δ 9.00 (m, 1H), 8.84 (m, 1H), 8.23 (d, 2H), 8.10 (m, 1H), 5.09 (m, 1H), 4.7-4.6 (m, 2H), 4.51 (m, 2H), 4.14 (m, 1H), 3.97 (m, 1H), 2.86 (m, 1H), 2.58 (m, 1H), 1.22 (m, 2H), 0.11 (s, 9H)

(vii) Ph(3-Cl)(5-OCHF$_2$)—(R)CH(OH)C(O)-Aze-NH—CH$_2$-(2-(amino(trimethylsilylethylimino)methyl)-5-pyridinyl)

To a solution of H-Aze-NH—CH$_2$-(2-(amino(trimethylsilylethylimino)-methyl)-5-pyridinyl)×2HCl (160 mg, 0.462 mmol; see step (vi) above), Ph(3-Cl)(5-OCHF$_2$)—(R)CH(OH)C(O)OH (131 mg, 0.462 mmol; see Example 1(viii) above) and PyBOP (263 mg, 0.505 mmol) in 5 mL of DMF was added diisopropylethyl amine (0.30 mL, 1.71 mmol). The mixture was stirred overnight, poured into 100 mL of water and extracted three times with EtOAc. The combined organic phase was washed with aqueous sodium bicarbonate and water, dried (Na$_2$SO$_4$) and evaporated. The crude product was flash chromatographed on silica gel with EtOAc:MeOH (95:5) to give 148 mg (52%) of the desired product.

(viii) Ph(3-Cl)(5-OCHF$_2$)—(R)CH(OH)C(O)-Aze-NH—CH$_2$-(2-(methoxyamino(trimethylsilylethylimino)methyl)-5-pyridinyl)

A suspension of Ph(3-Cl)(5-OCHF$_2$)—(R)CH(OH)—C(O)-Aze-NH—CH$_2$-(2-(methoxyamino(trimethylsilylethylimino)methyl)-5-pyridinyl) (148 mg, 0.242 mmol; see step (vii) above) and O-methylhydroxylamine (202 mg, 2.42 mmol) in 10 mL of acetonitrile was heated at 70° C. for 3 h. The mixture was partitioned between water and EtOAc. The aqueous layer was extracted twice with EtOAc and the combined organic phase was washed with water, dried (Na$_2$SO$_4$) and evaporated. The crude material was flash chromatographed on silica gel with EtOAc:MeOH (95:5) to give 44 mg (28%) of pure material.

$^1$H NMR (500 MHz, CDCl$_3$) δ 8.55 (m, 1H), 8.05 (bt, 1H), 7.70 (m, 1H), 7.58 (s, 1H), 7.56 (d, 1H), 7.22 (m, 1H), 7.16 (m, 1H), 7.03 (m, 1H), 6.50 (t, 1H), 4.92 (s, 1H), 4.89 (m, 1H), 4.55-4.45 (m, 2H), 4.38 (broad, 1H), 4.2-4.1 (m, 3H), 4.00 (s, 3H), 3.73 (m, 1H), 2.69 (m, 1H), 2.44 (m, 1H), 0.97 (m, 2H), 0.02 (s, 9H)

(ix) Ph(3-Cl)(5-OCHF$_2$)—(R)CH(OH)C(O)-Aze-NH—CH$_2$-((2-methoxyamidino)-5-pyridinyl)

Ph(3-Cl)(5-OCHF$_2$)—(R)CH(OH)C(O)-Aze-NH—CH$_2$-(2-(methoxyamino(trimethylsilylethylimino)methyl)-5-pyridinyl) (44 mg, 0.069 mmol; see step (viii) above) was dissolved in 2 mL of TFA and allowed to react for 1 h. The TFA was evaporated and the residue was partitioned between EtOAc and aqueous sodium bicarbonate. The aqueous layer was extracted with EtOAc and the combined organic phase was washed with water, dried (Na$_2$SO$_4$) and evaporated. Yield: 30 mg (88%). Purity: >95%.

$^1$H NMR (500 MHz, CDCl$_3$) δ 8.44 (m, 1H), 8.03 (bt, 1H), 7.91 (m, 1H), 7.60 (m, 1H), 7.19 (m, 1H), 7.13 (m, 1H), 7.00 (m, 1H), 6.52 (t, 1H), 5.6-5.45 (broad, 2H), 4.90 (s, 1H), 4.89 (m, 1H), 4.55-4.4 (m, 2H), 4.27 (broad, 1H), 4.12 (m, 1H), 3.92 (s, 3H), 2.68 (m, 1H), 2.41 (m, 1H)

$^{13}$C-NMR (100 MHz; CDCl$_3$): (carbonyl and/or amidine carbons) δ 173.0, 170.9, 152.6

APCI-MS: (M+1) 498/500 m/z

EXAMPLE 36

Ph(3-Cl)(5-OCHF$_2$)—(R)CH(OH)C(O)-Aze-NH—CH$_2$-((5-amidino)-2-pyrimidinyl)

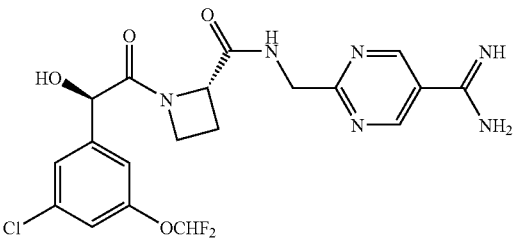

(i) 2-Amino-2-iminoethylcarbamate-AcOH

N-Boc-aminoacetonitrile (40.2 g, 257.4 mmol) and N-acetylcysteine (42.0 g, 257.4 mmol) were dissolved in methanol (300 mL) at 60° C. and ammonia was passed through for 18 h. The solvent was removed in vacuo. After ion exchange chromatography (Amberlite IRA-400 (AcOH)) and recrystallisation from acetone, 28.4 g (53%) of the sub-title compound was obtained as a white solid.

$^1$H NMR (300 MHz, CD$_3$OD) δ 4.41 (t, J=4.9 Hz, 1H), 4.01 (s, 2H), 2.91 (d, J=5.0 Hz, 2H), 2.01 (s, 3H), 1.46 (s, 9H)

(ii) 1,3-Bis(dimethylamino)-2-cyanotrimethinium perchlorate

A solution of 3-dimethylaminoacrylonitrile (25.0 g, 260.0 mmol) in chloroform (75 mL) was added dropwise to a solution of (chloromethylene)dimethylammonium chloride (50.0 g, 390.1 mmol) in chloroform (175 mL) at 0° C. The reaction mixture was stirred an additional 2 h at 0° C., then allowed to warm to room temperature overnight, then subsequently heated for 8 h under reflux. The solvent was removed in vacuo. The residue was added to a mixture of sodium perchlorate (110 g, 0.898 mmol) in water (150 mL) and ethanol (300 mL). The mixture was heated under reflux for 15 min then cooled and allowed to stand overnight in a refrigerator. The precipitate was collected and recrystallized from ethanol to yield 23.8 g (52%) of the sub-title compound as colorless needles.

mp: 140-141° C.

$^1$H NMR (300 MHz, CDCl$_3$) δ 8.24 (s, 2H), 3.59 (s, 6H), 3.51 (s, 6H)

(iii) Boc-NH—CH$_2$-(5-cyano)-2-pyrimidine

A mixture of t-butyl 2-amino-2-iminoethylcarbamate-AcOH (5.0 g, 23.8 mmol; see step (i) above) and 1,3-bis(dimethylamino)-2-cyanotrimethinium perchlorate (6.0 g, 23.8 mmol; see step (ii) above) in pyridine (300 mL) was stirred under nitrogen at 70-75° C. for 16 h and then heated under reflux for 6 h. The mixture was cooled to room temperature and the solvent was removed in vacuo. The residue was extracted with a hot mixture (1:1) of ethyl acetate and chloroform, filtered through a small pad of silica, and concentrated to give the crude product. Flash chromatography on silica eluting with chloroform gave 4.0 g (71%) of the title compound as colorless oil, which solidified upon standing.

mp: 86-87° C.

$R_f$=0.77 (silica, 3:2 Ethyl Acetate/Chloroform)

$^1$H NMR (300 MHz, DMSO-d$_6$) δ 9.25 (s, 2H), 7.39 (bt, 1H), 4.39 (d, J=6 Hz, 2H), 1.38 (s, 9H).

$^{13}$C NMR (750 MHz, DMSO-d$_6$) δ 170.4, 160.3, 155.8, 115.2, 106.9, 80.0, 46.3, 28.1

APCI-MS: (M+1)=235 m/z (iv) Boc-Aze-NH—CH$_2$-((5-cyano)-2-pyrimidinyl)

Boc-NH—CH$_2$-(5-cyano)-2-pyrimidine (1.14 g, 4.87 mmol; see step (iii) above) was dissolved in 50 mL of EtOAc saturated with HCl(g) and allowed to react for 1 h and concentrated. The residue was dissolved in 20 mL of DMF and cooled in an ice bath. Diisopropylethyl amine (3.5 mL, 0.020 mol), Boc-Aze-OH (1.08 g, 5.37 mmol) and HATU (2.80 g, 5.38 mmol) were added and the reaction mixture was stirred at room temperature overnight. The solvent was evaporated and the product was purified by preparative RPLC using CH$_3$CN:0.1M NH$_4$OAc (40:60). The acetonitrile was evaporated and the aqueous layer was extracted three times with EtOAc. The combined organic layer was dried (MgSO$_4$) and evaporated.

Yield: 1.12 g (72%).

$^1$H NMR (400 MHz, CDCl$_3$) δ 8.95 (s, 2H), 4.82 (d, 2H), 4.74 (m, 1H), 3.95 (m, 1H), 3.84 (m, 1H), 2.6-2.4 (m, 2H), 1.47 (s, 9H)

(v) Boc-Aze-NH—CH$_2$-((5-amidino)-2-pyrimidinyl)×HOAc

A solution of Boc-Aze-NH—CH$_2$-((5-cyano)-2-pyrimidinyl) (0.83 g, 2.6 mmol; see step (iv) above), N-acetylcysteine (0.43 g, 2.6 mmol) and ammonium acetate (0.60 g, 7.8 mmol) in 10 mL of methanol was heated at 60° C. under nitrogen for 2 days. The solvent was evaporated and the crude material was purified by preparative RPLC using a gradient of CH$_3$CN:0.1M NH$_4$OAc (5:95 to 100:0). The fractions of interest were freeze dried to give 1.0 g (93%) of the desired material.

$^1$H NMR (300 MHz, D$_2$O, signals obscured by the HDO signal) δ 9.17 (s, 2H), 4.1-3.9 (m, 2H), 2.60 (m, 1H), 2.29 (m, 1H), 1.93 (s, 3H), 1.44 (s, 9H)

(vi) Boc-Aze-NH—CH$_2$-[(5-(amino(trimethylsilylethylimino)methyl))-2-pyrimidinyl]

To a suspension of Boc-Aze-NH—CH$_2$-((5-amidino)-2-pyrimidinyl)×HOAc (0.95 g, 2.41 mmol; see step (v) above) in 50 mL of THF was added a solution of Teoc-p-nitrophenyl carbonate (0.85 g, 3.0 mmol) and potassium carbonate (1.0 g, 7.2 mmol) in 10 mL of water. The mixture was stirred for 24 h, concentrated and partitioned between water and methylene chloride. The organic layer was washed twice with saturated aqueous sodium bicarbonate, dried (Na$_2$SO$_4$) and evaporated. The crude product was flash chromatographed on silica gel with heptane:EtOAc (1:1). Yield: 1.04 g (90%).

$^1$H NMR (300 MHz, CDCl$_3$) δ 9.16 (s, 2H), 4.80 (d, 2H), 4.73 (m, 1H), 4.26 (m, 2H), 4.0-3.8 (m, 2H), 2.6-2.4 (m, 2H), 1.47 (s, 9H), 1.12 (m, 2H), 0.07 (s, 9H)

(vii) Ph(3-Cl)(5-OCHF$_2$)—(R)CH(OH)C(O)-Aze-NH—CH$_2$-[(5-(amino(trimethylsilylethyliminio)methyl))-2-pyrimidinyl]

Boc-Aze-NH—CH$_2$-[(5-(amino(trimethylsilylethylimino)methyl))-2-pyrimidinyl] (0.209 g, 0.437 mmol; see step (vi) above) was dissolved in 25 mL of EtOAc saturated with HCl(g) and allowed to react for 15 min. The solvent was evaporated and the remainder was dissolved in 4 mL of DMF. Ph(3-Cl)(5-OCHF$_2$)—(R)CH(OH)C(O)OH (0.100 g, 0.396 mmol; see Example 1(viii) above), PyBOP (0.231 g, 0.444 mmol) and diisopropylethyl amine (0.208 g, 1.61 mmol) were added, and the mixture was stirred for 80 min. The reaction mixture was poured into 100 mL of water and extracted three times with EtOAc. The combined organic layer was washed with brine, dried (Na$_2$SO$_4$) and evaporated. The crude product was purified by preparative RPLC using CH$_3$CN:0.1M NH$_4$OAc (1:1). Yield: 63 mg (26%).

$^1$H NMR (400 MHz, CDCl$_3$, mixture of rotamers) δ 9.3 (broad, 1H), 9.03 (s, 2H, minor rotamer), 9.00 (s, 2H, major rotamer), 8.25 (m, 1H, major rotamer), 7.9 (broad, 1H), 7.80 (m, 1H, minor rotamer), 7.2-6.9 (m, 3H), 6.50 (t, 1H), 5.14 (s, 1H, minor rotamer), 5.08 (m, 1H, minor rotamer), 4.94 (s, 1H, major rotamer), 4.80 (m, 1H, major rotamer), 4.7-4.4 (m, 2H), 4.3-3.9 (m, 3H), 3.74 (m, 1H, major rotamer), 2.7-2.1 (m, 0.2H), 1.03 (m, 2H), 0.01 (s, 9H)

(viii) Ph(3-Cl)(5-OCHF$_2$)—(R)CH(OH)C(O)-Aze-NH—CH$_2$-((5-amidino)-2-pyrimidinyl)×TFA Ph(3-Cl)(5-OCHF$_2$)—(R)CH(OH)C(O)-Aze-NH—CH$_2$-[(5-(amino(trimethylsilylethylimino)methyl))-2-pyrimidinyl] (21 mg, 0.034 mmol; see step (vii) above) was dissolved in 0.5 mL of methylene chloride and cooled in an ice bath. TFA (2 mL) was added and the mixture was stirred for 60 min and then concentrated. The product was freeze-dried from water and acetonitrile. Yield: 20 mg (100%). Purity: 100%.

$^1$H NMR (400 MHz, CD$_3$OD, mixture of rotamer, signals obscured by the HDO signal) δ 9.08 (s, 2H), 7.4-7.1 (m, 3H), 6.88 (t, 1H, major rotamer), 6.85 (t, 1H, minor rotamer), 5.30 (m, 1H, minor rotamer), 5.22 (s, 1H, minor rotamer), 5.20 (s, 1H, major rotamer), 4.73 (m, 1H, major rotamer), 4.34 (m, 1H, rotamer), 4.21 (m, 1H, rotamer), 4.15-3.95 (m, 2H, rotamers), 2.73 (m, 1H, rotamer), 2.57 (m, 1H, rotamer), 2.45-2.25 (m, 2H, rotamers)

$^{13}$C-NMR (100 MHz; CD$_3$OD): (carbonyl and/or amidine carbons, mixture of rotamers) δ 173.0, 172.6, 172.1, 171.0, 163.4.

APCI-MS: (M+1)=469/471 m/z

EXAMPLE 37

Ph(3-Cl)(5-OCHF$_2$)—(R)CH(OH)C(O)-Aze-NH—CH$_2$-((5-methoxyamidino)-2-pyrimidinyl)

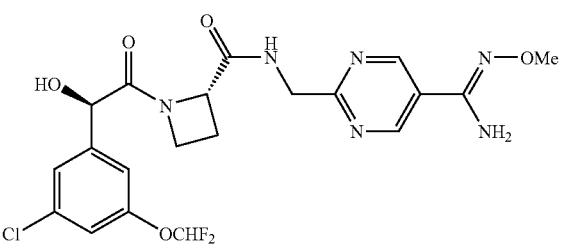

(i) Ph(3-Cl)(5-OCHF$_2$)—(R)CH(OH)C(O)-Aze-NH—CH$_2$-[(5-(methoxyamino-(trimethylsilylethylimino)methyl))-2-pyrimidinyl]

A suspension of Ph(3-Cl)(5-OCHF$_2$)—(R)CH(OH)C(O)-Aze-NH—CH$_2$-[(5-(amino(trimethylsilylethylimino)methyl))-2-pyrimidinyl] (40 mg, 0.065 mmol; see Example 36(vii) above) and O-methylhydroxylamine (33 mg, 0.40 mmol) in 3 mL of acetonitrile was heated at 70° C. for 3 h. The mixture was partitioned between water and EtOAc. The aqueous layer was extracted twice with EtOAc and the combined organic phase was washed with water, dried ($Na_2SO_4$) and evaporated. Yield: 33 mg (79%).

$^1$H NMR (400 MHz, $CDCl_3$, mixture of rotamers) δ 8.76 (s 2H, major rotamer), 8.70 (s, 2H, rotamer), 8.18 (m, 1H), 7.62 (s, 1H), 7.4-6.9 (m, 4H), 6.50 (bt, 1H), 5.3-4.5 (m, 4H), 4.2-4.05 (m, 3H), 3.96 (s, 3H), 3.68 (m, 1H), 2.8-2.2 (m, 2H), 2.1 (broad, 1H), 0.96 (m, 2H), 0.01 (s, 9H)

(ii) Ph(3-Cl)(5-CHF$_2$)—(R)CH(OH)C(O)-Aze-NH—CH$_2$-((5-methoxyamidino)-2-pyrimidinyl)

Ph(3-Cl)(5-OCHF$_2$)—(R)CH(OH)C(O)-Aze-NH—CH$_2$-[(5-(methoxyamino-(trimethylsilylethylimino)methyl))-2-pyrimidinyl] (33 mg, 0.052 mmol; see step (i) above) was dissolved in 0.5 mL of methylene chloride and cooled in an ice bath. TFA (2 mL) was added and the mixture was stirred for 2 h and then concentrated. The product was freeze dried from water and acetonitrile. Yield: 31 mg (81%). Purity: 100%.

$^1$H NMR (400 MHz, $CD_3OD$, mixture of rotamer signals obscured by the HDO signal) δ 8.96 (s, 2H, rotamer), 8.94 (s, 2H, rotamer), 7.4-7.3 (m, 1H), 7.2-7.1 (m, 2H), 6.88 (t, 1H, rotamer), 6.85 (t, 1H, rotamer), 5.29 (m, 1H, rotamer), 5.24 (s, 1H, rotamer), 5.20 (s, 1H, rotamer), 4.75-4.55 (m, 2H), 4.33 (m, 1H, rotamer), 4.19 (m, 1H, rotamer), 4.15-3.95 (m, 2H, rotamers), 3.88 (s, 3H, rotamer), 3.86 (s, 3H, rotamer), 2.72 (m, 1H, rotamer), 2.56 (m, 1H, rotamer), 2.45-2.25 (m, 2H, rotamers)

$^{13}$C-NMR (100 MHz; $CD_3OD$): (carbonyl and/or amidine carbons, mixture of rotamers) δ 172.8, 172.6, 172.1, 171.8, 167.8, 167.7, 155.1, 152.3, 152.1

APCI-MS: (M+1)=499/501 m/z

EXAMPLE 38

Ph(3-Cl)(5-OCHF$_2$)—(R)CH(OH)C(O)-Aze-Pab(3-F)

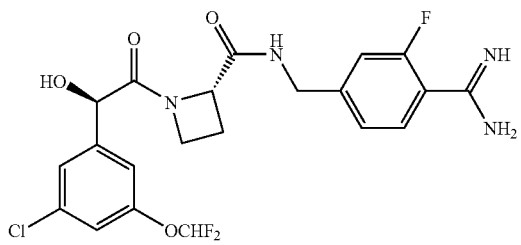

(i) 2-Fluoro-4-vinylbenzonitrile

A solution of 4-bromo-2-fluorobenzonitrile (4.92 g, 0.0246 mol), vinyltributyltin (0.78 g, 0.246 mol), and tetrakistriphenylphosphine (0.67 g, 0.58 mmol) in 250 mL of toluene was refluxed under nitrogen overnight. The solvent was evaporated and the residue was flash chromatographed on silica gel with heptane:$CH_2Cl_2$ (1:1) to pure $CH_2Cl_2$. A colourless oil was obtained that crystallised. Yield: 3.0 g (82%).

$^1$H NMR (300 MHz, $CDCl_3$) δ 7.56 (m, 1H), 7.3-7.2 (m, 2H), 6.69 (m, 1H), 5.89 (d, 1H), 5.51 (d, 1H)

(ii) 2-Fluoro-4-hydroxymethylbenzonitrile

Into a cooled solution (−78° C.) of 2-fluoro-4-vinylbenzonitrile (1.3 g, 8.8 mmol; see step (i) above) in 40 mL of $CH_2Cl_2$ and 5 mL of methanol was to bubbled ozone (50 L/h, 29 g/m$^3$) for 30 min. Argon was subsequently bubbled through to remove excess ozone. Sodium borohydride (0.67 g, 0.018 mol) was added and the cooling bath was removed. The mixture was stirred and allowed to react for 1 h. The mixture was evaporated and 2M HCl was added. The mixture was extracted twice with diethyl ether and the combined ether fraction was dried ($Na_2SO_4$) and evaporated. The crude product crystallised. Yield: 1.1 g (81%).

$^1$H NMR (300 MHz, $CDCl_3$) δ 7.59 (m, 1H), 7.3-7.2 (m, 2H), 4.79 (d, 2H), 2.26 (t, 1H)

(iii) 4-Cyano-3-fluorobenzyl methanesulfonate

2-Fluoro-4-hydroxymethylbenzonitrile (1.3 g, 8.6 mmol; see step (ii) above) was dissolved in 50 mL of $CH_2Cl_2$ and cooled on an ice bath. Triethylamine (0.87 g, 8.6 mmol) and methanesulfonyl chloride (0.99 g, 8.7 mmol) were added. After stirring for 1.5 h the reaction mixture was washed with 1M HCl. The organic phase was dried ($Na_2SO_4$) and evaporated. The product could be used without purification. Yield of a colourless oil: 1.8 g (92%).

$^1$H NMR (400 MHz, $CDCl_3$) δ 7.66 (m, 1H), 7.35-7.3 (m, 2H), 5.26 (s, 2H), 3.07 (s, 3H)

(iv) 4-Azidomethyl-2-fluorobenzonitrile

To an ice cooled solution of 4-cyano-3-fluorobenzyl methanesulfonate (1.8 g, 7.9 mmol; see step (iii) above) was added sodium azide (0.80 g, 0.012 mol). The mixture was stirred overnight and then poured into 200 mL of water and extracted three times with diethyl ether. The combined ethereal phase was washed five times with water, dried ($Na_2SO_4$) and evaporated. The crude colourless oil could be used without further purification. Yield: 1.2 g (87%).

$^1$H NMR (300 MHz, $CDCl_3$) δ 7.64 (m, 1H), 7.25-7.18 (m, 2H), 4.47 (s, 2H)

(v) 4-Aminomethyl-2-fluorobenzonitrile

To a suspension of stannous chloride dihydrate (0.45 g, 2.4 mmol) in 20 mL of acetonitrile under stirring was added thiophenol (1.07 g, 9.7 mmol) and triethylamine (0.726 μg, 7.17 mmol). Thereafter was added a solution of 4-azidomethyl-2-fluorobenzonitrile (0.279 g, 1.58 mmol; see step (iv) above) in a few mLs of acetonitrile. After 1.5 h, the azide was consumed and the solvent was evaporated. The residue was dissolved in methylene chloride and washed three times with 2M NaOH. The organic phase was extracted twice with 1M HCl. The combined acidic aqueous phase was washed with methylene chloride and then made alkaline with 2M NaOH and extracted three times with methylene chloride. The organic phase was dried ($Na_2SO_4$) and evaporated to give 0.172 g (72%) of the desired sub-title compound which could be used without purification.

$^1$H NMR (400 MHz, $CDCl_3$) δ 7.58 (m, 1H), 7.3-7.2 (m, 2H), 3.98 (s, 2H), 1.55-1.35 (broad, 2H)

(vi) Boc-Aze-NHCH$_2$-Ph(3-F, 4-CN)

To an ice cooled solution of Boc-Aze-OH (0.194 g, 0.96 mmol) in 5 mL of DMF was added TBTU (0.50 g, 9.6 mmol).

After 30 min another solution, comprising 4-aminomethyl-2-fluorobenzonitrile (0.17 g, 0.81 mmol; see step (v) above) and diisopropylethyl amine (0.326 g, 2.53 mmol) in 7 mL of DMF was added. The resulting solution was stirred overnight at room temperature. The solvent was evaporated and the product was purified by preparative RPLC using $CH_3CN$:0.1M $NH_4OAc$ (50:50). Freeze-drying gave 0.237 g (74%) of the desired sub-title compound.

$^1H$ NMR (300 MHz, $CD_3OD$) δ 7.70 (m, 1H), 7.35-7.25 (m, 2H), 4.65-4.35 (m, 3H), 4.0-3.85 (m, 2H), 2.51 (m, 1H), 2.19 (m, 1H), 1.40 (s, 9H)

(vii) Ph(3-Cl)(5-OCHF$_2$)—(R)CH(OH)C(O)-Aze-NHCH$_2$-Ph(3-F, 4-CN)

Boc-Aze-NHCH$_2$-Ph(3-F, 4-CN) (0.118 g, 0.354 mmol; from step (vi) above) was dissolved in 30 mL of EtOAc saturated with HCl(g). The reaction was stirred for 20 min and evaporated. The resulting dihydrochloride and HATU (0.152 g, 0.400 mmol) were dissolved in 5 mL of DMF. That solution was added to an ice cooled solution of Ph(3-Cl)(5-OCHF$_2$)—(R)CH(OH)C(O)OH (0.101 g, 0.400 mmol; see Example 1(viii) above) in 5 mL of DMF. The reaction was stirred overnight at ambient temperature. The solvent was evaporated and the product was purified by preparative RPLC with $CH_3CN$:0.1M $NH_4OAc$ (50:50). Freeze-drying gave 0.130 g (77%) of the desired sub-title compound.

$^1H$ NMR (500 MHz, $CD_3OD$ mixture of rotamers) δ 7.7-7.6 (m, 1H), 7.35-7.1 (m, 5H), 6.88 (t, 1H, rotamer), 6.86 (t, 1H, rotamer), 5.25-5.1 (m, 1H plus minor rotamer from the following proton), 4.80 (m, 1H, major rotamer), 4.6-4.4 (m, 2H), 4.36 (m, 1H, major rotamer), 4.18 (m, 1H, major rotamer), 4.07 (m, 1H, minor rotamer), 3.98 (m, 1H, minor rotamer), 2.70 (m, 1H, minor rotamer), 2.53 (m, 1H, major rotamer), 2.29 (m, 1H, major rotamer), 2.16 (m, 1-H, minor rotamer)

(viii) Ph(3-Cl)(5-OCHF$_2$)—(R)CH(OH)C(O)-Aze-Pab(3-F)

Ph(3-Cl)(5-OCHF$_2$)—(R)CH(OH)C(O)-Aze-NHCH$_2$-Ph(3-F, 4-CN) (0.130 g, 0.278 mmol; see step (vii) above) was dissolved in 80 mL of ethanol saturated with HCl(g). The mixture was allowed to react at room temperature overnight. The solvent was evaporated and the residue was re-dissolved in 100 mL of ethanol saturated with $NH_3(g)$. The reaction was allowed to proceed slowly at room temperature for two days. The temperature was raised to 50° C. and the reaction continued for another 3 days. The starting material was consumed and the solvent was evaporated. The product was purified by preparative RPLC and freeze-dried to give 17 mg (13%) of the title compound as its HOAc salt.

$^1H$ NMR (600 MHz, $CD_3OD$ mixture of rotamers) δ 7.65-7.6 (m, 1H), 7.4-7.3 (m, 3H), 7.25-7.1 (m, 2H), 7.15-6.7 (m, 1H), 5.25-5.1 (m, 1H plus minor rotamer of the following proton), 4.8 (m, 1H, major rotamer partially hidden by $CD_3OH$), 4.6-3.95 (m, 4H), 2.69 (m, 1H, minor rotamer), 2.56 (m, 1H, major rotamer), 2.28 (m, 1H, major rotamer), 2.14 (m, 1H, minor rotamer), 1.90 (s, 3H)

$^{13}C$-NMR (100 MHz; $CD_3OD$): (carbonyl and/or amidine carbons, mixture of rotamers) δ 180.6, 173.4, 173.1, 172.9, 164.5, 162.3, 159.8

APCI-MS: (M+1)=485/487 m/z

EXAMPLE 39

Ph(3-Cl)(5-OCHF$_2$)—(R)CH(OH)C(O)-Aze-Pab(2,6-diF)

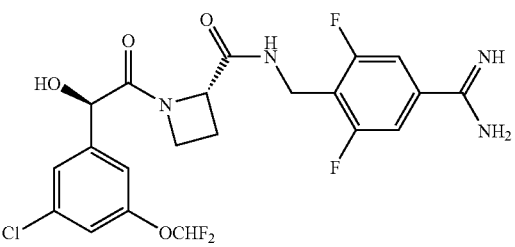

(i) 2,6-Difluoro-4[(methylsulfinyl)(methylthio)methyl]benzonitrile (Methylsulfinyl)(methylthio)methane (7.26 g, 0.0584 mol) was dissolved in 100 mL of dry THF under argon and was cooled to −78° C. Butyllithium in hexane (16 mL 1.6M, 0.0256 mol) was added dropwise with stirring. The mixture was stirred for 15 min. Meanwhile, a solution of 3,4,5-trifluorobenzonitrile (4.0 g, 0.025 mmol) in 100 mL of dry THF was cooled to −78° C. under argon and the former solution was added through a cannula to the latter solution over a period of 35 min. After 30 min, the cooling bath was removed and when the reaction had reached room temperature it was poured into 400 mL of water. The THF was evaporated and the remaining aqueous layer was extracted three times with diethyl ether. The combined ether phase was washed with water, dried ($Na_2SO_4$) and evaporated. Yield: 2.0 g (30%).

$^1H$ NMR (500 MHz, $CDCl_3$) δ 7.4-7.25 (m, 2H), 5.01 (s, 1H, diasteromer), 4.91 (s, 1H, diasteromer), 2.88 (s, 3H, diasteromer), 2.52 (s, 3H, diasteromer), 2.49 (s, 3H, diasteromer), 2.34 (s, 3H, diasteromer), 1.72 (broad, 1H)

(ii) 2,6-Difluoro-4-formylbenzonitrile 2,6-Difluoro-4[(methylsulfinyl)(methylthio)methyl]benzonitrile (2.17 g, 8.32 mmol; see step (i) above) was dissolved in 90 mL of THF and 3.5 mL of concentrated sulfuric acid was added. The mixture was left at room temperature for 3 days and subsequently poured into 450 mL of water. Extraction three times with EtOAc followed and the combined ethereal phase was washed twice with aqueous sodium bicarbonate and with brine, dried ($Na_2SO_4$) and evaporated. Yield: 1.36 g (98%). The position of the formyl group was established by $^{13}C$ NMR. The signal from the fluorinated carbons at 162.7 ppm exhibited the expected coupling pattern with two coupling constants in the order of 260 Hz and 6.3 Hz respectively corresponding to an ipso and a meta coupling from the fluorine atoms.

$^1H$ NMR (400 MHz, $CDCl_3$) δ 10.35 (s, 1H), 7.33 (m, 2H)

(iii) 2,6-Difluoro-4-hydroxymethylbenzonitrile 2,6-Difluoro-4-formylbenzonitrile (1.36 g, 8.13 mmol; see step (ii) above) was dissolved in 25 mL of methanol and cooled on an ice bath. Sodium borohydride (0.307 g, 8.12 mmol) was added in portions with stirring and the reaction was left for 65 min. The solvent was evaporated and the residue was partitioned between diethyl ether and aqueous sodium bicarbonate. The ethereal layer was washed with more aqueous sodium bicarbonate and brine, dried (Na$_2$SO$_4$) and evaporated. The crude product crystallised soon and could be used without further purification. Yield: 1.24 g (90%).

$^1$H NMR (400 MHz, CDCl$_3$) δ 7.24 (m, 2H), 4.81 (s, 2H), 2.10 (broad, 1H)

(iv) 4-Cyano-2,6-difluorobenzyl methanesulfonate

To an ice cooled solution of 2,6-difluoro-4-hydroxymethylbenzonitrile (1.24 g, 7.32 mmol; see step (iii) above) and methanesulfonyl chloride (0.93 g, 8.1 mmol) in 60 mL of methylene chloride was added triethylamine (0.81 g, 8.1 mmol) with stirring. After 3 h at 0° C., the mixture was washed twice with 1M HCl and once with water, dried (Na$_2$SO$_4$) and evaporated. The product could be used without further purification. Yield: 1.61 g (89%).

$^1$H NMR (300 MHz, CDCl$_3$) δ 7.29 (m, 2H), 5.33 (s, 2H), 3.07 (s, 3H)

(v) 4-Azidomethyl-2,6-difluorobenzonitrile

A mixture of 4-cyano-2,6-difluorobenzyl methanesulfonate (1.61 g, 6.51 mmol; see step (iv) above) and sodium azide (0.72 g, 0.0111 mol) in 10 mL of water and 20 mL of DMF was stirred at room temperature overnight. The resultant was subsequently poured into 200 mL of water and extracted three times with diethyl ether. The combined ethereal phase was washed five times with water, dried (Na$_2$SO$_4$) and evaporated. A small sample was evaporated for NMR purposes and the product crystallised. The rest was evaporated cautiously but not until complete dryness. Yield (theoretically 1.26 g) was assumed to be almost quantitative based on NMR and analytical HPLC.

$^1$H NMR (400 MHz, CDCl$_3$) δ 7.29 (m, 2H), 4.46 (s, 2H)

(vi) 4-Aminomethyl-2,6-difluorobenzonitrile

This reaction was carried out according to the procedure described in *J. Chem. Res.* (M) (1992) 3128. To a suspension of 520 mg of 10% Pd/C (50% moisture) in 20 mL of water was added a solution of sodium borohydride (0.834 g, 0.0221 mol) in 20 mL of water. Some gas evolution resulted. 4-Azidomethyl-2,6-difluorobenzonitrile (1.26 g, 6.49 mmol; see step (v) above) was dissolved in 50 mL of THF and added to the aqueous mixture on an ice bath over 15 min. The mixture was stirred for 4 h, whereafter 20 mL of 2M HCl was added and the mixture was filtered through Celite. The Celite was rinsed with more water and the combined aqueous phase was washed with EtOAc and subsequently made alkaline with 2M NaOH. Extraction three times with methylene chloride followed and the combined organic phase was washed with water, dried (Na$_2$SO$_4$) and evaporated. Yield: 0.87 g (80%).

$^1$H NMR (400 MHz, CDCl$_3$) δ 7.20 (m, 2H), 3.96 (s, 2H), 1.51 (broad, 2H)

(vii) 2,6-Difluoro-4-tert-butoxycarbonylaminomethylbenzonitrile

A solution of 4-aminomethyl-2,6-difluorobenzonitrile (0.876 g, 5.21 mmol; see step (vi) above) was dissolved in 50 mL of THF and di-tert-butyl dicarbonate (1.14 g, 5.22 mmol) in 10 mL of THF was added. The mixture stirred for 3.5 h. The THF was evaporated and the residue was partitioned between water and EtOAc. The organic layer was washed three times with 0.5 M HCl and water, dried (Na$_2$SO$_4$) and evaporated. The product could be used without further purification. Yield: 1.38 g (99%).

$^1$H NMR (300 MHz, CDCl$_3$) δ 7.21 (m, 2H), 4.95 (broad, 1H), 4.43 (broad, 2H), 1.52 (s, 9H)

(viii) Boc-Pab(2,6-diF)(OH)

A mixture of 2,6-difluoro-4-tert-butoxycarbonylaminomethylbenzonitrile (1.38 g, 5.16 mmol; see step (vii) above), hydroxylamine hydrochloride (1.08 g, 0.0155 mol) and triethylamine (1.57 g, 0.0155 mol) in 20 mL of ethanol was stirred at room temperature for 36 h. The solvent was evaporated and the residue was partitioned between water and methylene chloride. The organic layer was washed with water, dried (Na$_2$SO$_4$) and evaporated. The product could be used without further purification. Yield: 1.43 g (92%).

$^1$H NMR (500 MHz, CD$_3$OD) δ 7.14 (m, 2H), 4.97 (broad, 1H), 4.84 (broad, 2H), 4.40 (broad, 2H), 1.43 (s, 9H)

(ix) Boc-Pab(2,6-diF)×HOAc

This reaction was carried out according to the procedure described by Judkins et al, *Synth. Comm.* (1998) 4351. Boc-Pab(2,6-diF)(OH) (1.32 g, 4.37 mmol; see step (viii) above), acetic anhydride (0.477 g, 4.68 mmol) and 442 mg of 10% Pd/C (50% moisture) in 100 mL of acetic acid was hydrogenated at 5 atm pressure for 3.5 h. The mixture was filtered through Celite, rinsed with ethanol and evaporated. The residue was freeze-dried from acetonitrile and water and a few drops of ethanol. The sub-title product could be used without further purification. Yield: 0.1.49 g (99%).

$^1$H NMR (400 MHz, CD$_3$OD) δ 7.45 (m, 2H), 4.34 (s, 2H), 1.90 (s, 3H), 1.40 (s, 9H)

(x) Boc-Pab(2,6-diF)(Teoc)

To a solution of Boc-Pab(2,6-diF)×HOAc (1.56 g, 5.49 mmol; see step (ix) above) in 100 mL of THF and 1 mL of water was added 2-(trimethylsilyl)ethyl p-nitrophenyl carbonate (1.67 g, 5.89 mmol). A solution of potassium carbonate (1.57 g, 0.0114 mol) in 20 mL of water was added dropwise over 5 min. The mixture was stirred overnight. The THF was evaporated and the residue was partitioned between water and methylene chloride. The aqueous layer was extracted with methylene chloride and the combined organic phase was washed twice with aqueous sodium bicarbonate, dried (Na$_2$SO$_4$) and evaporated. Flash chromatography on silica gel with heptane/EtOAc=2/1 gave 1.71 g (73%) of pure compound.

$^1$H NMR (400 MHz, CDCl$_3$) δ 7.43 (m, 2H), 4.97 (broad, 1H), 4.41 (broad, 2H), 4.24 (m, 2H), 1.41 (s, 9H), 1.11 (m, 2H), 0.06 (s, 9H)

(xi) Boc-Aze-Pab(2,6-diF)(Teoc)

Boc-Pab(2,6-diF)(Teoc) (1.009 g, 2.35 mmol; see step (x) above) was dissolved in 50 mL of EtOAc saturated with HCl(g). The mixture was left for 10 min., evaporated and dissolved in 18 mL of DMF, and then cooled on an ice bath. Boc-Aze-OH (0.450 g, 2.24 mmol), PyBOP (1.24 g, 2.35 mmol) and lastly diisopropylethyl amine (1.158 g, 8.96 mmol) were added; The reaction mixture was stirred for 2 h and then poured into 350 mL of water and extracted three times with EtOAc. The combined organic phase was washed with brine, dried (Na$_2$SO$_4$) and evaporated. Flash chromatography on silica gel with heptane:EtOAc (1:3) gave 1.097 g (96%) of the desired compound.

$^1$H NMR (500 MHz, CDCl$_3$) δ 7.46 (m, 2H), 4.65-4.5 (m, 3H), 4.23 (m, 2H), 3.87 (m, 1H), 3.74 (m, 1H), 2.45-2.3 (m, 2H), 1.40 (s, 9H), 1.10 (m, 2H), 0.05 (s, 9H)

(xii) Ph(3-Cl)(5-OCHF$_2$)—(R)CH(OH)C(O)-Aze-Pab(2,6-diF)(Teoc)

Boc-Aze-Pab(2,6-diF)(Teoc) (0.256 g, 0.500 mmol; see step (xi) above) was dissolved in 20 mL of EtOAc saturated with HCl(g). The mixture was left for 10 min. and evaporated and dissolved in 5 mL of DMF. Ph(3-Cl)(5-OCHF$_2$)—(R)CH(OH)C(O)OH (0.120 g, 0.475 mmol; see Example 1(viii) above), PyBOP (0.263 g, 0.498 mmol) and lastly diisopropylethyl amine (0.245 g, 1.89 mmol were added. The reaction mixture was stirred for 2 h and then poured into 350 mL of water and extracted three times with EtOAc. The combined organic phase was washed with brine, dried (Na$_2$SO$_4$) and evaporated. Flash chromatography on silica gel with EtOAc gave 0.184 g (60%) of the desired sub-title compound.

$^1$H NMR (400 MHz, CD$_3$OD, mixture of rotamers) δ 7.55-7.45 (m, 2H), 7.32 (m, 1H, major rotamer), 7.27 (m, 1H, minor rotamer), 7.2-7.1 (m, 2H), 6.90 (t, 1H, major rotamer), 6.86 (t, 1H, minor rotamer), 5.15 (s, 1H, major rotamer), 5.12 (m, 1H, minor rotamer), 5.06 (s, 1H, minor rotamer), 4.72 (m, 1H, major rotamer), 4.6-4.45 (m, 2H), 4.30 (m, 1H, major rotamer), 4.24 (m, 2H), 4.13 (m, 1H, major rotamer), 4.04 (m, 1H, minor rotamer), 3.95 (m, 1H, minor rotamer), 2.62 (m, 1H, minor rotamer), 2.48 (m, 1H, major rotamer), 2.22 (m, 1H, major rotamer), 2.10 (m, 1H, minor rotamer), 1.07 (m, 2H), 0.07 (m, 9H)

(xiii) Ph(3-Cl)(5-OCHF$_2$)—(R)CH(OH)C(O)-Aze-Pab(2,6-diF)

Ph(3-Cl)(5-OCHF$_2$)—(R)CH(OH)C(O)-Aze-Pab(2,6-diF)(Teoc) (81 mg, 0.127 mmol; see step (xii) above) was dissolved in 0.5 mL of methylene chloride and cooled on an ice bath. TFA (3 mL) was added and the reaction was left for 75 min. The TFA was evaporated and the residue was freeze dried from water and acetonitrile. The crude product was purified by preparative RPLC with CH$_3$CN:0.1M NH$_4$OAc (35:65) to produce 39 mg (55%) of the title compound as its HOAc salt, purity: 99%.

$^1$H NMR (400 MHz, CD$_3$OD mixture of rotamers) δ 7.5-7.4 (m, 2H), 7.32 (m, 1H, major rotamer), 7.28 (m, 1H, minor rotamer), 7.2-7.1 (m, 3H) 6.90 (t, 1H, major rotamer), 6.86 (t, minor rotamer), 5.15 (s, 1H, major rotamer), 5.14 (m, 1H, minor rotamer), 5.07 (s, 1H, minor rotamer), 4.72 (m, 1H, major rotamer), 4.65-4.45 (m, 2H), 4.30 (m, 1H, major rotamer), 4.16 (m, 1H, major rotamer), 4.03 (m, 1H, minor rotamer), 3.95 (m, 1H, minor rotamer), 2.63 (m, 1H, minor rotamer), 2.48 (m, 1H, major rotamer), 2.21 (m, 1H, major rotamer), 2.07 (m, 1H, minor rotamer), 1.89 (s, 3H)

$^{13}$C-NMR (75 MHz; CD$_3$OD): (carbonyl and/or amidine carbons, mixture of rotamers) δ 171.9, 171.2, 165.0, 162.8, 160.4

APCI-MS: (M+1)=503/505 m/z.

EXAMPLE 40

Ph(3-Cl)(5-OCHF$_2$)—(R)CH(OH)C(O)-Aze-Pab(2,6-diF)(OMe)

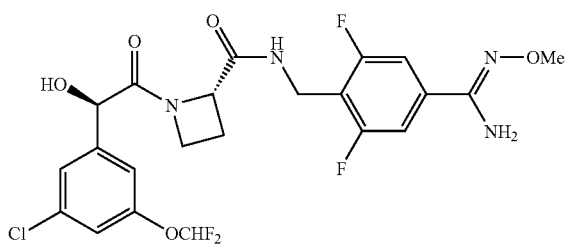

(i) Ph(3-Cl)(5-OCHF$_2$)—(R)CH(OH)C(O)-Aze-Pab(2,6-diF)(OMe,Teoc)

A mixture of Ph(3-Cl)(5-OCHF$_2$)—(R)CH(OH)C(O)-Aze-Pab(2,6-diF)(Teoc) (64 mg, 0.099 mmol; see Example 39(xii) above) and O-methyl hydroxylamine hydrochloride (50 mg, 0.60 mmol) in 4 mL of acetonitrile was heated at 70° C. for 3 h. The solvent was evaporated and the residue was partitioned between water and EtOAc. The aqueous layer was extracted twice with EtOAc and the combined organic phase was washed with water, dried (Na$_2$SO$_4$) and evaporated. The product could be used without further purification. Yield: 58 mg (87%).

$^1$H NMR (400 MHz, CDCl$_3$) δ 7.90 (bt, 1H), 7.46 (m, 1H), 7.25-6.95 (m, 5H), 6.51, t, 1H), 4.88 (s, 1H), 4.83 (m, 1H), 4.6-4.5 (m, 2H), 4.4-3.9 (m, 4H), 3.95 (s, 3H), 3.63 (m, 1H), 2.67 (m, 1H), 2.38 (m, 1H), 1.87 (broad, 1H), 0.98 (m, 2H), 0.01, s, 9H)

(ii) Ph(3-Cl)(5-OCHF$_2$)—(R)CH(OH)C(O)-Aze-Pab(2,6-diF)(OMe)

Ph(3-Cl)(5-OCHF$_2$)—(R)CH(OH)C(O)-Aze-Pab(2,6-diF)(OMe,Teoc) (58 mg, 0.086 mmol; see step (i) above) was dissolved in 3 mL of TFA, cooled on an ice bath and allowed to react for 2 h. The TFA was evaporated and the residue dissolved in EtOAc. The organic layer was washed twice with aqueous sodium carbonate and water, dried (Na$_2$SO$_4$) and evaporated. The residue was freeze-dried from water and acetonitrile to give 42 mg (92%) of the title compound. Purity: 94%.

$^1$H NMR (300 MHz, CDCl$_3$) δ 7.95 (bt, 1H), 7.2-7.1 (m, 4H), 6.99 (m, 1H), 6.52 (t, 1H), 4.88 (s, 1H), 4.85-4.75 (m, 3H), 4.6-4.45 (m, 2H), 4.29 (broad, 1H), 4.09 (m, 1H), 3.89 (s, 3H), 3.69 (m, 1H), 2.64 (m, 1H), 2.38 (m, 1H), 1.85 (broad, 1H)

$^{13}$C-NMR (100 MHz; CDCl$_3$): (carbonyl and/or amidine carbons) δ 172.1, 169.8, 151.9

APCI-MS: (M+1)=533/535 m/z

EXAMPLE 41

Ph(3-Cl)(5-OCHF$_2$)—(R)CH(OH)C(O)-Aze-Pab(2,5-diF)

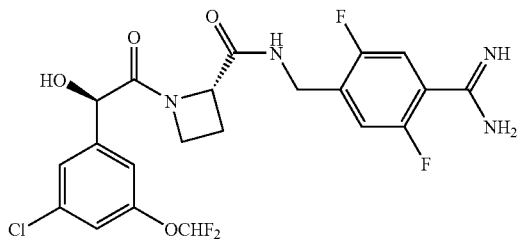

(i) 2,5-Difluoro-4-[(methylsulfinyl)(methylthio)methyl]benzonitrile (Methylsulfinyl)(methylthio)methane (3.16 g, 0.0255 mol) was dissolved in 50 mL of dry THF under argon and then cooled to −78° C. Butyllithium in hexane (16 mL 1.6M, 0.0256 mol) was added dropwise with stirring. The mixture was stirred for 15 min. Meanwhile a solution of 2,4,5-trifluorobenzonitrile (2.0 g; 0.013 mol) in 50 mL of dry THF was cooled to −78° C. under argon and the former solution was added through a cannula to the latter solution over a period of 3-5 min. After 30 min, the cooling bath was removed and when the reaction had reached room temperature it was poured into 200 mL of water. The THF was evaporated and the remaining aqueous layer was extracted three times with diethyl ether. The combined ether phase was washed with water, dried (Na$_2$SO$_4$) and evaporated. The crude product started to crystallise and could be used as such in the next step. Yield: 2.8 g (84%).

$^1$H NMR (500 MHz, CDCl$_3$) δ 7.51-7.44 (m, 2H, major diastereomer), 7.39 (dd, 1H, minor diastereomer), 5.00 (s, 1H, minor diastereomer), 4.92 (s, 1H, major diastereomer), 2.59 (s, 3H, minor diastereomer), 2.56 (s, 1H, major diastereomer), 2.46 (s, 1H, minor diastereomer), 2.40 (s, 1H, major diastereomer)

(ii) 2,5-Difluoro-4-formylbenzonitrile 2,5-Difluoro-4[(methylsulfinyl)(methylthio)methyl]benzonitrile (2.8 g, 0.0107 mol; see step (i) above) was dissolved in 100 mL of THF and 6.5 g of concentrated sulfuric acid was added. The mixture was left at room temperature for 6 days and subsequently poured into 500 mL of water. Extraction three times with diethyl ether followed and the combined ethereal phase was washed several times with water, dried (Na$_2$SO$_4$) and evaporated. The crude product was flash chromatographed on silica gel using heptane:EtOAc (8:2). Yield: 1.2 g (67%). The position of the formyl group was established by use of $^{13}$C NMR. The carbon signals from the fluorinated carbons at 160.1 and 158.4 respectively, were doublets and not quartets, which they would have been if the formyl group had been in the 2-position.

$^1$H NMR (300 MHz, CDCl$_3$) δ 10.36 (d, 1H), 7.72 (dd, 1H), 7.54 (dd, 1H)

(iii) 2,5-Difluoro-4-hydroxymethylbenzonitrile 2,5-Difluoro-4-formylbenzonitrile (3.60 g, 0.0215 mol; see step (ii) above) was dissolved in 50 mL of methanol and cooled on an ice bath. Sodium borohydride (0.815 g, 0.0215 mol) was added in portions with stirring and the reaction was left for 45 min. Water (300 mL) was added and thereafter carefully 2M HCl was added until an acidic pH was attained. The mixture was extracted three times with diethyl ether, and the combined ethereal phase was washed with water, dried (Na$_2$SO$_4$) and evaporated. The crude product crystallised soon and could be used without further purification.

Yield: 3.1 g (85%).

$^1$H NMR (300 MHz, CDCl$_3$) δ 7.45 (dd, 1H), 7.30 (dd, 1H), 4.85 (s, 2H), 2.10 (broad, 1H)

(iv) 4-Cyano-2,5-difluorobenzyl methanesulfonate

To an ice cooled solution of 2,5-difluoro-4-hydroxymethylbenzonitrile (3.10 g, 0.0183 mol; see step (iii) above) and methanesulfonyl chloride (2.21 g, 0.0192 mol) in 60 mL of methylene chloride was added triethyl amine (1.95 g, 0.0192 mol) with stirring. After 1.5 h at 0° C. the mixture was washed with water, dried (Na$_2$SO$_4$) and evaporated. The product could be used without further purification. Yield: 4.5 g (99%).

$^1$H NMR (300 MHz, CDCl$_3$) δ 7.45-7.35 (m, 2H), 5.32 (s, 2H), 3.13 (s, 3H)

(v) 4-Azidomethyl-2,5-difluorobenzonitrile

A mixture of 4-cyano-2,5-difluorobenzyl methanesulfonate (4.5 g, 0.0182 mol; see step (iv) above) and sodium azide (2.0 g, 0.031 mol) in 20 mL of water and 40 mL of DMF was stirred at room temperature for 2 h. It was subsequently poured into 300 mL of water and extracted three times with diethyl ether. The combined ethereal phase was washed several times with water, dried (Na$_2$SO$_4$) and evaporated. A small sample was evaporated for NMR purposes and the product crystallised. The rest was evaporated cautiously but not until complete dryness. Yield (theoretically 3.5 g) is assumed to be almost quantitative based on NMR and analytical HPLC.

$^1$H NMR (500 MHz, CDCl$_3$) 6.38 (dd, 1H), 7.32 (dd, 1H), 4.54 (s, 2H)

(vi) 4-Aminomethyl-2,5-difluorobenzonitrile

This reaction was carried out according to the procedure described in *J. Chem. Res. (M)* (1992) 3128. To a suspension of 300 mg of 10% Pd/C (50% moisture) in 20 mL of water was added a solution of sodium borohydride (0.779 g, 0.0206 mol) in 20 mL of water. Some gas evolution resulted. 4-Azidomethyl-2,5-difluorobenzonitrile (1.00 g, 5.15 mmol; from step (v) above) was dissolved in 60 mL of THF and added to the aqueous mixture on an ice bath. The mixture was stirred for 1.5 h whereafter 10 mL of 2M HCl was added and the mixture was filtered through Celite. The Celite was rinsed with more water and the combined aqueous phase was washed with EtOAc and subsequently made alkaline with 2M NaOH. Extraction three times with methylene chloride followed and the combined organic phase was washed with water, dried (Na$_2$SO$_4$) and evaporated.

Yield: 0.47 g (54%).

$^1$H NMR (300 MHz, CDCl$_3$) δ 7.39 (dd, 1H), 7.29 (dd, 1H), 3.99 (s, 2H), 1.45 (broad, 2H)

(vii) 2,5-Difluoro-4-tert-butoxycarbonylaminomethylbenzonitrile

A solution of 4-aminomethyl-2,5-difluorobenzonitrile (0.46 g, 2.7 mmol; see step (vi) above) and di-tert-butyl dicarbonate (0.60 g, 2.7 mmol) in 10 mL of THF was stirred overnight. The THF was evaporated and the residue was partitioned between water and EtOAc. The organic layer was washed with water, dried ($Na_2SO_4$) and evaporated. The product could be used without further purification. Yield: 0.71 g (97%).

$^1$H NMR (300 MHz, $CDCl_3$) δ 7.35-7.2 (m, 2H), 5.11 (broad triplet, 1H), 4.38 (d, 2H), 1.45 (s, 9H)

(viii) Boc-Pab(2,5-diF)(OH)

A mixture of 2,5-difluoro-4-tert-butoxycarbonylaminomethylbenzonitrile (0.70 g, 2.6 mmol; see step (vii) above), hydroxylamine hydrochloride (0.54 g, 7.8 mmol) and triethylamine (0.79 g, 7.8 mmol) in 10 mL of ethanol was stirred at room temperature for 6 days. It was then partitioned between water and methylene chloride. The aqueous layer was extracted with methylene chloride and the combined organic phase was washed with water, dried ($Na_2SO_4$) and evaporated. The product could be used without further purification. Yield: 0.72 g (92%).

$^1$H NMR (500 MHz, $CD_3OD$) δ 7.27 (dd, 1H), 7.12 (dd, 1H), 4.29 (s, 2H), 1.47 (s, 9H)

(ix) Boc-Pab(2,5-diF)×HOAc

This reaction was carried out according to the procedure described by Judkins et al, *Synth. Comm.* (1998) 4351. Boc-Pab(2,5-diF)(OH) (0.70 g, 2.3 mmol; see step (viii) above), acetic anhydride (0.25 g, 2.4 mmol) and 230 mg of 10% Pd/C (50% moisture) in 70 mL of acetic acid was hydrogenated at 5 atm pressure for 2.5 h. The mixture was filtered through Celite and evaporated. The residue was freeze dried from acetonitrile and water. The product could be used without further purification in the next step. Yield: 0.80 g (100%).

$^1$H NMR (500 MHz, $CD_3OD$) δ 7.49 (dd, 1H), 7.31 (dd, 1H), 4.33 (s, 2H), 1.91 (s, 3H), 1.46 (s, 9H)

(x) Boc-Pab(2,5-diF)(Teoc)

To a suspension of Boc-Pab(2,5-diF)×HOAc (0.80 g, 2.3 mmol; see step (ix) above) in 50 mL of THF was added 2-(trimethylsilyl)ethyl p-nitrophenyl carbonate (0.85 g, 3.0 mmol). A solution of potassium carbonate (0.80 g, 5.8 mmol) in 10 mL of water was added dropwise. The mixture was stirred overnight. The excess Teoc reagent was destroyed by addition of glycine (0.100 g) and potassium carbonate (0.75 g) to the solution, letting it react for an additional 2 h. The THF was evaporated and the residue was partitioned between water and methylene chloride. The aqueous layer was extracted with methylene chloride and the combined organic phase was washed with water, dried ($Na_2SO_4$) and evaporated. Flash chromatography on silica gel with heptane:EtOAc (2:1) gave 0.72 g (72%) of pure compound.

$^1$H NMR (400 MHz, $CDCl_3$) δ 8.00 (dd, 1H), 7.15 (dd, 1H), 4.98 (broad, 1H), 4.36 (bd, 2H), 4.24 (m, 2H), 1.45 (s, 9H), 1.12 (m, 2H), 0.07 (s, 9H)

(xi) H-Pab(2,5-diF)(Teoc)×2HCl

Boc-Pab(2,5-diF)(Teoc) (0.38 g, 0.88 mmol; see step (x) above) was dissolved in 50 mL of EtOAc saturated with HCl(g). The mixture was left for 30 min and evaporated.

$^1$H NMR (500 MHz, $CD_3OD$) δ 7.75-7.6 (m, 2H), 4.46 (m, 2H), 4.3 (s, 2H), 1.15 (m, 2H), 0.07 (s, 9H)

(xii) Boc-Aze-Pab(2,5-diF)(Teoc)

To a stirred solution of Boc-Aze-OH (0.189 g, 0.94 mmol), H-Pab(2,5-diF)(Teoc)×2HCl (0.36 g, 0.89 mmol; see step (xi) above) and PyBOP (0.54 g, 1.03 mmol) in 5 mL of DMF was added diisopropylethyl amine (0.49 g, 3.8 mmol) and the mixture was allowed to react overnight. The resultant was then poured into aqueous sodium bicarbonate and extracted three times with EtOAc. The combined organic phase was washed with water, dried ($Na_2SO_4$) and evaporated. Flash chromatography on silica gel with heptane:EtOAc (3:7) gave a sufficiently pure compound. Yield: 0.25 g (48%).

$^1$H NMR (500 MHz, $CDCl_3$) δ 7.98 (dd, 1H), 7.13 (dd, 1H), 4.69 (m, 1H), 4.53 (m, 2H), 4.22 (m, 2H), 3.92 (m, 1H), 3.79 (m, 1H), 2.55-2.35 (m, 2H), 1.44 (s, 9H), 1.11 (m, 2H), 0.06 (s, 9H)

(xiii) H-Aze-Pab(2,5-diF)(Teoc)×2HCl

Boc-Aze-Pab(2,5-diF)(Teoc) (0.25 g, 0.49 mmol; see step (xii) above) was dissolved in 50 mL of EtOAc saturated with HCl(g). The mixture was left for 30 min. and evaporated. The product was used in the next step without further purification. Yield: 0.23 g (97%).

$^1$H NMR (400 MHz, $CD_3OD$) δ 7.59 (dd, 1H), 7.47 (dd, 1H), □5.14 (m, 1H), 4.54 (m, 2H), 4.48 (m, 2H), 4.15 (m, 1H), 3.96 (m, 1H), 2.87 (m, 1H), 2.56 (m, 1H), 1.17 (m, 2H), 0.05 (s, 9H)

(xiv) Ph(3-Cl)(5-OCHF$_2$)—(R)CH(OH)C(O)-Aze-Pab(2,5-diF)(Teoc)

To a solution of Ph(3-Cl)(5-OCHF$_2$)—(R)CH(OH)C(O)OH (0.12 g, 0.47 mmol; see Example 1(viii) above), H-Aze-Pab(2,5-diF)(Teoc)×2HCl (0.23 g, 0.47 mmol; see step (xiii) above) and PyBOP (0.27 g, 0.52 mmol) in 10 mL of DMF was added diisopropylethyl amine (0.245 g, 1.90 mmol), and the mixture was stirred overnight. The resultant was poured into water and extracted three times with EtOAc. The combined organic phase was washed with water, dried ($Na_2SO_4$) and evaporated. Flash chromatography on silica gel with EtOAc gave 100 mg of a pure fraction and 30 mg of a to 90% pure fraction. Total yield: 0.13 g (41%).

$^1$H NMR (400 MHz, $CDCl_3$) δ 9.80 (broad, 1H), 8.05 (bt, 1H), 7.94 (dd, 1H), 7.20 (m, 1H), 7.2-7.1 (m, 2H), 7.02 (m, 1H), 6.54 (t, 1H), 4.93 (s, 1H), 4.91 (m, 1H), 4.51 (m, 2H), 4.28 (broad, 1H), 4.23 (m, 2H), 4.13 (m, 1H), 3.74 (m, 1H), 2.69 (m, 1H), 2.43 (m, 1H), 1.73 (broad, 1H), 1.11 (m, 2H), 1.11 (s, 9H)

(xv) Ph(3-Cl)(5-OCHF$_2$)—(R)CH(OH)C(O)-Aze-Pab(2,5-diF)

Ph(3-Cl)(5-OCHF$_2$)—(R)CH(OH)C(O)-Aze-Pab(2,5-diF)(Teoc) (60 mg (0.093 mmol) of the pure fraction from step (xiv) above) was dissolved in 3 mL of TFA and left at room temperature for 1 h. The TFA was evaporated and the residue was freeze-dried from water and acetonitrile to produce 55 mg (96%) of the title compound as its TFA salt, purity: >99%.

$^1$H NMR (500 MHz, $CD_3OD$ mixture of rotamers) δ 7.55-7.3 (m, 3H), 7.2-7.1 (m, 2H), 6.88 (t, 1H, major rotamer), 6.86 (t, 1H, minor rotamer), 5.22 (m, 1H, minor rotamer), 5.20 (s, 1H, major rotamer), 5.13 (s, 1H, minor rotamer), 4.80 (m, 1H, major rotamer), 4.6-4.45 (m, 2H), 4.36 (m, 1H, major rotamer), 4.19 (m, 1H, major rotamer), 4.07 (m, 1H, minor rotamer), 3.98 (m, 1H, minor rotamer), 2.70 (m, 1H, minor rotamer), 2.54 (m, 1H, major rotamer), 2.28 (m, 1H, major rotamer), 2.14 (m, 1H, minor rotamer)

EXAMPLE 42

Ph(3-Cl)(5-OCHF$_2$)—(R)CH(OH)C(O)-Aze-Pab(2, 5-diF)(OMe)

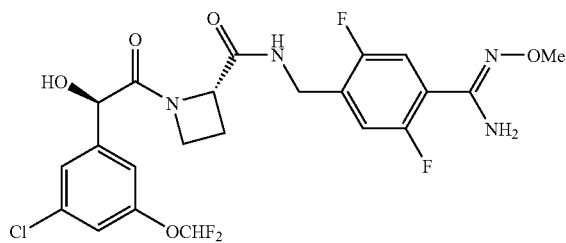

(i) Ph(3-Cl)(5-OCHF$_2$)—(R)CH(OH)C(O)-Aze Pab (2,5-diF)(OMe,Teoc)

A mixture of Ph(3-Cl)(5-OCHF$_2$)—(R)CH(OH)C(O)-Aze-Pab(2,5-diF)(Teoc) (40 mg, 0.062 mmol; see Example 41(xiv) above) and O-methyl hydroxylamine hydrochloride (58 mg, 0.70 mmol) in 5 mL of acetonitrile was heated at 70° C. for 2 h. The solvent was evaporated and the residue was partitioned between water and EtOAc. The aqueous layer was extracted with EtOAc and the combined organic phase was washed with water, dried (Na$_2$SO$_4$) and evaporated. The product could be used without further purification. Yield: 35 mg (84%).

$^1$H NMR (600 MHz, CDCl$_3$) δ 7.99 (bt, 1H), 7.72 (s, 1H), 7.20 (m, 1H) 7.15-7.1 (m, 1H), 7.07 (dd, 1H), 7.01 (m, 1H), 6.53 (t, 1H), 4.90 (s, 1H), 4.88 m, 1H), 4.48 (m, 2H), 4.2-4.1 (m, 3H), 3.95 (s, 3H), 3.67 (m, 1H), 2.68 (m, 1H), 2.41 (m, 1H), 0.97 (m, 2H), 0.07 (s, 9H)

(ii) Ph(3-Cl)(5-OCHF$_2$)—(R)CH(OH)C(O)-Aze-Pab (2,5-diF)(OMe)

Ph(3-Cl)(5-OCHF$_2$)—(R)CH(OH)C(O)-Aze-Pab(2,5-diF)(OMe,Teoc) (35 mg, 0.052 mmol; see step (i) above) was dissolved in 3 mL of TFA and allowed to react for 30 min. The TFA was evaporated and the residue freeze-dried from water and acetonitrile to give 29 mg (99%) of the title compound. Purity: 97%.

$^1$H NMR (300 MHz, CDCl$_3$) δ 8.01 (bt, 1H), 7.45 (dd, 1H), 7.20 (m, 1H), 7.15 (m, 1H), 7.09 (dd, 1H), 7.02 (m, 1H), 6.54 (t, 1H), 5.2-5.0 (m, 2H), 4.95-4.85 (m, 2H), 4.6-4.4 (m, 2H), 4.25 (broad, 1H), 4.13 (m, 1H), 3.90 (s, 3H), 3.71 (m, 1H), 2.69 (m, 1H), 2.43 (m, 1H)

$^{13}$C-NMR (75 MHz; CDCl$_3$): (carbonyl and/or amidine carbons) δ 173.0, 170.9, 152.6

APCI-MS: (M+1)=533/535 m/z.

EXAMPLE 43

Ph(3-Cl)(5-OCHF$_2$)—(R)CH(OH)C(O)-Aze-Pab (OEt)

(i) Ph(3-Cl)(5-OCHF$_2$)—(R)CH(OH)C(O)-Aze-Pab (OEt, Teoc)

Ph(3-Cl)(5-OCHF$_2$)—(R)CH(OH)C(O)-Aze-Pab(Teoc) (55 mg, 0.090 mmol; see Example 1(ix) above) and O-ethyl-hydroxylamine hydrochloride (53 mg, 0.54 mmol) were dissolved in 4 mL of THF. The mixture was stirred at 60° C. for 5 h. The solvent was evaporated. The residue was chromatographed on silica gel, eluting with methylene chloride:methanol (95:5) to afford 55 mg (93%) of the sub-title compound.

$^1$H-NMR (400 MHz; CDCl$_3$): δ 7.84 (bt, 1H), 7.59 (bs, 1H), 7.47 (bd, 1H), 7.29 (bd, 1H), 7.21 (m, 1H), 7.14 (m, 1H), 7.02 (m, 1H), 6.53 (t, 1H), 4.90 (s, 1H), 4.86 (m, 1H), 4.55-4.4 (m, 2H), 4.25-4.1 (m, 5H), 3.69 (m, 1H), 2.66 (m, 1H), 2.41 (m, 1H), 1.33 (t, 3H), 0.98 (m, 2H), 0.02 (s, 9H)

(ii) Ph(3-Cl, 5-OCHF$_2$)—(R)CH(OH)C(O)-Aze-Pab (OEt)

To an ice-cold solution of Ph(3-Cl)(5-OCHF$_2$)—(R)CH(OH)C(O)-Aze-Pab(OEt, Teoc) (55 mg, 0.084 mmol; see step (i) above) in 0.5 mL of methylene chloride was added 3 mL of TFA. The mixture was stirred (ice-bath) for 160 minutes. The material was purified using preparative HPLC. The fractions of interest were pooled and freeze-dried (2×), yielding 20 mg (47%) of the title compound.

$^1$H-NMR (400 MHz; CD$_3$OD) rotamers: δ 7.59 (bd, 2H), 7.35 (m, 1H), 7.32 (bd, 2H), 7.25-7.1 (m, 2H), 6.89 (t, 1H, major rotamer), 6.86 (t, 1H, minor rotamer), 5.18 (s, 1H, major rotamer), 5.18 (m, 1H, minor rotamer), 5.11 (s, 1H, minor rotamer), 4.77 (m, 1H), 4.5-4.3 (m, 3H), 4.2-3.9 (m, 3H), 2.67 (m, 1H, minor rotamer), 2.52 (m, 1H, major rotamer), 2.28 (m, 1H, major rotamer), 2.15 (m, 1H, minor rotamer), 1.28 (t, 3H)

$^{13}$C-NMR (100 MHz; CD$_3$OD): (carbonyl and/or amidine carbons, rotamers) 172.4, 171.9, 171.4, 153.8, 152.3

MS (m/z) 509 (M−1)$^-$, 511 (M+1)$^+$

EXAMPLE 44

Ph(3-Cl)(5-OCHF$_2$)—(R)CH(OH)C(O)-Aze-Pab (OnPr)

(i) Ph(3-Cl)(5-OCHF$_2$)—(R)CH(OH)C(O)-Aze-Pab (OnPr, Teoc)

Ph(3-Cl)(5-OCHF$_2$)—(R)CH(OH)C(O)-Aze-Pab(Teoc) (53 mg, 0.087 mmol; see Example 1(ix) above) and O-n-propylhydroxylamine hydrochloride, 58 mg (0.52 mmol) were dissolved in 4 mL of THF. The mixture was stirred at 60° C. for 5 h. The solvent was evaporated. The residue was chromatographed on silica gel, eluting with methylene chloride:methanol (95:5) to afford 51 mg (88%) of the sub-title compound.

$^1$H-NMR (400 MHz; CDCl$_3$): δ 7.84 (m, 1H), 7.59 (bs, 1H), 7.47 (bd, 2H), 7.28 (bd, 2H), 7.21 (m, 1H), 7.14 (m, 1H), 7.02 (m, 1H), 6.53 (t, 1H), 4.90 (s, 1H), 4.85 (m, 1H), 4.55-4.4 (m, 2H), 4.2-4.05 (m, 5H), 3.69 (m, 1H), 2.65 (m, 1H), 2.41 (m, 1H), 1.74 (m, 2H), 1.05-0.95 (m, 5H), 0.03 (s, 9H)

(ii) Ph(3-Cl)(5-OCHF$_2$)—(R)CH(OH)C(O)-Aze-Pab (OnPr)

To an ice-cold solution of Ph(3-Cl)(5-OCHF$_2$)—(R)CH(OH)C(O)-Aze-Pab(OnPr, Teoc) (51 mg, 0.078 mmol; see step (i) above) in 0.5 mL of methylene chloride was added 3 mL of TFA. The mixture was stirred (ice-bath) for 110 minutes. The material was purified using preparative HPLC. The fraction of interest was evaporated and freeze-dried, yielding 20 mg (47%) of the title compound.

$^1$H-NMR (500 MHz; CD$_3$OD) rotamers: δ 7.61 (bd, 2H), 7.38 (m, 1H), 7.35 (bd, 2H), 7.22 (m, 1H, major rotamer), 7.18 (m, 1H), 7.15 (m, 1H, minor rotamer), 6.92 (t, 1H, major rotamer), 6.89 (t, 1H, minor rotamer), 5.20 (s, 1H, major rotamer), 5.20 (m, 1H, minor rotamer), 4.80 (m, 1H, major rotamer), 4.5-4.4 (m, 2H, including minor rotamer corresponding to major at 4.37), 4.37 (m, 1H, major rotamer), 4.18 (m, 1H, major rotamer), 4.09 (m, 1H, minor rotamer), 3.99 (m, 2H), 2.70 (m, 1H, minor rotamer), 2.54 (m, 1H, major rotamer), 2.30 (m, 1H, major rotamer), 2.18 (m, 1H, minor rotamer), 1.73 (m, 2H), 1.01 (t, 3H)

$^{13}$C-NMR (125 MHz; CD$_3$OD): (carbonyl and/or amidine carbons, rotamers) δ 171.4, 153.8, 152.3

MS (m/z) 523 (M−1)$^−$, 525 (M+1)$^+$

EXAMPLE 45

Ph(3-Cl)(5-OCHF$_2$)—(R)CH(OH)C(O)-Aze-Pab (OiPr)

(i) Ph(3-Cl)(5-OCHF$_2$)—(R)CH(OH)C(O)-Aze-Pab (OiPr, Teoc)

Ph(3-Cl)(5-OCHF$_2$)—(R)CH(OH)C(O)-Aze-Pab(Teoc) (50 mg, 0.082 mmol; see Example 1(ix) above) and O-i-propylhydroxylamine hydrochloride, 55 mg (0.49 mmol) were dissolved in 4 mL of THF. The mixture was stirred at 60° C. for 5 h. The solvent was evaporated. The residue was chromatographed on silica gel, eluting with methylene chloride:methanol (95:5) to afford 46 mg (84%) of the sub-title compound.

$^1$H-NMR (400 MHz; CDCl$_3$): δ 7.84 (m, 1H), 7.57 (bs, 1H), 7.48 (bd, 2H), 7.29 (bd, 2H), 7.21 (m, 1H), 7.14 (m, 1H), 7.02 (m, 1H), 6.53 (t, 1H), 4.91 (s, 1H), 4.87 (m, 1H), 4.55-4.45 (m, 2H), 4.42 (m, 1H), 4.2-4.1 (m, 3H), 3.69 (m, 1H), 2.66 (m, 1H), 2.42 (m, 1H), 1.30 (d, 6H), 0.98 (m, 2H), 0.02 (s, 9H)

(ii) Ph(3-Cl)(5-OCHF$_2$)—(R)CH(OH)C(O)-Aze-Pab (OiPr)

To an ice-cold solution of Ph(3-Cl)(5-OCHF$_2$)—(R)CH(OH)C(O)-Aze-Pab(OiPr, Teoc) (46 mg, 0.069 mmol; see step (i) above) in 0.5 mL of methylene chloride was added 3 mL of TFA. The mixture was stirred (ice-bath) for 150 minutes. The material was purified using preparative HPLC. The fraction of interest was evaporated and freeze-dried (2×), yielding 22 mg (58%) of the title compound.

$^1$H-NMR (400 MHz; CD$_3$OD) rotamers: δ 7.59 (d, 2H), 7.35 (m, 1H), 7.32 (d, 2H), 7.19 (m, 1H, major rotamer), 7.15 (m, 1H), 7.12 (m, 1H, minor rotamer), 6.89 (t, 1H, major rotamer), 6.86 (t, 1H, minor rotamer), 5.18 (s, 1H, major rotamer), 5.18 (m, 1H, minor rotamer), 5.12 (s, 1H, minor rotamer), 4.78 (m, 1H, major rotamer), 4.5-3.9 (m, 5H), 2.67 (m, 1H, minor rotamer), 2.52 (m, 1H, major rotamer), 2.28 (m, 1H, major rotamer), 2.15 (m, 1H, minor rotamer), 1.26 (d, 6H)

$^{13}$C-NMR (100 MHz; CD$_3$OD): (carbonyl and/or amidine carbons, rotamers) δ 171.9, 171.4, 153.6.

MS (m/z) 523 (M−1)$^−$, 525 (M+1)$^+$.

EXAMPLE 46

The title compounds of Examples 3, 6, 9, 10, 13 to 15, 17, 19, 21, 23, 25, 27, 28, 32, 34, 36, 38, 39 and 41 were tested in Test A above and were found to exhibit IC$_{50}$TT values of less than 3.5 μM. Those of Examples 3, 6, 9, 10, 13, 15, 17, 19, 21, 23, 27, 32, 34 and 39 were found to exhibit values of less than 0.02 μM; those of Examples 25 and 28 less than 0.03 μM, that of Example 14 less than 0.04 μM; and those of Examples 38 and 41 less than 0.15 μM.

EXAMPLE 47

The title compounds of Examples 3, 6, 13, 15, 17, 19, 21, 23, 25, 27, 28, 32 and 34 were tested in Test D above and were found to exhibit an IC$_{50}$ APTT value of less than 1 μM.

EXAMPLE 48

The title compounds of Examples 1, 2, 4, 5, 7, 12, 16, 18, 20, 22, 24, 26, 29, 30, 33 and 43 to 45 were tested in Test E above and were found to exhibit oral and/or parenteral bioavailability in the rat as the corresponding active inhibitor (free amidine).

EXAMPLE 49

Title compounds of Examples 1, 2, 7, 8, 11, 12, 16, 18, 20, 22, 24, 26, 29, 33, 37, 40, 43 and 45 were tested in Test G above and were found to be converted to the corresponding active inhibitor (free amidine) in liver microsomes from humans and from rats.

| Abbreviations | |
|---|---|
| Ac = | acetyl |
| AcOH = | acetic acid |
| APCI = | atmospheric pressure chemical ionisation (in relation to MS) |
| API = | atmospheric pressure ionisation (in relation to MS) |
| aq. = | aqueous |
| AUC = | area under the curve |
| Aze = | (S)-azetidine-2-carboxylate (unless otherwise specified) |
| AzeOH = | azetidine-2-carboxylic acid |
| Bn = | benzyl |
| Boc = | tert-butyloxycarbonyl |
| BSA = | bovine serum albumin |
| Bu = | butyl |
| Bzl = | benzyl |
| CI = | chemical ionisation (in relation to MS) |
| d = | day(s) |
| DCC = | dicyclohexyl carbodiimide |
| DIBAL-H = | di-isobutylaluminium hydride |
| DIPEA = | diisopropylethylamine |
| DMAP = | 4-(N,N-dimethyl amino) pyridine |
| DMF = | dimethylformamide |
| DMSO = | dimethylsulfoxide |
| DVT = | deep vein thrombosis |
| EDC = | 1-(3-dimethylaminopropyl)-3-ethylcarbodiimide hydrochloride |
| e.e. = | enantiomeric excess |
| Et = | ethyl |
| ether = | diethyl ether |
| EtOAc = | ethyl acetate |
| EtOH = | ethanol |
| Et$_2$O = | diethyl ether |
| h = | hour(s) |
| HATU = | O-(azabenzotriazol-1-yl)-N,N,N',N'-tetramethyluronium hexafluorophosphate |
| HBTU = | [N,N,N',N'-tetramethyl-O-(benzotriazol-1-yl)uronium hexafluorophosphate] |
| HCl = | hydrochloric acid, hydrogen chloride gas or hydrochloride salt (depending on context) |
| Hex = | hexanes |
| HOAc = | acetic acid |
| HPLC = | high performance liquid chromatography |
| LC = | liquid chromatography |
| Me = | methyl |
| MEM = | methoxyethoxymethyl |
| MeOH = | methanol |
| min = | minute(s) |

-continued

Abbreviations

| | |
|---|---|
| MS = | mass spectroscopy |
| MTBE = | methyl tert-butyl ether |
| NADH = | nicotinamide adenine dinucleotide, reduced form |
| NADPH = | nicotinamide adenine dinucleotide phosphate, reduced form |
| NIH = | National Institute of Health (US) |
| NIHU = | National Institute of Health units |
| NMR = | nuclear magnetic resonance |
| OAc = | acetate |
| Pab = | para-amidinobenzylamino |
| H-Pab = | para-amidinobenzylamine |
| Ph = | phenyl |
| Pr = | propyl |
| Pro = | (S)-prolinyl |
| PyBOP = | (benzotriazol-1-yloxy)tripyrrolidinophosphonium hexafluorophosphate |
| QF = | tetrabutylammonium fluoride |
| RedAl = | sodium bis(2-methoxyethoxy)aluminium hydride |
| RPLC = | reverse phase high performance liquid chromatography |
| rt/RT = | room temperature |
| SOPs = | standard operating procedures |
| TBTU = | [N,N,N',N'-tetramethyl-O-(benzotriazol-1-yl)uronium tetrafluoroborate] |
| TEA = | triethylamine |
| Teoc = | 2-(trimethylsilyl)ethoxycarbonyl |
| TEMPO = | 2,2,6,6-tetramethyl-1-piperidinyloxy free radical |
| TFA = | trifluoroacetic acid |
| THF = | tetrahydrofuran |
| THP = | tetrahydropyranyl |
| TLC = | thin layer chromatography |
| TMSCl = | trimethylsilyl chloride |
| TMSCN = | trimethylsilyl cyanide |
| UV = | ultraviolet |
| Z = | benzyloxycarbonyl |

Prefixes n, s, i and t have their usual meanings: normal, secondary, iso and tertiary. The prefix c means cyclo.

The invention claimed is:

1. A method of treating thrombosis, comprising administering to a human in need thereof a therapeutically effective amount of a compound selected from Ph(3-Cl)(5-OCHF$_2$)—(R)CH(OH)C(O)-Aze-Pab(OMe),
Ph(3-Cl)(5-OCHF$_2$)—(R)CH(OH)C(O)-Aze-Pab(OH) and
Ph(3-Cl)(5-OCHF$_2$)—(R)CH(OH)C(O)-Aze-Pab, or a pharmaceutically acceptable salt of any of these.

2. A method of treating hypercoagulability in blood and/or tissues, comprising administering to a human in need thereof a therapeutically effective amount of a compound selected from Ph(3-Cl)(5-OCHF$_2$)—(R)CH(OH)C(O)-Aze-Pab(OMe),
Ph(3-Cl)(5-OCHF$_2$)—(R)CH(OH)C(O)-Aze-Pab(OH) and
Ph(3-Cl)(5-OCHF$_2$)—(R)CH(OH)C(O)-Aze-Pab, or a pharmaceutically acceptable salt of any of these.

3. The method as claimed in claim 1 or claim 2, wherein the compound is Ph(3-Cl)(5-OCHF$_2$)—(R)CH(OH)C(O)-Aze-Pab(OMe), or a pharmaceutically acceptable salt thereof.

4. The method as claimed in claim 1, wherein the thrombosis is venous thrombosis.

5. The method as claimed in claim 4, wherein the venous thrombosis is deep vein thrombosis.

6. The method as claimed in claim 1, wherein the thrombosis is associated with pulmonary embolism or arterial thrombosis.

7. The method as claimed in claim 1, wherein the thrombosis is associated with stroke.

8. The method as claimed in claim 1, wherein the thrombosis is associated with atrial fibrillation.

9. The method as claimed in claim 1, wherein the atrial fibrillation is non-valvular atrial fibrillation.

10. The method as claimed in claim 1 or claim 2, wherein the compound is combined and/or co-administered with an antiplatelet agent selected from the group consisting of acetylsalicylic acid, ticlopidine, clopidogrel and mixtures thereof; a thromboxane receptor and/or synthetase inhibitor; a fibrinogen receptor antagonist; a prostacyclin mimetic; aphosphodiesterase inhibitor;
an ADP-receptor (P$_2$T) antagonist; and/or an inhibitor of carboxypeptidase U (CPU).

11. The method as claimed in claim 1 or claim 2, wherein the compound is combined and/or co-administered with the antiplatelet agent acetylsalicylic acid.

12. The method as claimed in claim 2, wherein the hypercoagulability is associated with stroke.

13. The method as claimed in claim 2, wherein the hypercoagulability is associated with atrial fibrillation.

14. The method as claimed in claim 13, wherein the atrial fibrillation is non-valvular atrial fibrillation.

15. The method as claimed in claim 1 or claim 2, wherein the compound is Ph(3-Cl)(5-OCHF$_2$)—(R)CH(OH)C(O)-Aze-Pab(OH), or a pharmaceutically acceptable salt thereof.

16. The method as claimed in claim 1 or claim 2, wherein the compound is Ph(3-Cl)(5-OCHF$_2$)—(R)CH(OH)C(O)-Aze-Pab, or a pharmaceutically acceptable salt thereof 17. The method as claimed in claim 1 or claim 2, wherein the compound is present as the free base.

* * * * *